(12) United States Patent
Graul et al.

(10) Patent No.: US 10,136,884 B2
(45) Date of Patent: *Nov. 27, 2018

(54) METHOD AND APPARATUS FOR ATTACHING TISSUE TO BONE, INCLUDING THE PROVISION AND USE OF A NOVEL KNOTLESS SUTURE ANCHOR SYSTEM, INCLUDING A RETRACTABLE SHEATH

(71) Applicant: Pivot Medical, Inc., Sunnyvale, CA (US)

(72) Inventors: Jeremy Graul, Elk Grove, CA (US); J. Brook Burley, Mountain View, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 187 days.

This patent is subject to a terminal disclaimer.

(21) Appl. No.: 14/881,259

(22) Filed: Oct. 13, 2015

(65) Prior Publication Data

US 2016/0030034 A1 Feb. 4, 2016

Related U.S. Application Data

(63) Continuation-in-part of application No. 14/876,091, filed on Oct. 6, 2015, which is a continuation of
(Continued)

(51) Int. Cl.
*A61B 17/04* (2006.01)
(52) U.S. Cl.
CPC ...... *A61B 17/0401* (2013.01); *A61B 17/0485* (2013.01); *A61B 2017/0403* (2013.01);
(Continued)

(58) Field of Classification Search
CPC ........ A61B 17/0401; A61B 2017/0409; A61B 2017/0414; A61B 2017/0424;
(Continued)

(56) References Cited

U.S. PATENT DOCUMENTS

| 919,138 A | 4/1909 | Drake et al. |
| 2,416,260 A | 2/1947 | Karle |

(Continued)

FOREIGN PATENT DOCUMENTS

| EP | 0 232 049 | 8/1987 |
| EP | 0 241 240 | 10/1987 |

(Continued)

*Primary Examiner* — Robert Lynch
(74) *Attorney, Agent, or Firm* — Pandiscio & Pandiscio

(57) ABSTRACT

Apparatus for securing a suture to a bone, the apparatus including an anchor configured to have the suture connected thereto; and an inserter for manipulating the anchor, the inserter including a handle; a shaft mounted to the handle and configured to releasably hold the anchor thereto; a retractable sheath movably mounted to the handle, the retractable sheath having a first extended position and a second retracted position, wherein the retractable sheath is disposed coaxially over at least a portion of the anchor when the retractable sheath is in its first extended position, and the retractable sheath is withdrawn from the anchor when the retractable sheath is in its second retracted position; and an outer tube mounted to the handle, the outer tube being disposed coaxially over the retractable sheath.

27 Claims, 55 Drawing Sheets

Related U.S. Application Data application No. 13/830,501, filed on Mar. 14, 2013, now Pat. No. 9,149,268, which is a continuation-in-part of application No. 13/642,168, filed as application No. PCT/US2011/021173 on Jan. 13, 2011, now Pat. No. 9,451,943, and a continuation-in-part of application No. 12/839,246, filed on Jul. 19, 2010, now Pat. No. 9,179,905, said application No. 13/830,501 is a continuation-in-part of application No. 13/538,378, filed on Jun. 29, 2012, now Pat. No. 9,101,355.

(60) Provisional application No. 61/326,709, filed on Apr. 22, 2010, provisional application No. 61/271,205, filed on Jul. 17, 2009, provisional application No. 61/502,621, filed on Jun. 29, 2011, provisional application No. 61/644,129, filed on May 8, 2012, provisional application No. 61/718,997, filed on Oct. 26, 2012, provisional application No. 62/064,194, filed on Oct. 15, 2014.

(52) U.S. Cl.
CPC ........ *A61B 2017/0409* (2013.01); *A61B 2017/0414* (2013.01); *A61B 2017/0424* (2013.01); *A61B 2017/0448* (2013.01); *A61B 2017/0451* (2013.01); *A61B 2017/0453* (2013.01); *A61B 2017/0458* (2013.01)

(58) Field of Classification Search
CPC .... A61B 2017/0448; A61B 2017/0451; A61B 2017/0458
See application file for complete search history.

(56) References Cited

U.S. PATENT DOCUMENTS

| | | |
|---|---|---|
| 2,579,192 A | 12/1951 | Kohl |
| 2,808,055 A | 10/1957 | Thayer |
| 3,566,739 A | 3/1971 | Lebar |
| 3,708,883 A | 1/1973 | Flander |
| 4,408,938 A | 10/1983 | Maguire |
| 4,484,570 A | 11/1984 | Sutter et al. |
| 4,492,226 A | 1/1985 | Belykh et al. |
| 4,590,928 A | 5/1986 | Hunt et al. |
| 4,605,414 A | 8/1986 | Czajka |
| 4,632,100 A | 12/1986 | Somers et al. |
| 4,708,132 A | 11/1987 | Silvestrini |
| 4,741,330 A | 5/1988 | Hayhurst |
| 4,778,468 A | 10/1988 | Hunt et al. |
| 4,779,616 A | 10/1988 | Johnson |
| 4,870,957 A | 10/1989 | Goble et al. |
| 4,871,289 A | 10/1989 | Choiniere |
| 4,927,421 A | 5/1990 | Goble et al. |
| 5,037,422 A | 8/1991 | Hayhurst et al. |
| 5,046,513 A | 9/1991 | Gatturna et al. |
| 5,176,682 A | 1/1993 | Chow |
| 5,207,679 A | 5/1993 | Li |
| 5,209,753 A | 5/1993 | Biedermann et al. |
| 5,224,946 A | 7/1993 | Hayhurst et al. |
| 5,226,426 A | 7/1993 | Yoon |
| 5,236,445 A | 8/1993 | Hayhurst et al. |
| 5,268,001 A | 12/1993 | Nicholson et al. |
| 5,324,308 A | 6/1994 | Pierce |
| 5,330,442 A | 7/1994 | Green et al. |
| 5,336,240 A | 8/1994 | Metzler et al. |
| 5,354,298 A | 10/1994 | Lee et al. |
| 5,364,407 A | 11/1994 | Poll |
| 5,383,905 A | 1/1995 | Golds et al. |
| 5,405,352 A | 4/1995 | Weston |
| 5,411,523 A | 5/1995 | Goble |
| 5,417,712 A | 5/1995 | Whittaker et al. |
| 5,423,860 A | 6/1995 | Lizardi et al. |
| 5,464,427 A | 11/1995 | Curtis et al. |
| 5,472,452 A | 12/1995 | Trott |
| 5,480,403 A | 1/1996 | Lee et al. |
| 5,486,197 A | 1/1996 | Le et al. |
| 5,489,210 A | 2/1996 | Hanosh |
| 5,499,991 A | 3/1996 | Garman et al. |
| 5,501,683 A | 3/1996 | Trott |
| 5,501,692 A | 3/1996 | Riza |
| 5,501,695 A | 3/1996 | Anspach, Jr. et al. |
| 5,514,159 A | 5/1996 | Matula et al. |
| 5,522,844 A | 6/1996 | Johnson |
| 5,522,845 A | 6/1996 | Wenstrom, Jr. |
| 5,534,012 A | 7/1996 | Bonutti |
| 5,545,180 A | 8/1996 | Le et al. |
| 5,562,683 A | 10/1996 | Chan |
| 5,562,687 A | 10/1996 | Chan |
| 5,569,306 A | 10/1996 | Thal |
| 5,571,139 A | 11/1996 | Jenkins, Jr. |
| 5,584,835 A | 12/1996 | Greenfield |
| 5,601,557 A | 2/1997 | Hayhurst |
| 5,601,558 A | 2/1997 | Torrie et al. |
| 5,611,515 A | 3/1997 | Benderev et al. |
| 5,630,824 A | 5/1997 | Hart |
| 5,632,748 A | 5/1997 | Beck, Jr. et al. |
| 5,643,292 A | 7/1997 | Hart |
| 5,643,321 A | 7/1997 | McDevitt |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,681,320 A | 10/1997 | McGuire |
| 5,681,333 A | 10/1997 | Burkhart et al. |
| 5,683,419 A | 11/1997 | Thal |
| 5,690,649 A | 11/1997 | Li |
| 5,702,215 A | 12/1997 | Li |
| 5,702,397 A | 12/1997 | Goble et al. |
| 5,702,422 A | 12/1997 | Stone |
| 5,707,395 A | 1/1998 | Li |
| 5,709,708 A | 1/1998 | Thal |
| 5,713,903 A | 2/1998 | Sander et al. |
| 5,716,368 A | 2/1998 | de la Torrie et al. |
| 5,720,765 A | 2/1998 | Thal |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,746,752 A | 5/1998 | Burkhart |
| 5,746,753 A | 5/1998 | Sullivan et al. |
| 5,755,728 A | 5/1998 | Maki |
| 5,782,862 A | 7/1998 | Bonutti |
| 5,782,863 A | 7/1998 | Bartlett |
| 5,782,864 A | 7/1998 | Lizardi |
| 5,791,899 A | 8/1998 | Sachdeva et al. |
| 5,797,963 A | 8/1998 | McDevitt |
| 5,814,071 A | 9/1998 | McDevitt et al. |
| 5,814,072 A | 9/1998 | Bonutti |
| 5,814,073 A | 9/1998 | Bonutti |
| 5,843,127 A | 12/1998 | Li |
| 5,845,645 A | 12/1998 | Bonutti |
| 5,849,004 A | 12/1998 | Bramlet |
| 5,891,168 A | 4/1999 | Thal |
| 5,906,624 A | 5/1999 | Wenstrom, Jr. |
| 5,910,148 A | 6/1999 | Reimels et al. |
| 5,911,721 A | 6/1999 | Nicholson et al. |
| 5,928,244 A | 7/1999 | Tovey et al. |
| 5,935,129 A | 8/1999 | McDevitt et al. |
| 5,935,134 A | 8/1999 | Pedlick et al. |
| 5,935,149 A | 8/1999 | Ek |
| 5,948,000 A * | 9/1999 | Larsen ............ A61B 17/0469 606/232 |
| 5,948,001 A | 9/1999 | Larsen |
| 5,957,953 A | 9/1999 | DiPoto et al. |
| 5,968,044 A | 10/1999 | Nicholson et al. |
| 5,980,558 A | 11/1999 | Wiley |
| 5,980,559 A | 11/1999 | Bonutti |
| 5,993,459 A | 11/1999 | Larsen et al. |
| 6,010,514 A | 1/2000 | Burney et al. |

(56) References Cited

U.S. PATENT DOCUMENTS

| | | |
|---|---|---|
| 6,022,360 A | 2/2000 | Reimels et al. |
| 6,041,485 A | 3/2000 | Pedlick et al. |
| 6,045,573 A | 4/2000 | Wenstrom, Jr. et al. |
| 6,045,574 A | 4/2000 | Thal |
| 6,056,772 A | 5/2000 | Bonutti |
| 6,077,277 A | 6/2000 | Mollenauer et al. |
| 6,086,608 A | 7/2000 | Ek et al. |
| 6,099,538 A | 8/2000 | Moses et al. |
| 6,099,547 A | 8/2000 | Gellman et al. |
| 6,117,144 A | 9/2000 | Nobles et al. |
| 6,143,017 A | 11/2000 | Thal |
| 6,149,669 A | 11/2000 | Li |
| 6,159,234 A | 12/2000 | Bonutti et al. |
| 6,200,329 B1 | 3/2001 | Fung et al. |
| 6,221,107 B1 | 4/2001 | Steiner et al. |
| 6,231,592 B1 | 5/2001 | Bonutti et al. |
| 6,241,732 B1 | 6/2001 | Overaker et al. |
| 6,245,081 B1 | 6/2001 | Bowman et al. |
| 6,245,082 B1 | 6/2001 | Gellman et al. |
| 6,312,448 B1 | 11/2001 | Bonutti |
| 6,319,252 B1 | 11/2001 | McDevitt et al. |
| 6,319,269 B1 | 11/2001 | Li |
| 6,475,230 B1 | 11/2002 | Bonutti et al. |
| RE37,963 E | 1/2003 | Thal |
| 6,506,190 B1 | 1/2003 | Walshe |
| 6,517,579 B1 | 2/2003 | Paulos et al. |
| 6,520,980 B1 | 2/2003 | Foerster |
| 6,524,316 B1 | 2/2003 | Nicholson et al. |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,547,800 B2 | 4/2003 | Foerster et al. |
| 6,547,807 B2 | 4/2003 | Chan et al. |
| 6,562,071 B2 | 5/2003 | Järvinen |
| 6,575,976 B2 | 6/2003 | Grafton |
| 6,575,987 B2 | 6/2003 | Gellman et al. |
| 6,582,453 B1 | 6/2003 | Tran et al. |
| 6,585,730 B1 | 7/2003 | Foerster |
| 6,620,166 B1 | 9/2003 | Wenstrom, Jr. et al. |
| 6,629,984 B1 | 10/2003 | Chan |
| 6,641,596 B1 | 11/2003 | Lizardi |
| 6,641,597 B2 | 11/2003 | Burkhart et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,692,516 B2 | 2/2004 | West, Jr. et al. |
| 6,733,506 B1 | 5/2004 | McDevitt et al. |
| 6,746,457 B2 | 6/2004 | Dana et al. |
| 6,752,814 B2 | 6/2004 | Gellman et al. |
| 6,770,073 B2 | 8/2004 | McDevitt et al. |
| 6,770,076 B2 | 8/2004 | Foerster |
| 6,780,198 B1 | 8/2004 | Gregoire et al. |
| 6,814,741 B2 | 11/2004 | Bowman et al. |
| 6,855,157 B2 | 2/2005 | Foerster et al. |
| 6,887,259 B2 | 5/2005 | Lizardi |
| 6,932,834 B2 | 8/2005 | Lizardi et al. |
| 6,942,666 B2 | 9/2005 | Overaker et al. |
| 6,986,781 B2 | 1/2006 | Smith |
| 6,991,636 B2 | 1/2006 | Rose |
| 7,033,380 B2 | 4/2006 | Schwartz et al. |
| 7,037,324 B2 | 5/2006 | Martinek |
| 7,041,120 B2 | 5/2006 | Li et al. |
| 7,048,755 B2 | 5/2006 | Bonutti et al. |
| 7,074,203 B1 | 7/2006 | Johanson et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,144,415 B2 | 12/2006 | Del Rio et al. |
| 7,160,314 B2 | 1/2007 | Sgro et al. |
| 7,226,469 B2 | 6/2007 | Benavitz et al. |
| 7,235,100 B2 | 6/2007 | Martinek |
| 7,309,346 B2 | 12/2007 | Martinek |
| 7,329,272 B2 | 2/2008 | Burkhart et al. |
| 7,381,213 B2 | 6/2008 | Lizardi |
| 7,507,200 B2 | 3/2009 | Okada |
| 7,517,357 B2 | 4/2009 | Abrams et al. |
| 7,556,640 B2 | 7/2009 | Foerster |
| 7,637,926 B2 | 12/2009 | Foerster et al. |
| 7,662,171 B2 | 2/2010 | West, Jr. et al. |
| 7,674,274 B2 | 3/2010 | Foerster et al. |
| 7,674,276 B2 | 3/2010 | Stone et al. |
| 7,682,374 B2 | 3/2010 | Foerster et al. |
| 7,695,494 B2 | 4/2010 | Foerster |
| 7,704,262 B2 | 4/2010 | Bellafiore et al. |
| 7,713,286 B2 | 5/2010 | Singhatat |
| 7,780,701 B1 | 8/2010 | Meridew et al. |
| 7,794,484 B2 | 9/2010 | Stone et al. |
| 7,828,820 B2 | 11/2010 | Stone et al. |
| 7,837,710 B2 | 11/2010 | Lombardo et al. |
| 7,842,050 B2 | 11/2010 | Diduch et al. |
| 7,846,167 B2 | 12/2010 | Garcia et al. |
| 7,867,264 B2 | 1/2011 | McDevitt et al. |
| 7,896,907 B2 | 3/2011 | McDevitt et al. |
| 7,938,847 B2 | 5/2011 | Fanton et al. |
| 7,963,972 B2 | 6/2011 | Foerster et al. |
| 7,976,565 B1 | 7/2011 | Meridew |
| 7,993,369 B2 | 8/2011 | Dreyfuss |
| 8,029,537 B2 | 10/2011 | West, Jr. et al. |
| 8,057,524 B2 | 11/2011 | Meridew |
| 8,066,718 B2 | 11/2011 | Weisel et al. |
| 8,075,572 B2 | 12/2011 | Stefanchik et al. |
| RE43,143 E | 1/2012 | Hayhurst |
| 8,100,942 B1 | 1/2012 | Green et al. |
| 8,109,969 B1 | 2/2012 | Green et al. |
| 8,118,835 B2 | 2/2012 | Weisel et al. |
| 8,128,641 B2 | 3/2012 | Wardle |
| 8,133,258 B2 | 3/2012 | Foerster et al. |
| 8,137,381 B2 | 3/2012 | Foerster et al. |
| 8,137,383 B2 | 3/2012 | West, Jr. et al. |
| 8,162,978 B2 | 4/2012 | Lombardo et al. |
| 8,298,291 B2 | 10/2012 | Ewers et al. |
| 8,409,252 B2 | 4/2013 | Lombardo et al. |
| 8,435,264 B2 | 5/2013 | Sojka et al. |
| 8,444,672 B2 | 5/2013 | Foerster |
| 8,444,674 B2 | 5/2013 | Kaplan |
| 8,454,704 B2 | 6/2013 | Frushell et al. |
| 8,460,340 B2 | 6/2013 | Sojka et al. |
| 8,469,998 B2 | 6/2013 | Sojka et al. |
| 8,491,600 B2 | 7/2013 | McDevitt et al. |
| 8,523,902 B2 | 9/2013 | Heaven et al. |
| 8,545,535 B2 | 10/2013 | Hirotsuka et al. |
| 8,545,536 B2 | 10/2013 | Mayer et al. |
| 8,613,756 B2 | 12/2013 | Lizardi et al. |
| 8,632,568 B2 | 1/2014 | Miller et al. |
| 8,834,543 B2 | 9/2014 | McDevitt et al. |
| 8,986,345 B2 | 3/2015 | Denham et al. |
| 2001/0002436 A1 | 5/2001 | Bowman et al. |
| 2001/0049529 A1 | 12/2001 | Cachia et al. |
| 2002/0040241 A1 | 4/2002 | Jarvinen |
| 2002/0115999 A1 | 8/2002 | McDevitt et al. |
| 2002/0147456 A1 | 10/2002 | Diduch et al. |
| 2003/0004545 A1 | 1/2003 | Burkhart et al. |
| 2003/0065361 A1 | 4/2003 | Dreyfuss |
| 2003/0139752 A1 | 7/2003 | Pasricha et al. |
| 2003/0195563 A1 | 10/2003 | Foerster |
| 2003/0195564 A1 | 10/2003 | Tran et al. |
| 2004/0093031 A1 | 5/2004 | Burkhart et al. |
| 2004/0138706 A1 | 7/2004 | Abrams et al. |
| 2004/0220573 A1 | 11/2004 | McDevitt et al. |
| 2004/0249393 A1 | 12/2004 | Weisel et al. |
| 2005/0004644 A1 | 1/2005 | Kelsch et al. |
| 2005/0049592 A1 | 3/2005 | Keith et al. |
| 2005/0075668 A1 | 4/2005 | Lizardi |
| 2005/0149122 A1 | 7/2005 | McDevitt et al. |
| 2005/0245932 A1 | 11/2005 | Fanton et al. |
| 2005/0277986 A1 | 12/2005 | Foerster et al. |
| 2005/0283171 A1 | 12/2005 | Bellafiore et al. |
| 2006/0052788 A1 | 3/2006 | Thelen et al. |
| 2006/0079904 A1 | 4/2006 | Thal |
| 2006/0081553 A1 | 4/2006 | Patterson et al. |
| 2006/0106423 A1 | 5/2006 | Weisel et al. |
| 2006/0217762 A1 | 9/2006 | Maahs et al. |
| 2006/0235413 A1* | 10/2006 | Denham ............ A61B 17/0401 606/232 |

(56) References Cited

U.S. PATENT DOCUMENTS

| | | |
|---|---|---|
| 2006/0265010 A1 | 11/2006 | Paraschac et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2007/0005068 A1 | 1/2007 | Sklar |
| 2007/0060922 A1 | 3/2007 | Dreyfuss |
| 2007/0093858 A1 | 4/2007 | Gambale et al. |
| 2007/0142835 A1 | 6/2007 | Green et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0203498 A1 | 8/2007 | Gerber et al. |
| 2007/0219557 A1 | 9/2007 | Bourque et al. |
| 2007/0255317 A1 | 11/2007 | Fanton et al. |
| 2007/0260259 A1 | 11/2007 | Fanton et al. |
| 2007/0270889 A1 | 11/2007 | Conlon et al. |
| 2007/0270907 A1 | 11/2007 | Stokes et al. |
| 2007/0288027 A1 | 12/2007 | Grafton et al. |
| 2008/0033460 A1 | 2/2008 | Ziniti et al. |
| 2008/0086138 A1 | 4/2008 | Stone et al. |
| 2008/0275469 A1 | 11/2008 | Fanton et al. |
| 2008/0294177 A1 | 11/2008 | To et al. |
| 2008/0306510 A1 | 12/2008 | Stchur |
| 2009/0018554 A1 | 1/2009 | Thorne et al. |
| 2009/0082807 A1 | 3/2009 | Miller et al. |
| 2009/0099598 A1 | 4/2009 | McDevitt et al. |
| 2009/0112214 A1 | 4/2009 | Philippon et al. |
| 2009/0192545 A1 | 7/2009 | Workman |
| 2009/0222041 A1 | 9/2009 | Foerster |
| 2009/0248068 A1 | 10/2009 | Lombardo et al. |
| 2009/0292321 A1 | 11/2009 | Collette |
| 2009/0299386 A1 | 12/2009 | Meridew |
| 2009/0306711 A1 | 12/2009 | Stone et al. |
| 2009/0312794 A1 | 12/2009 | Nason et al. |
| 2010/0004683 A1 | 1/2010 | Hoof et al. |
| 2010/0049213 A1 | 2/2010 | Serina et al. |
| 2010/0063542 A1 | 3/2010 | van der Burg et al. |
| 2010/0069925 A1 | 3/2010 | Friedman et al. |
| 2010/0094314 A1 | 4/2010 | Hernlund et al. |
| 2010/0094355 A1 | 4/2010 | Trenhaile |
| 2010/0094425 A1 | 4/2010 | Bentley et al. |
| 2010/0100127 A1 | 4/2010 | Trenhaile |
| 2010/0114162 A1 | 5/2010 | Bojarski et al. |
| 2010/0121348 A1 | 5/2010 | van der Burg et al. |
| 2010/0121349 A1 | 5/2010 | Meier et al. |
| 2010/0191283 A1 | 7/2010 | Foerster et al. |
| 2010/0198258 A1 | 8/2010 | Heaven et al. |
| 2010/0222812 A1 | 9/2010 | Stone et al. |
| 2010/0251861 A1 | 10/2010 | Sixto, Jr. et al. |
| 2010/0292731 A1 | 11/2010 | Gittings et al. |
| 2010/0305576 A1 | 12/2010 | Ferguson et al. |
| 2011/0015674 A1 | 1/2011 | Howard et al. |
| 2011/0046682 A1 | 2/2011 | Stephan et al. |
| 2011/0071545 A1 | 3/2011 | Pamichev et al. |
| 2011/0071549 A1 | 3/2011 | Caborn et al. |
| 2011/0098728 A1 | 4/2011 | McDevitt et al. |
| 2011/0152929 A1 | 6/2011 | McDevitt et al. |
| 2011/0224726 A1 | 9/2011 | Lombardo et al. |
| 2011/0238113 A1 | 9/2011 | Fanton et al. |
| 2011/0264140 A1 | 10/2011 | Lizardi et al. |
| 2011/0295279 A1 | 12/2011 | Stone et al. |
| 2011/0301621 A1 | 12/2011 | Oren et al. |
| 2011/0301622 A1 | 12/2011 | Oren et al. |
| 2012/0041485 A1 | 2/2012 | Kaiser et al. |
| 2012/0053629 A1 | 3/2012 | Reiser et al. |
| 2012/0059417 A1 | 3/2012 | Norton et al. |
| 2012/0143221 A1 | 6/2012 | Weisel et al. |
| 2012/0150223 A1 | 6/2012 | Manos et al. |
| 2013/0006276 A1 | 1/2013 | Lantz et al. |
| 2013/0023930 A1 | 1/2013 | Stone et al. |
| 2013/0096611 A1 | 4/2013 | Sullivan |
| 2013/0103083 A1 | 4/2013 | Baird |
| 2013/0138152 A1 | 5/2013 | Stone et al. |
| 2013/0144334 A1 | 6/2013 | Bouduban et al. |
| 2013/0144338 A1 | 6/2013 | Stone et al. |
| 2013/0184748 A1 | 7/2013 | Sojka et al. |
| 2013/0204298 A1 | 8/2013 | Graul et al. |
| 2013/0267998 A1 | 10/2013 | Vijay et al. |
| 2013/0296931 A1 | 11/2013 | Sengun |
| 2014/0249579 A1 | 9/2014 | Heaven et al. |
| 2014/0257382 A1 | 9/2014 | McCartney |
| 2014/0316460 A1 | 10/2014 | Graul et al. |
| 2015/0100087 A1 | 4/2015 | Graul et al. |

FOREIGN PATENT DOCUMENTS

| | | |
|---|---|---|
| EP | 0 251 583 | 1/1988 |
| EP | 0 270 704 | 6/1988 |
| EP | 0 318 426 | 5/1989 |
| EP | 0 575 707 | 12/1993 |
| EP | 0 673 624 | 9/1995 |
| EP | 0 834 281 | 4/1998 |
| EP | 1 016 377 | 7/2000 |
| EP | 1 568 327 | 8/2005 |
| EP | 1 762 187 | 3/2007 |
| EP | 1 825 817 | 8/2007 |
| EP | 2 335 603 | 6/2011 |
| WO | WO 92/04874 | 4/1992 |
| WO | WO 95/15726 | 6/1995 |
| WO | WO 97/03615 | 2/1997 |
| WO | WO 97/30649 | 8/1997 |
| WO | WO 98/38938 | 9/1998 |
| WO | WO 2008/063915 | 5/2008 |
| WO | WO 2011/060022 | 5/2011 |
| WO | WO 2012/034131 | 3/2012 |

* cited by examiner

CAM-TYPE FEMOROACETABULAR IMPINGEMENT (FAI)
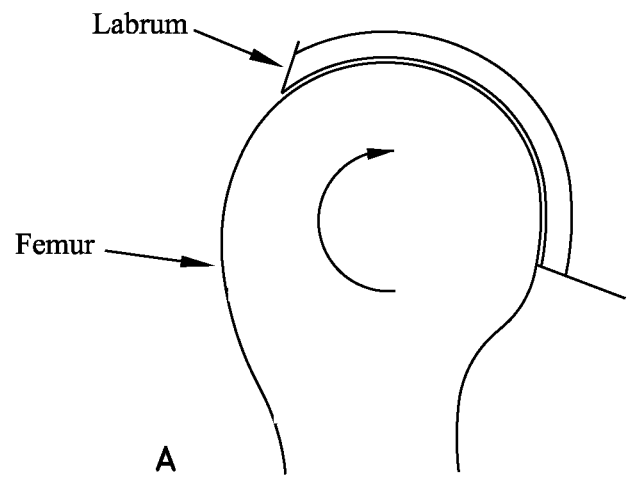
CAM INJURY TO THE LABRUM
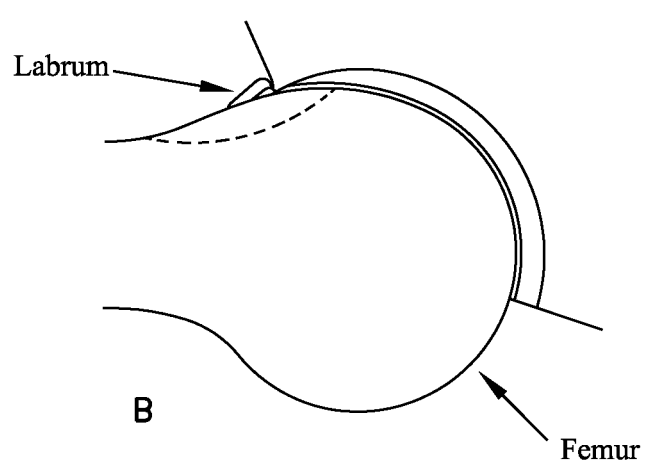
FIG. 13

PINCER-TYPE FEMOROACETABULAR IMPINGEMENT (FAI)
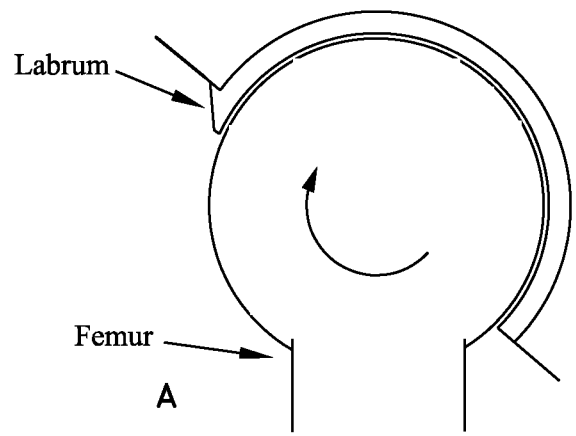
PINCER INJURY TO THE LABRUM
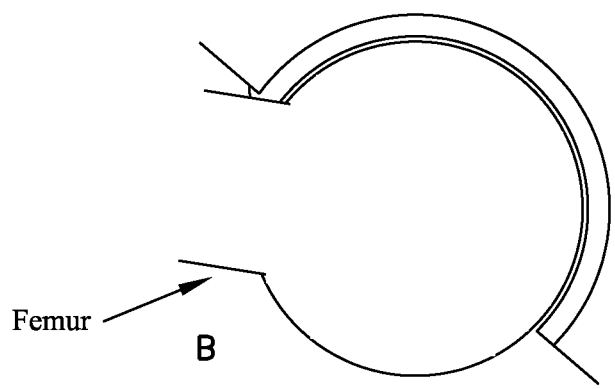
FIG. 14

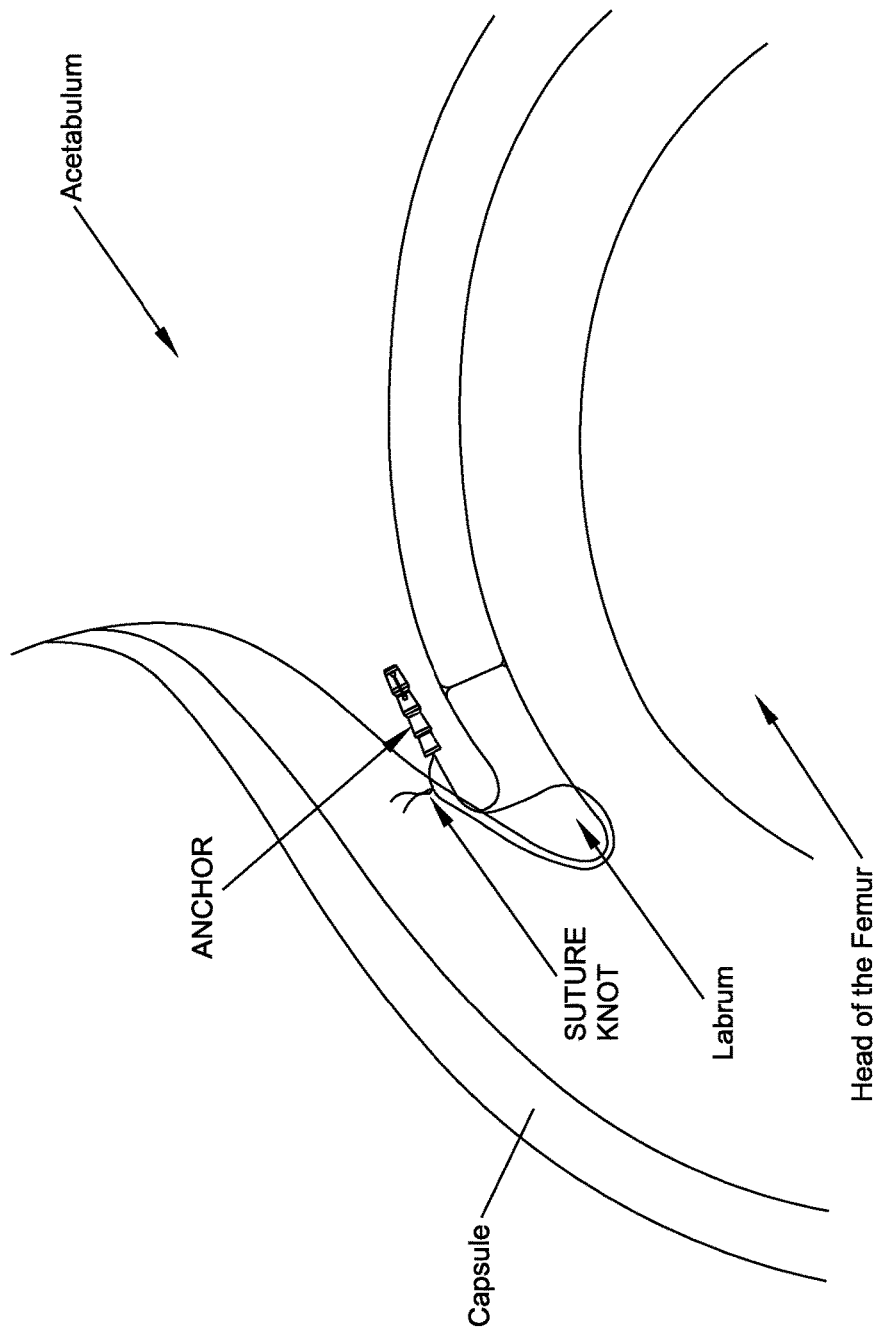

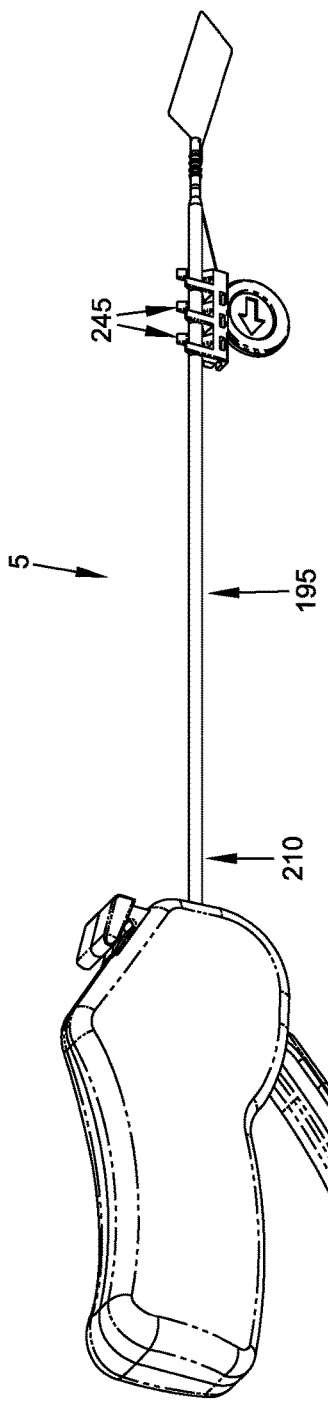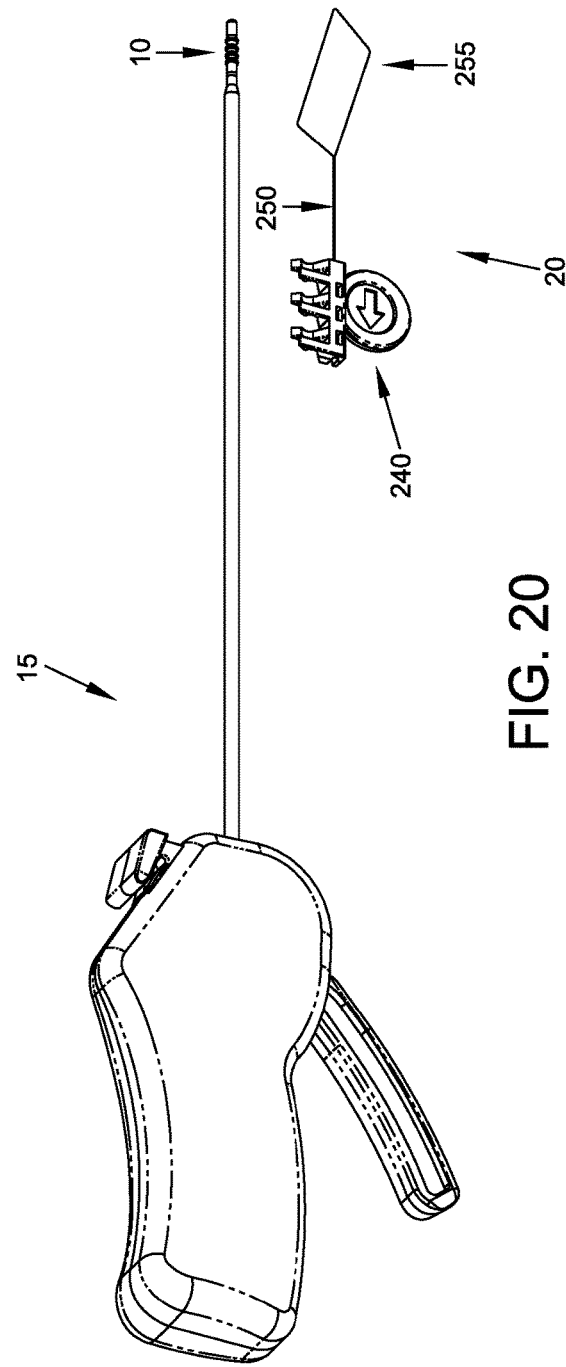

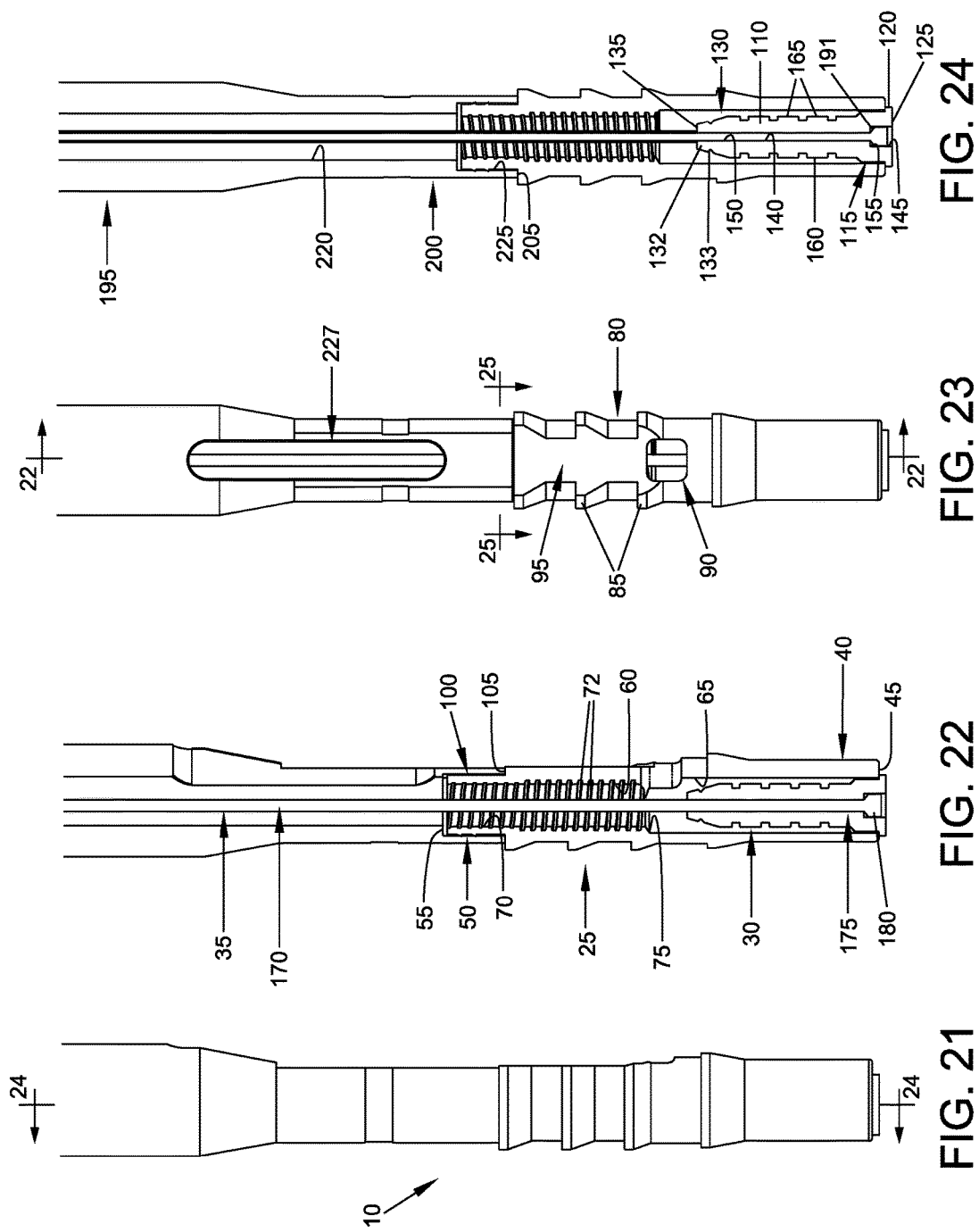

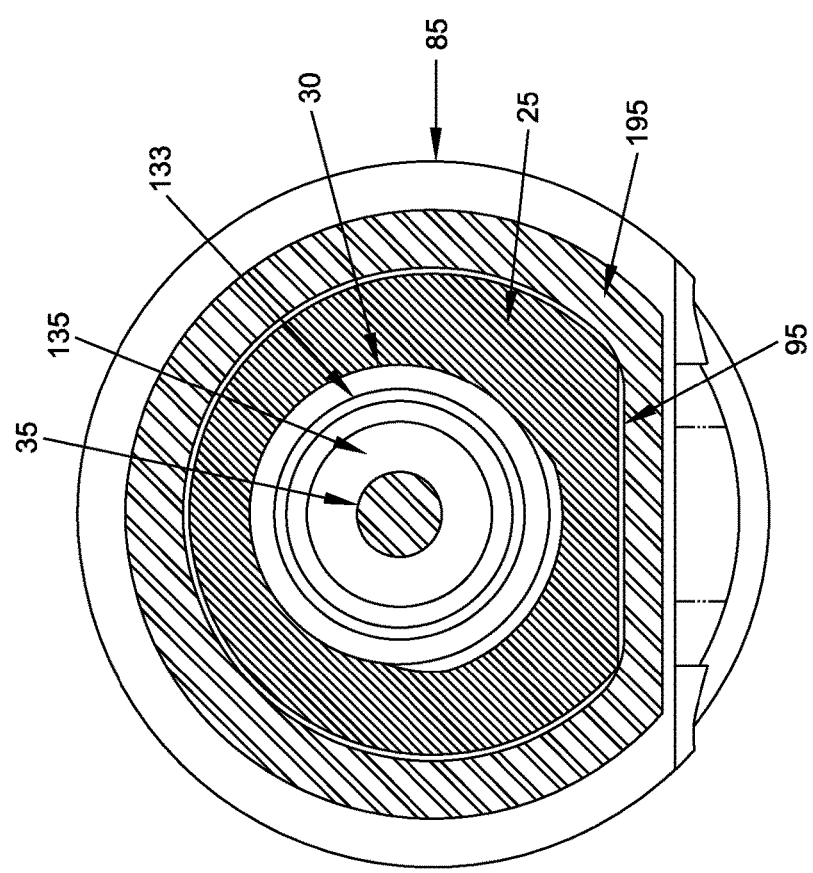

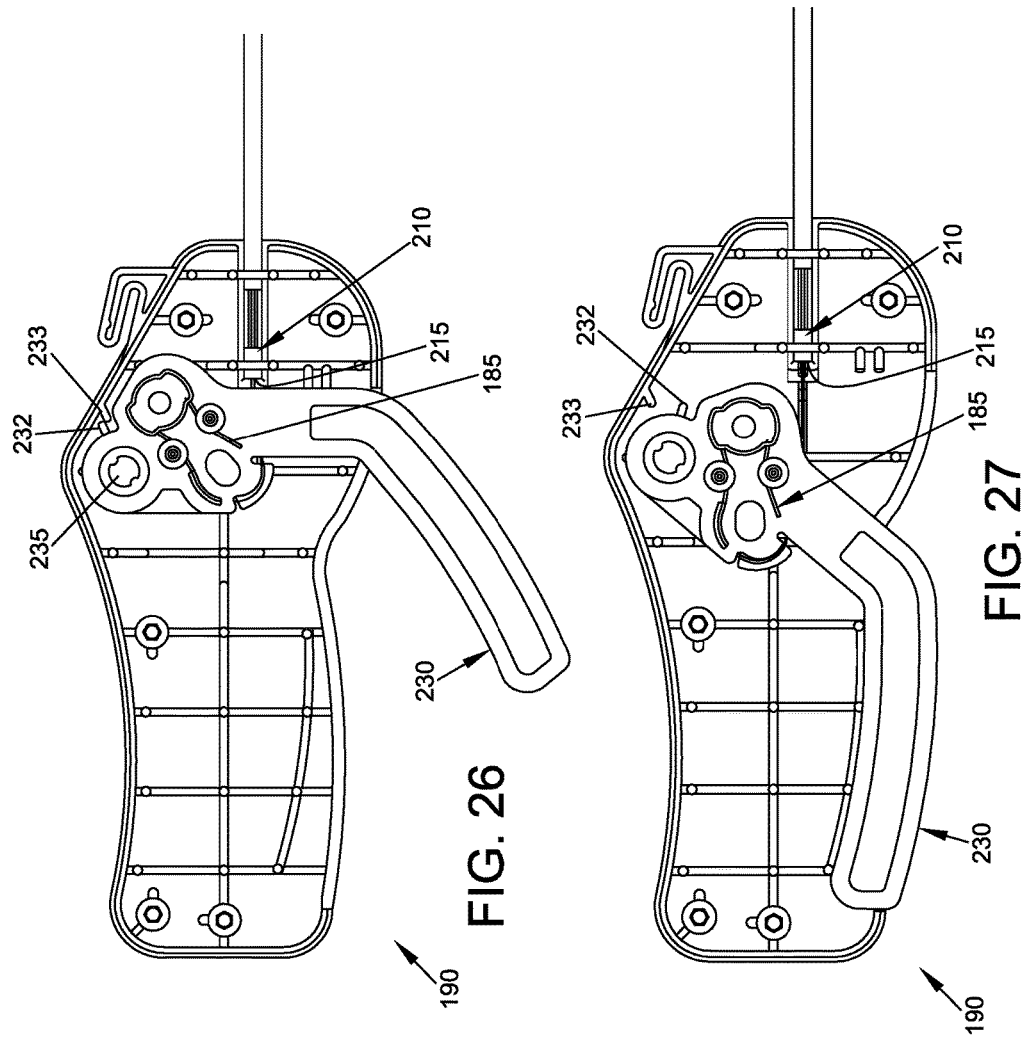

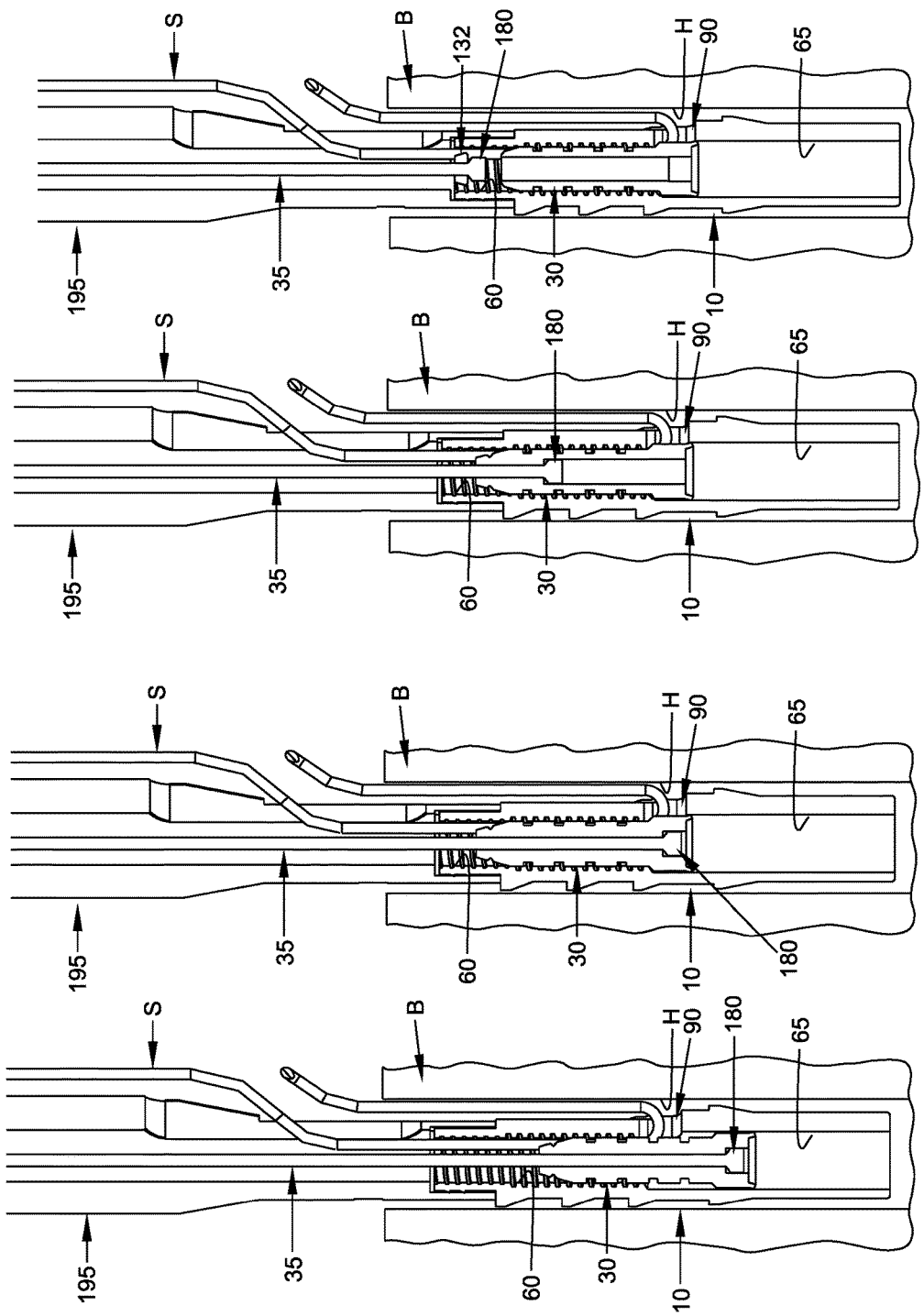

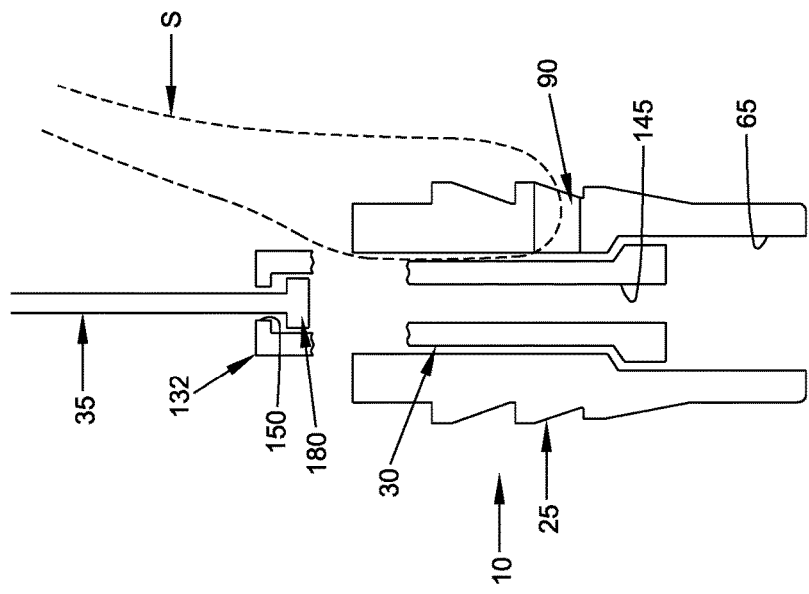
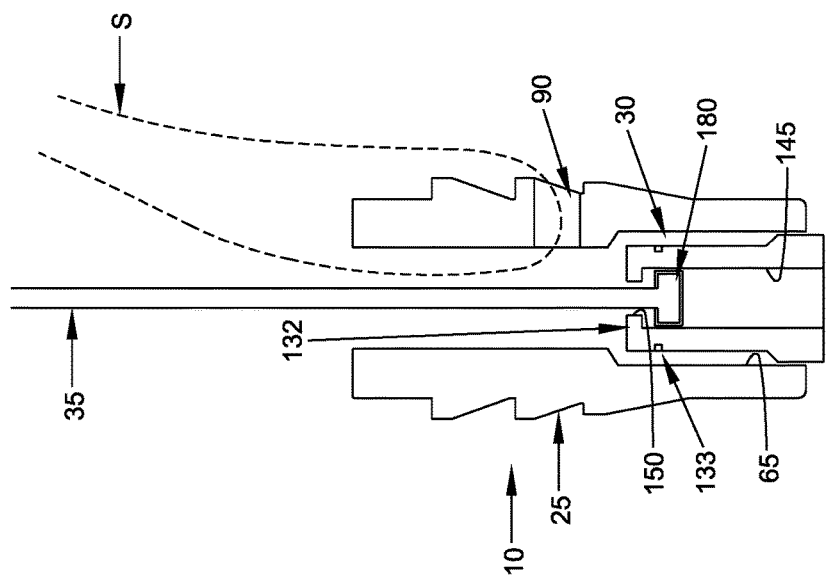

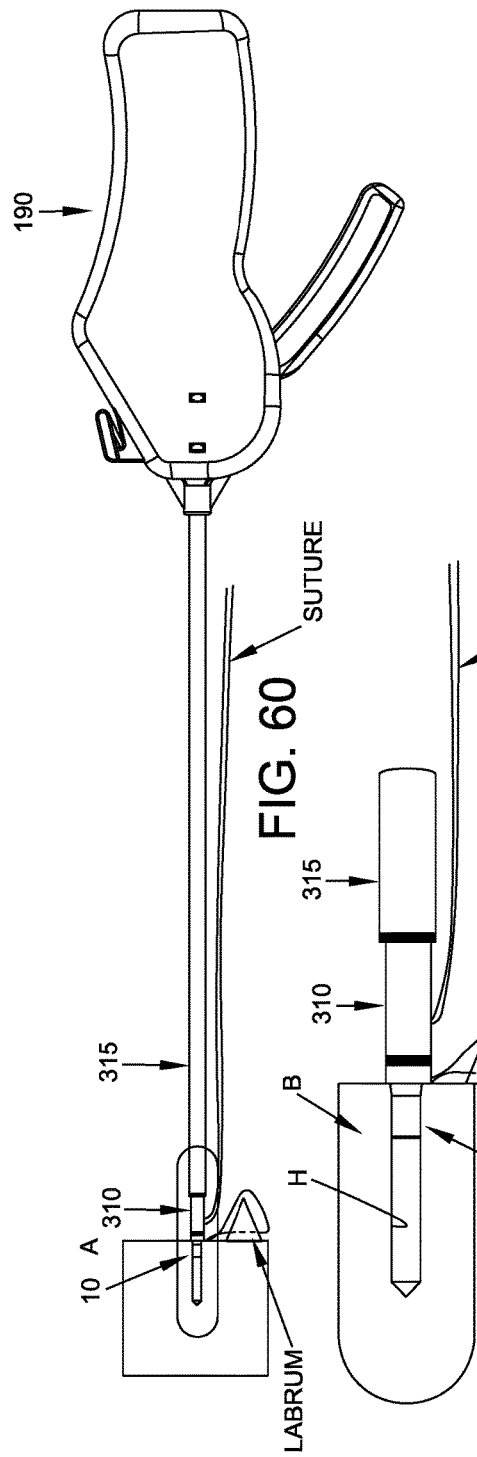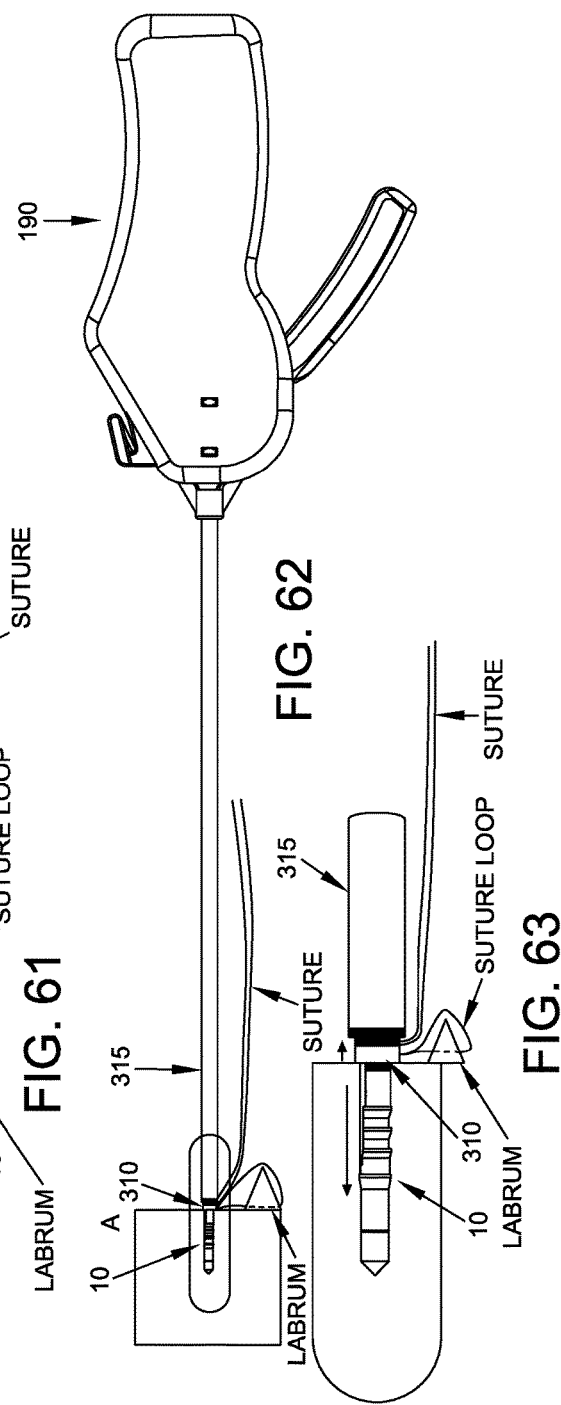

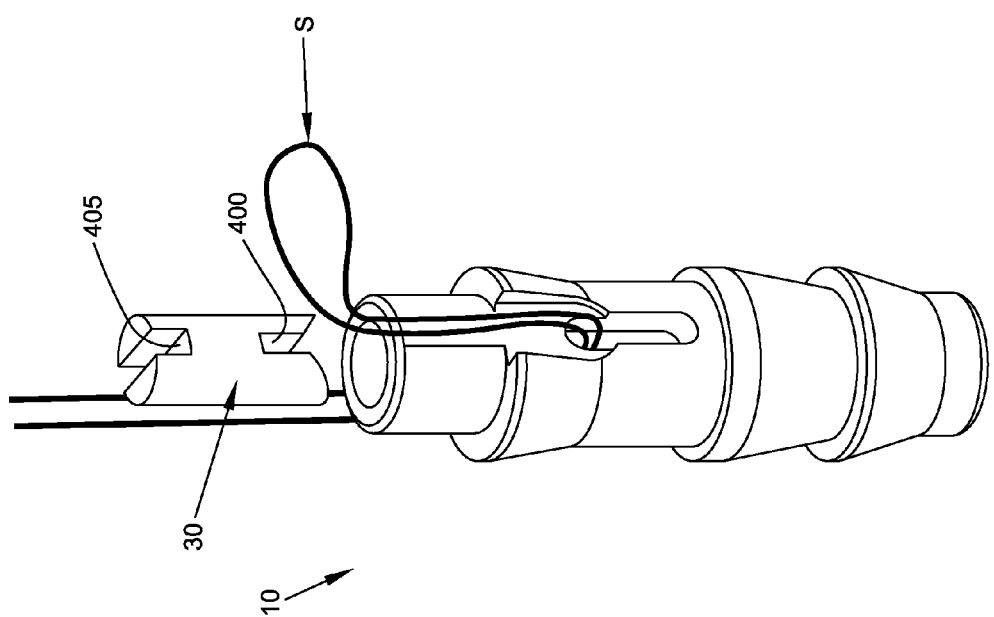

METHOD AND APPARATUS FOR ATTACHING TISSUE TO BONE, INCLUDING THE PROVISION AND USE OF A NOVEL KNOTLESS SUTURE ANCHOR SYSTEM, INCLUDING A RETRACTABLE SHEATH

REFERENCE TO PENDING PRIOR PATENT APPLICATIONS

This patent application:
(1) is a continuation-in-part of pending prior U.S. patent application Ser. No. 14/876,091, filed Oct. 6, 2015 by Pivot Medical, Inc. and Jeremy Graul et al. for METHOD AND APPARATUS FOR ATTACHING TISSUE TO BONE, INCLUDING THE PROVISION AND USE OF A NOVEL KNOTLESS SUTURE ANCHOR SYSTEM, which patent application in turn:
  (A) is a continuation of prior U.S. patent application Ser. No. 13/830,501, filed Mar. 14, 2013 by Pivot Medical, Inc. and Jeremy Graul et al. for METHOD AND APPARATUS FOR ATTACHING TISSUE TO BONE, INCLUDING THE PROVISION AND USE OF A NOVEL KNOTLESS SUTURE ANCHOR SYSTEM, which patent application in turn:
    (i) is a continuation-in-part of pending prior U.S. patent application Ser. No. 13/642,168, filed Dec. 26, 2012 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which patent application in turn claims benefit of:
      (a) prior International (PCT) Patent Application No. PCT/US2011/021173, filed Jan. 13, 2011 by Pivot Medical, Inc. and Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn claims benefit of:
        (i) prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM; and
        (ii) pending prior U.S. patent application Ser. No. 12/839,246, filed Jul. 19, 2010 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn claims benefit of:
          (1) prior U.S. Provisional Patent Application Ser. No. 61/271,205, filed Jul. 17, 2009 by Chris Pamichev et al. for METHOD AND APPARATUS FOR RE-SECURING THE LABRUM TO THE ACETABULUM, INCLUDING THE PROVISION AND USE OF A NOVEL NANO TACK SYSTEM; and
          (2) prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM;
    (ii) is a continuation-in-part of prior U.S. patent application Ser. No. 13/538,378, filed Jun. 29, 2012 by Andrew Lantz et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which patent application in turn:
      (a) claims benefit of prior U.S. Provisional Patent Application Ser. No. 61/502,621, filed Jun. 29, 2011 by Andrew Lantz et al. for FORCE-LIMITING (FORCE-CONTROLLING) DELIVERY MECHANISMS FOR THE CONTROLLED DELIVERY OF THE SUTURE ANCHOR; and
      (iii) claims benefit of prior U.S. Provisional Patent Application Ser. No. 61/644,129, filed May 8, 2012 by Jeremy Graul et al. for METHOD AND APPARATUS FOR RE-ATTACHING THE LABRUM TO THE ACETABULUM, INCLUDING THE PROVISION AND USE OF A NOVEL SUTURE ANCHOR SYSTEM; and
      (iv) claims benefit of prior U.S. Provisional Patent Application Ser. No. 61/718,997, filed Oct. 26, 2012 by Pivot Medical, Inc. and Jeremy Graul et al. for METHOD AND APPARATUS FOR RE-ATTACHING THE LABRUM TO THE ACETABULUM, INCLUDING THE PROVISION AND USE OF A NOVEL SUTURE ANCHOR SYSTEM; and
(2) claims benefit of prior U.S. Provisional Patent Application Ser. No. 62/064,194, filed Oct. 15, 2014 by Pivot Medical, Inc. and Jeremy Graul et al. for METHOD AND APPARATUS FOR ATTACHING TISSUE TO BONE, INCLUDING THE PROVISION AND USE OF A NOVEL KNOTLESS SUTURE ANCHOR SYSTEM, INCLUDING A RETRACTABLE SHEATH.

The twelve (12) above-identified patent applications are hereby incorporated herein by reference.

FIELD OF THE INVENTION

This invention relates to surgical methods and apparatus in general, and more particularly to surgical methods and apparatus for treating a hip joint and other anatomy.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the torso. More particularly, and looking now at FIG. 2, the head of the femur is received in the acetabular cup of the hip, with a plurality of ligaments and other soft tissue serving to hold the bones in articulating relation.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of labral injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require large incisions into the interior of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and hence less common in practice. Consequently, many patients are forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Re-Attaching the Labrum of the Hip Joint

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to the repair of a torn and/or detached labrum. This procedure may be attempted when the labrum has been damaged but is still sufficiently healthy and capable of repair. The repair can occur with a labrum which is still attached to the acetabulum or after the labrum has been deliberately detached from the acetabulum (e.g., so as to allow for acetabular rim trimming to treat a pathology such as a pincer-type FAI) and needs to be subsequently re-attached. See, for example, FIG. 16, which shows a normal labrum which has its base securely attached to the acetabulum, and FIG. 17, which shows a portion of the labrum (in this case the tip) detached from the acetabulum. In this respect it should also be appreciated that repairing the labrum rather than removing the labrum is generally desirable, inasmuch as studies have shown that patients whose labrum has been repaired tend to have better long-term outcomes than patients whose labrum has been removed.

Unfortunately, current methods and apparatus for arthroscopically repairing (e.g., re-attaching) the labrum are somewhat problematic. The present invention is intended to improve upon the current approaches for labrum repair.

More particularly, current approaches for arthroscopically repairing the labrum typically use apparatus originally designed for use in re-attaching ligaments to bone. For example, one such approach utilizes a screw-type anchor, with two lengths of suture extending therefrom, and involves deploying the anchor in the acetabulum above the labrum re-attachment site. After the anchor has been deployed, one length of suture is passed either through the detached labrum or, alternatively, around the detached labrum. Then that length of suture is tied to the other length of suture so as to secure the labrum against the acetabular rim. See FIG. 18.

Unfortunately, suture anchors of the sort described above are traditionally used for re-attaching ligaments to bone and, as a result, tend to be relatively large, since they must carry the substantial pull-out forces normally associated with ligament reconstruction. However, this large anchor size is generally unnecessary for labrum re-attachment, since the labrum is not subjected to substantial forces, and the large anchor size typically causes unnecessary trauma to the patient.

Furthermore, the large size of traditional suture anchors can be problematic when the anchors are used for labrum re-attachment, since the suture anchors generally require a substantial bone mass for secure anchoring, and such a large bone mass is generally available only a substantial distance up the acetabular shelf. In addition, the large size of the suture anchors generally makes it necessary to set the suture anchor a substantial distance up the acetabular shelf, in order to ensure that the distal tip of the suture anchor does not inadvertently break through the acetabular shelf and contact the articulating surfaces of the joint. However, labral re-attachment utilizing a suture anchor set high up into the acetabular shelf creates a suture path, and hence a labral draw force, which is not directly aligned with the portion of the acetabular rim where the labrum is to be re-attached. As a result, an "indirect" draw force (also known as "eversion") is typically applied to the labrum, i.e., the labrum is drawn around the rim of the acetabulum rather than directly into the acetabulum. See FIG. 18. This can sometimes result in a problematic labral re-attachment and, ultimately, can lead to a loss of the suction seal between the labrum and femoral head, which is a desired outcome of the labral re-attachment procedure. Using suture anchors of a smaller size allows the suture anchor to be set closer to the rim of the acetabulum, which can help reduce this effect. See FIG. 18A.

In addition to the foregoing, suture anchors of the sort described above require that a knot be tied at the surgical site in order to secure the labrum to the acetabulum. This can be time-consuming and inconvenient to effect. More particularly, and as noted above, the suture anchor typically has a suture connected thereto so that two lengths of suture extend from the suture anchor and are available to secure the labrum to the acetabulum (which receives the suture anchor). One or both of the two lengths of suture are passed through or around the labrum and then knotted to one another so as to secure the labrum to the acetabulum. However, it can be time-consuming and inconvenient to form the knot at the surgical site, given the limited access to the surgical site and the restricted work space at the surgical site.

Accordingly, a new approach is needed for arthroscopically re-attaching the labrum to the acetabulum.

SUMMARY OF THE INVENTION

The present invention provides a novel method and apparatus for re-attaching the labrum to the acetabulum.

Among other things, the present invention provides a novel knotless suture anchor system which may be used to re-attach the labrum to the acetabulum, and/or to attach other tissue to bone.

In one preferred form of the present invention, there is provided a knotless suture anchor wherein a loop of suture is passed through the labrum (or other tissue) and its two free ends are slidably connected (e.g., slidably threaded through) the knotless suture anchor. After the knotless suture anchor is advanced into the acetabulum (or other bone) and the loop of suture is tensioned so as to hold the labrum (or other tissue) in place against the acetabulum (or other bone), the knotless suture anchor is reconfigured so as to lock the loop of suture to the knotless suture anchor and hence secure the labrum (or other tissue) to the acetabulum (or other bone).

In one form of the present invention, there is provided apparatus for securing a first object to a second object, the apparatus comprising:

an elongated body having a distal end, a proximal end, and a lumen extending between the distal end and the proximal end, the lumen comprising a distal section and a proximal section, the distal section of the lumen having a wider diameter than the proximal section of the lumen;

a window extending through the side wall of the elongated body and communicating with the lumen, the window being disposed in the vicinity of the intersection between the distal section of the lumen and the proximal section of the lumen and being sized to receive a first object therein;

an elongated element extending through the lumen of the elongated body, the elongated element comprising a proximal end and a distal end; and a locking element mounted to the distal end of the elongated element and disposed in the distal section of the lumen;

whereby, when the elongated body is disposed in a second object, and a first object extends through the window, and the locking element is thereafter moved proximally, proximal movement of the locking element causes the elongated body to capture the first object to the elongated body, whereby to secure the first object to the second object.

In another form of the present invention, there is provided apparatus for securing a first object to a second object, the apparatus comprising:

an elongated body having a distal end, a proximal end, and a lumen extending between the distal end and the proximal end;

a window extending through the side wall of the elongated body and communicating with the lumen, the window being sized to receive a first object therein;

a locking element disposed in the lumen, the locking element having a larger proximal end and a smaller distal end;

whereby, when the elongated body is disposed in a second object, and a first object extends through the window, and the locking element is thereafter moved distally, distal movement of the locking element captures the first object to the elongated body, whereby to secure the first object to the second object.

In another form of the present invention, there is provided a method for securing a first object to a second object, the method comprising:

providing apparatus comprising:
an elongated body having a distal end, a proximal end, and a lumen extending between the distal end and the proximal end, the lumen comprising a distal section and a proximal section, the distal section of the lumen having a wider diameter than the proximal section of the lumen;
a window extending through the side wall of the elongated body and communicating with the lumen, the window being disposed in the vicinity of the intersection between the distal section of the lumen and the proximal section of the lumen and being sized to receive a first object therein;
an elongated element extending through the lumen of the elongated body, the elongated element comprising a proximal end and a distal end; and
a locking element mounted to the distal end of the elongated element and disposed in the distal section of the lumen;

extending the first object through the window;
positioning the elongated body in the second object; and
moving the locking element proximally, such that proximal movement of the locking element causes the elongated body to capture the first object to the elongated body, whereby to secure the first object to the second object.

In another form of the present invention, there is provided a method for securing a first object to a second object, the method comprising:

providing apparatus comprising:
an elongated body having a distal end, a proximal end, and a lumen extending between the distal end and the proximal end;
a window extending through the side wall of the elongated body and communicating with the lumen, the window being sized to receive a first object therein;
a locking element mounted to the distal end of the elongated element and disposed in the lumen, the locking element having a larger proximal end and a smaller distal end;

extending the first object extends through the window;
positioning the elongated body in the second object; and
moving the locking element distally, such that distal movement of the locking element captures the first object to the elongated body, whereby to secure the first object to the second object.

In another form of the present invention, there is provided apparatus for securing a first object to a second object, the apparatus comprising:

an anchor, the anchor comprising:
an elongated body having a distal end, a proximal end, and a lumen extending between the distal end and the proximal end, the lumen comprising a distal section and a proximal section, the distal section of the lumen having a wider diameter than the proximal section of the lumen;
a window extending through the side wall of the elongated body and communicating with the lumen, the window being disposed in the vicinity of the intersection between the distal section of the lumen and the proximal section of the lumen and being sized to receive a first object therein;
an elongated element extending through the lumen of the elongated body, the elongated element comprising a proximal end and a distal end; and
a locking element mounted to the distal end of the elongated element and disposed in the distal section of the lumen;
whereby, when the elongated body is disposed in a second object, and a first object extends through the window, and the locking element is thereafter moved proximally, proximal movement of the locking element causes the elongated body to capture the first object to the elongated body, whereby to secure the first object to the second object; and
an inserter, the inserter comprising:
a handle;
a shaft having a distal end and a proximal end, with a lumen extending therebetween, the proximal end of the shaft being mounted to the handle and the distal end of the shaft being configured to releasably engage the elongated body;
a retractable sheath disposed movably coaxially about the shaft; and
a movable tab mounted to the proximal end of the retractable sheath for moving the retractable sheath relative to the shaft.

In another form of the present invention, there is provided a method for securing a first object to a second object, the method comprising:

providing apparatus comprising:
an anchor, the anchor comprising:
an elongated body having a distal end, a proximal end, and a lumen extending between the distal end and the proximal end, the lumen comprising a distal section and a proximal section, the distal section of the lumen having a wider diameter than the proximal section of the lumen;
a window extending through the side wall of the elongated body and communicating with the lumen, the window being disposed in the vicinity of the intersection between the distal section of the lumen and the proximal section of the lumen and being sized to receive a first object therein;
an elongated element extending through the lumen of the elongated body, the elongated element comprising a proximal end and a distal end; and
a locking element mounted to the distal end of the elongated element and disposed in the distal section of the lumen; and
an inserter, the inserter comprising:
a handle;
a shaft having a distal end and a proximal end, with a lumen extending therebetween, the proximal end of the shaft being mounted to the handle and the distal end of the shaft being configured to releasably engage the elongated body;
a retractable sheath disposed movably coaxially about the shaft; and
a movable tab mounted to the proximal end of the retractable sheath for moving the retractable sheath relative to the shaft;
extending the first object through the window of the elongated body;
using the inserter to position the elongated body in the second object; and
moving the locking element proximally, such that proximal movement of the locking element causes the elongated body to capture the first object to the elongated body, whereby to secure the first object to the second object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (i.e., cam-type FAI);

FIG. 14 is a schematic view showing pincer-type femoroacetabular impingement (i.e., pincer-type FAI);

FIG. 18A is a schematic view showing another suture anchor being used to re-attach the labrum to the acetabulum;

FIGS. 19 and 20 are schematic views showing a novel knotless suture anchor system formed in accordance with the present invention;

FIGS. 21-25 are schematic views showing the knotless suture anchor of the knotless suture anchor system shown in FIGS. 19 and 20, and the distal end of the inserter of the knotless suture anchor system shown in FIGS. 19 and 20;

FIGS. 26 and 27 are schematic views showing the handle of the inserter of the knotless suture anchor system shown in FIGS. 19 and 20;

FIGS. 28A, 29 and 30 show a suture loaded into the knotless suture anchor system shown in FIGS. 19 and 20, wherein FIG. 30 is a cutaway view of FIG. 29;

FIGS. 31-36 are schematic views showing the knotless suture anchor of the knotless suture anchor system shown in FIGS. 19 and 20 securing a suture to bone, wherein FIG. 36 is a cutaway view of FIG. 35;

FIGS. 37-47, 47A and 47B are schematic views showing various constructions for the locking element of the knotless suture anchor system shown in FIGS. 19 and 20;

FIGS. 60-63 are schematic views showing the knotless suture anchor system of FIGS. 48-59 securing a suture to bone (whereby to secure a labrum to bone);

FIGS. 67-69 are schematic views showing another alternative form of knotless suture anchor;

FIGS. 72-74 are schematic views showing another alternative form of knotless suture anchor and the distal end of its associated inserter;

FIGS. 87-90 are schematic views showing another alternative form of knotless suture anchor.

DETAILED DESCRIPTION OF THE PREFERRED EMBODIMENTS

Knotless Suture Anchor System

Figure 1A:
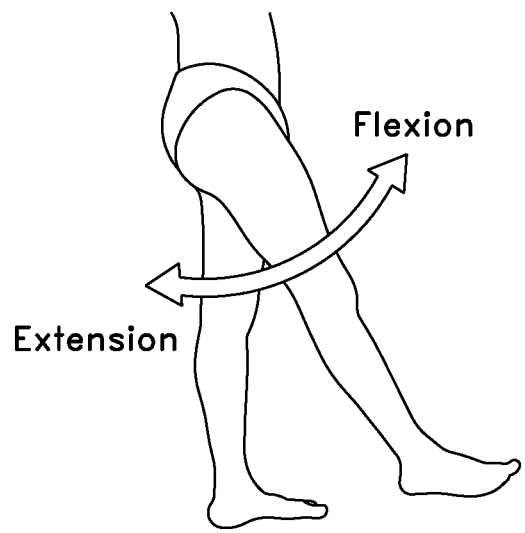
FIGS. 1A-1D are schematic views showing various aspects of hip motion.
Figure 1B:
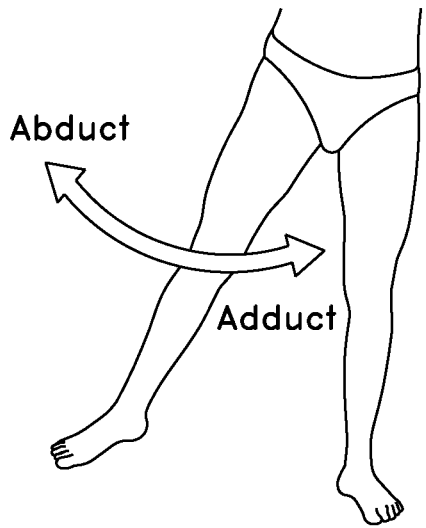
Figure 1C:
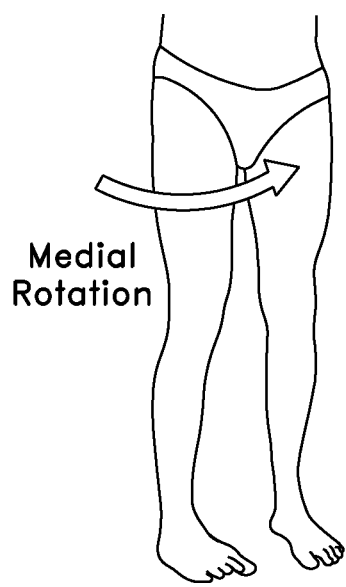
Figure 1D:
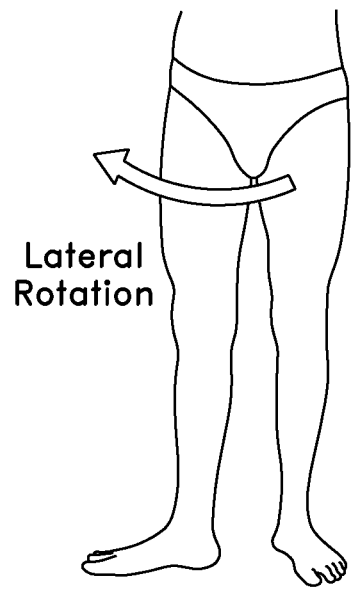
Figure 2:
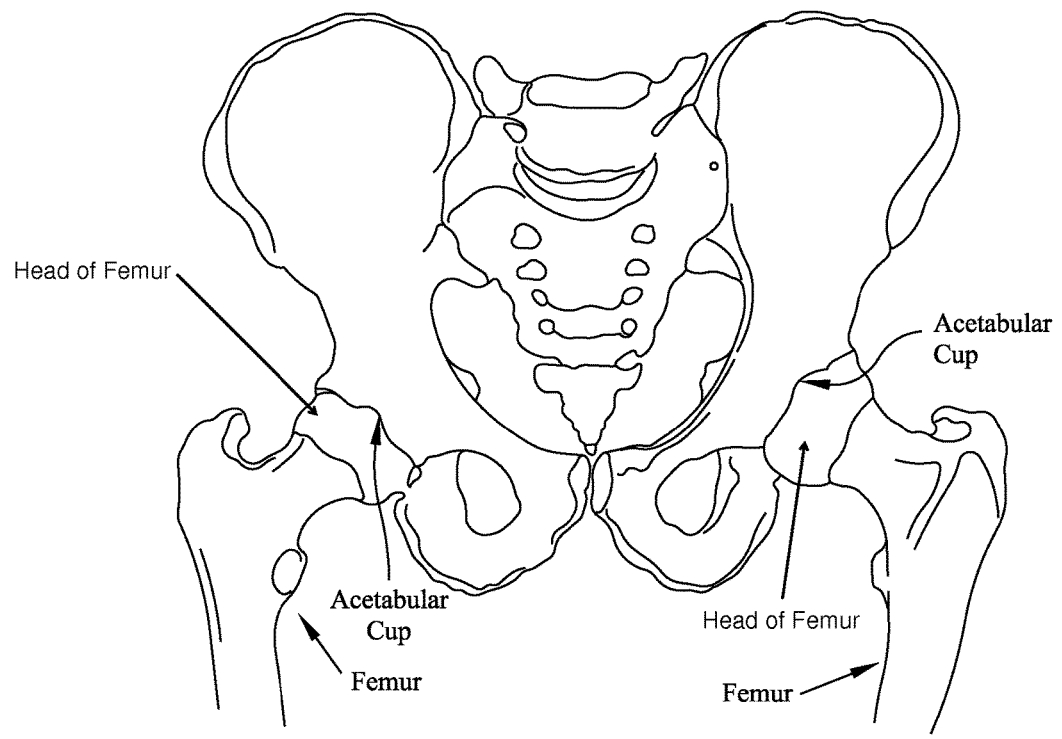
FIG. 2 is a schematic view showing bone structures in the region of the hip joint.
Figure 3:
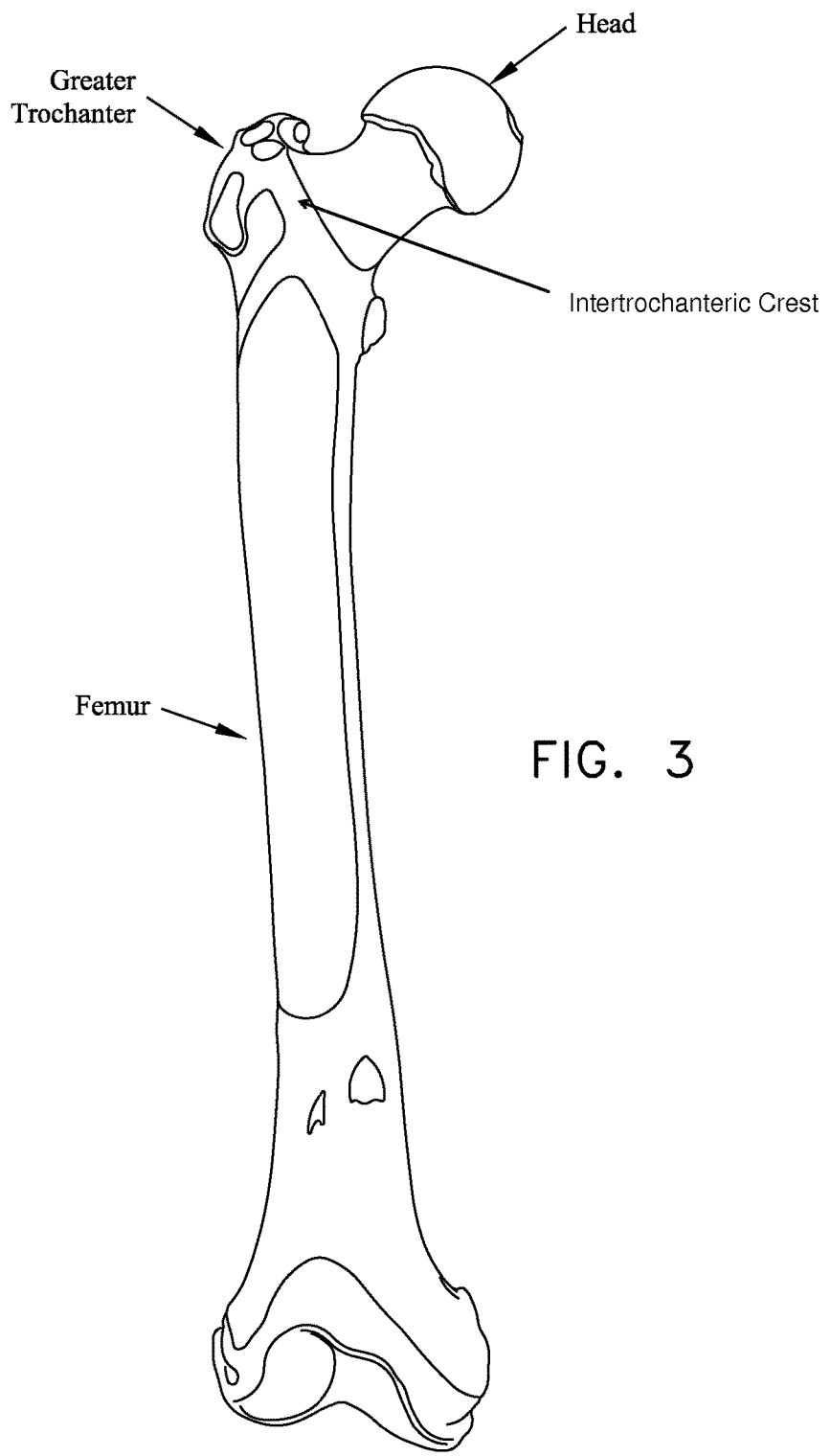
FIG. 3 is a schematic anterior view of the femur.
Figure 4:
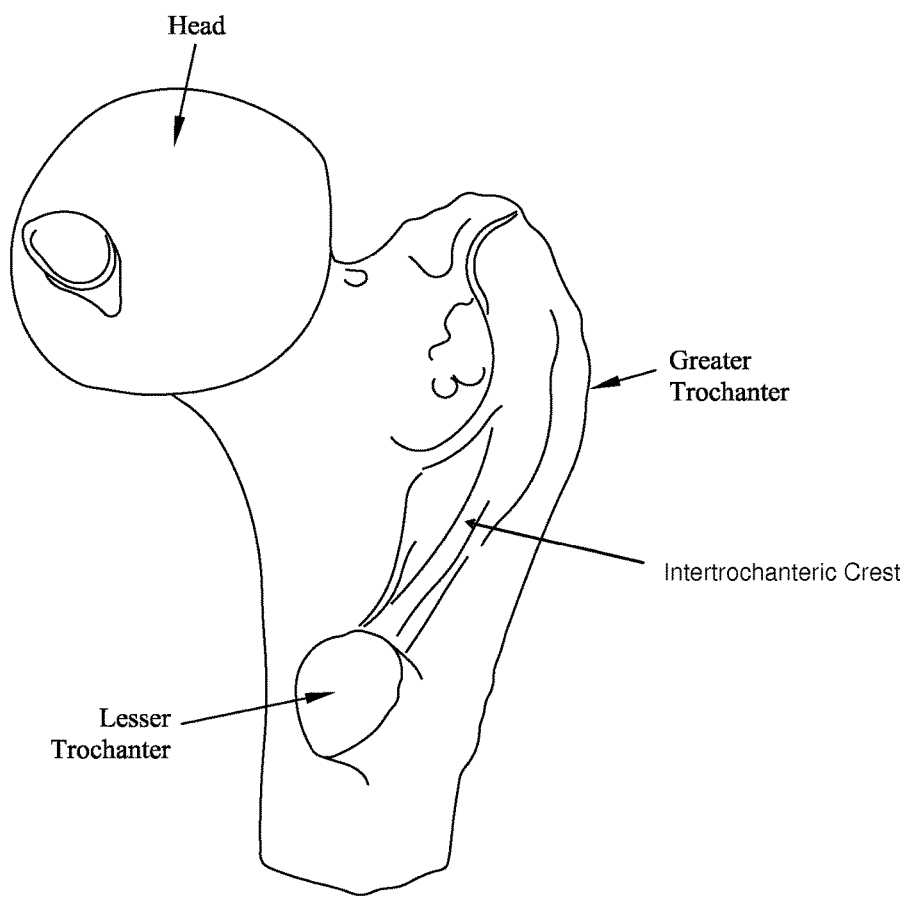
FIG. 4 is a schematic posterior view of the top end of the femur.
Figure 5:
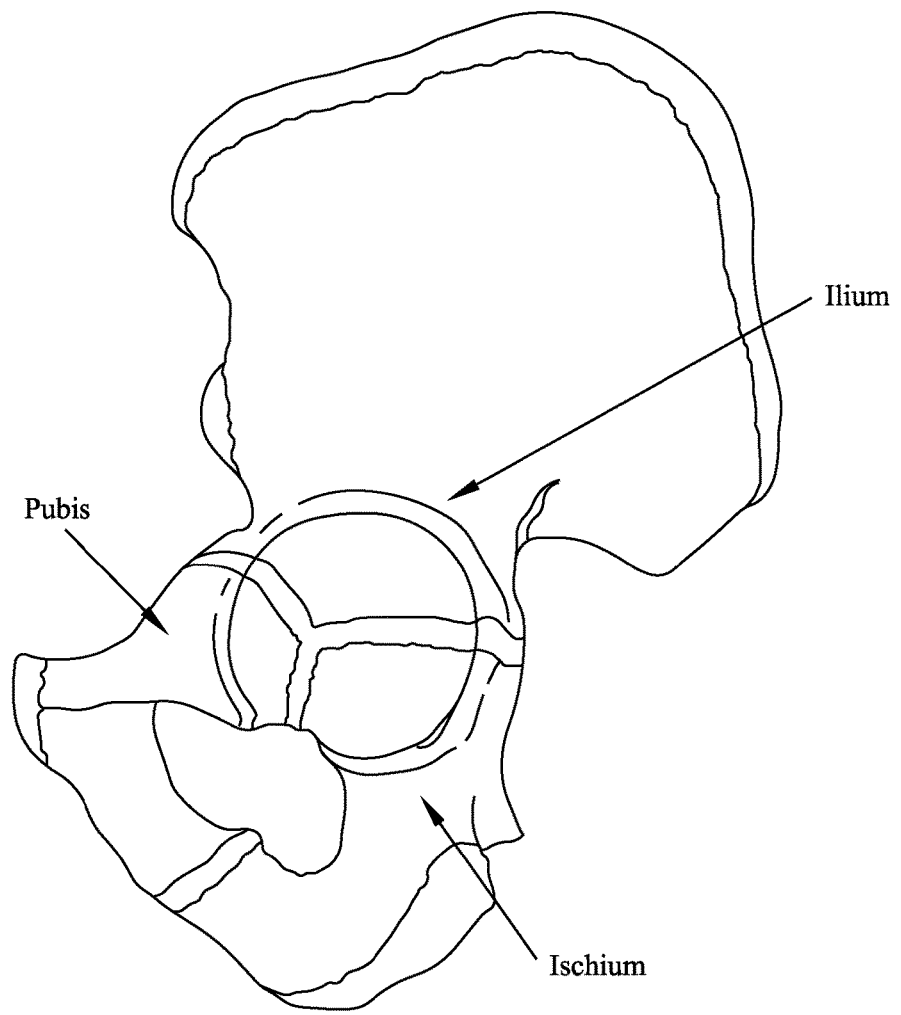
FIG. 5 is a schematic view of the pelvis.
Figure 6:
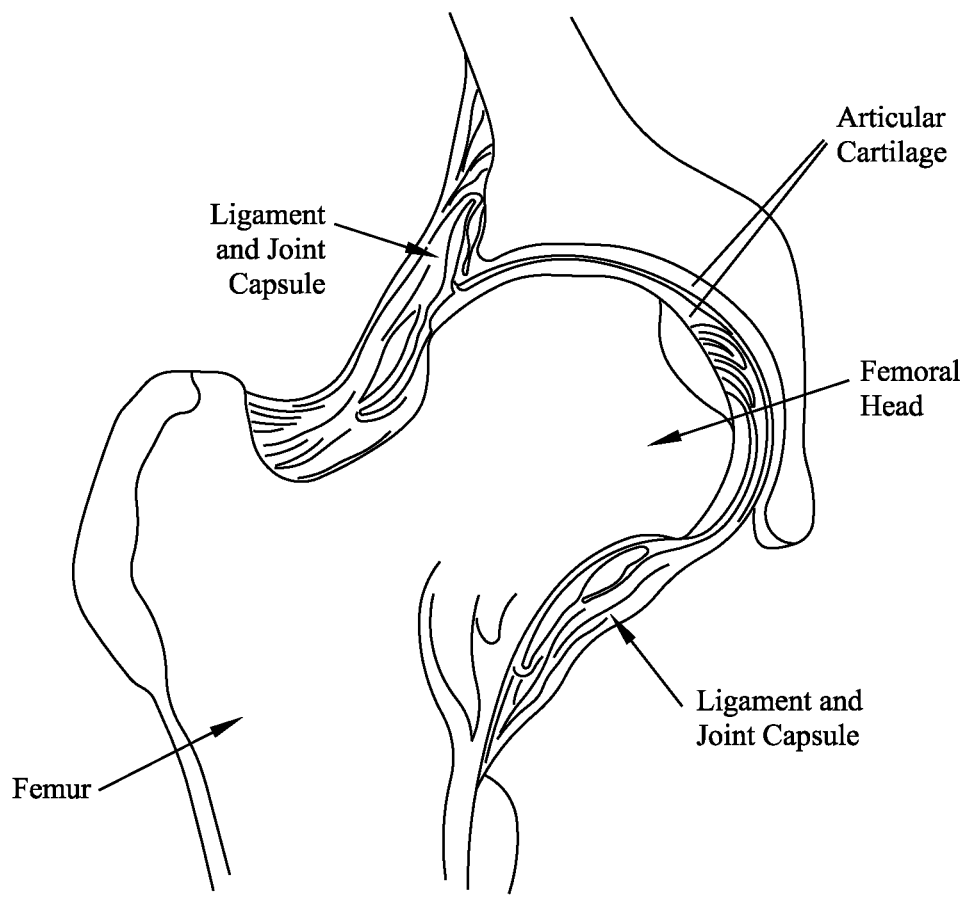
FIGS. 6-12 are schematic views showing bone and soft tissue structures in the region of the hip joint.
Figure 7:
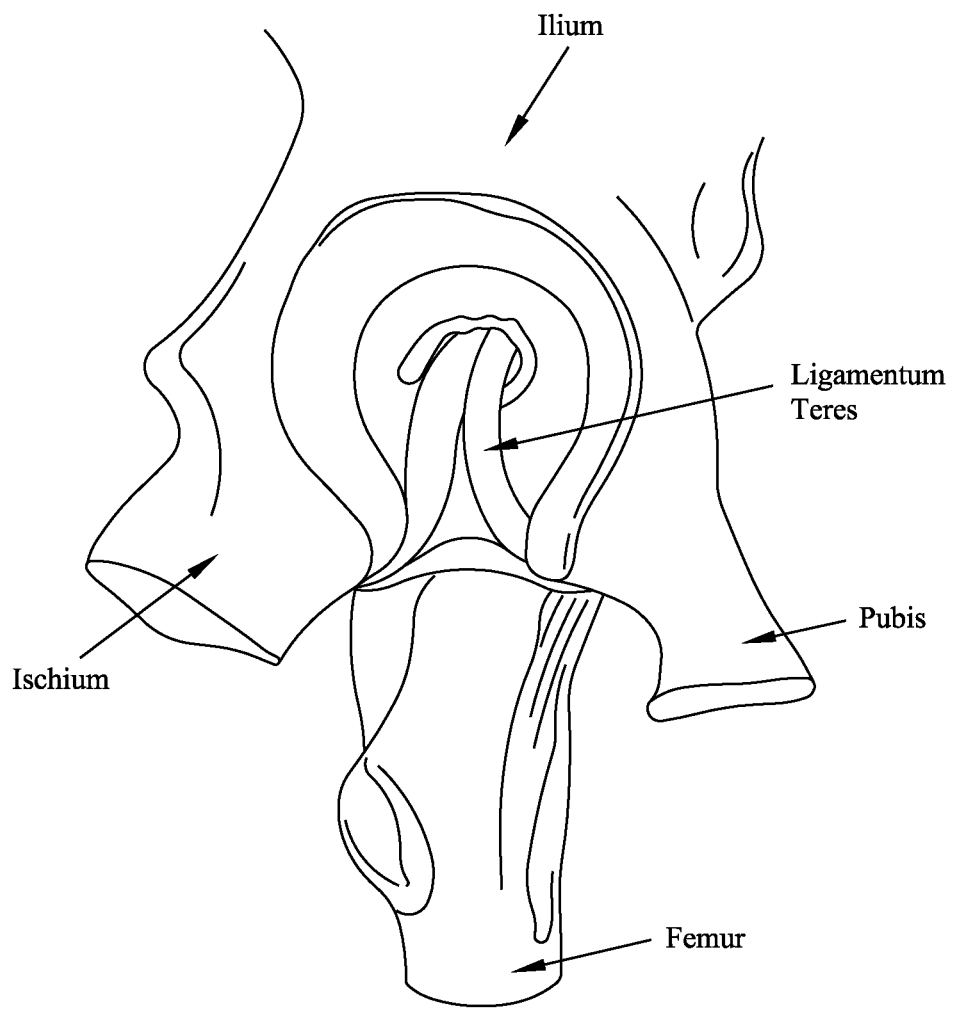
Figure 8:
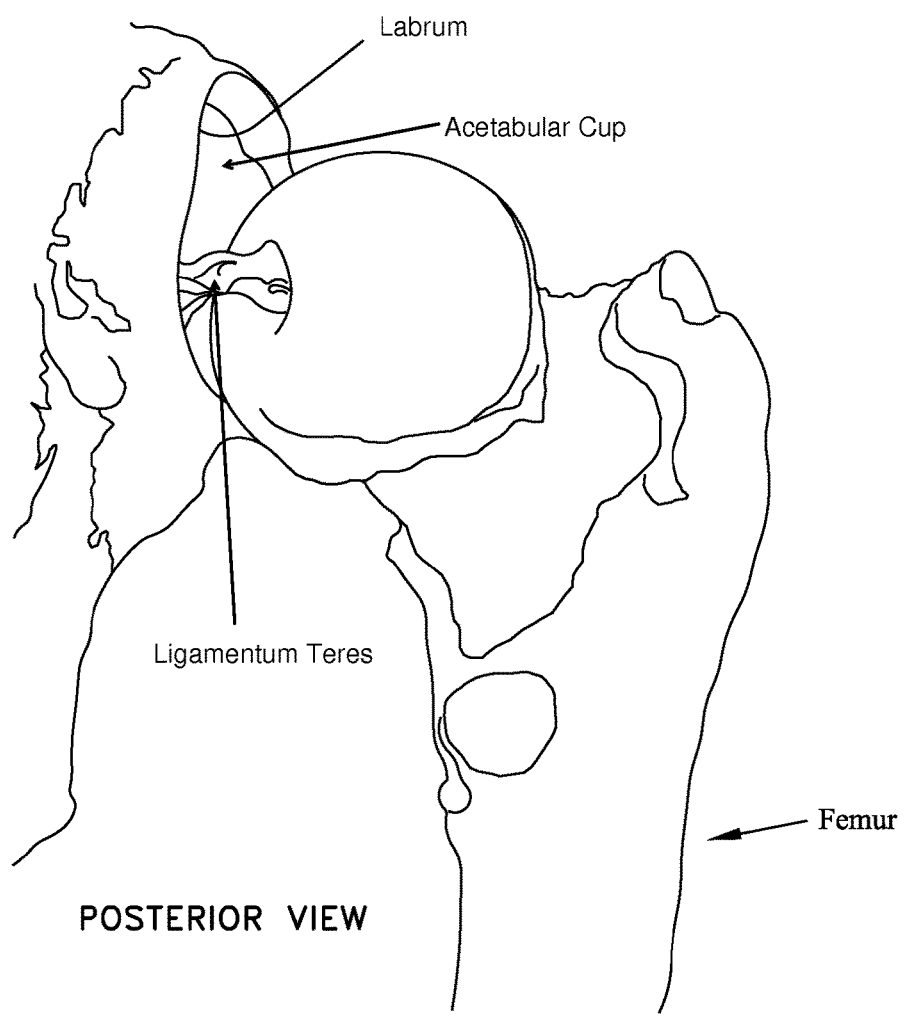
Figure 9:
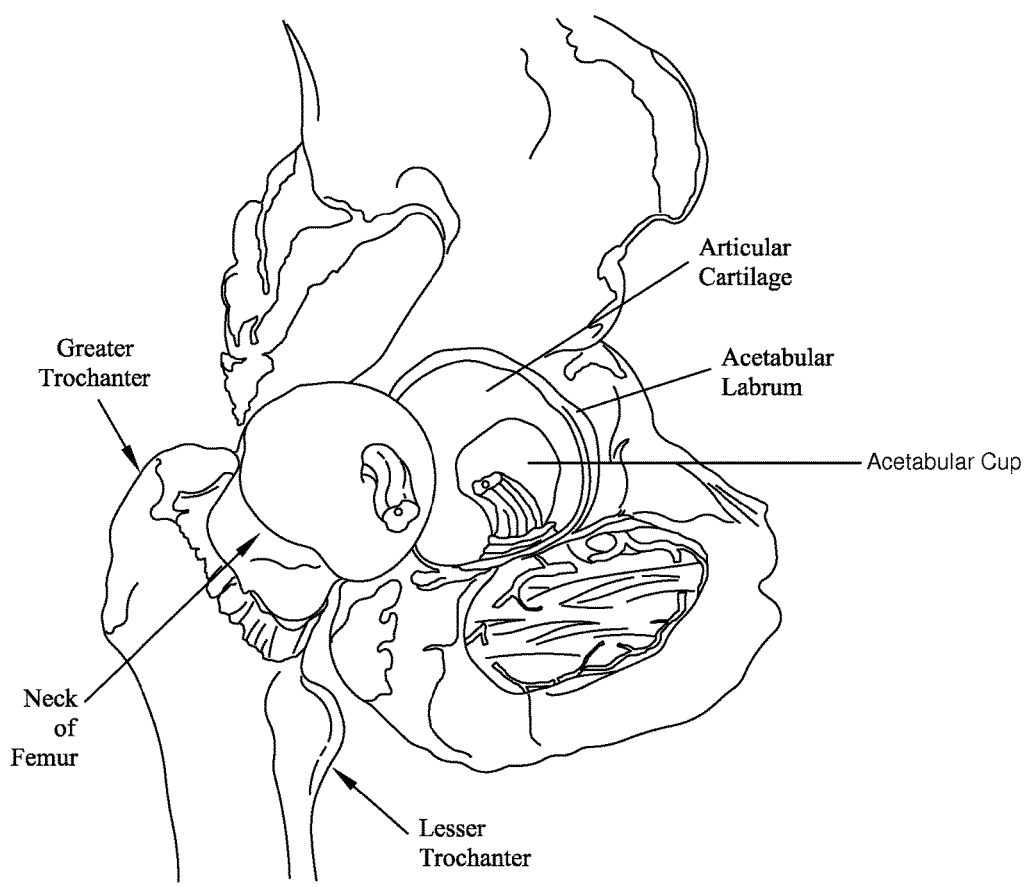
Figure 10:
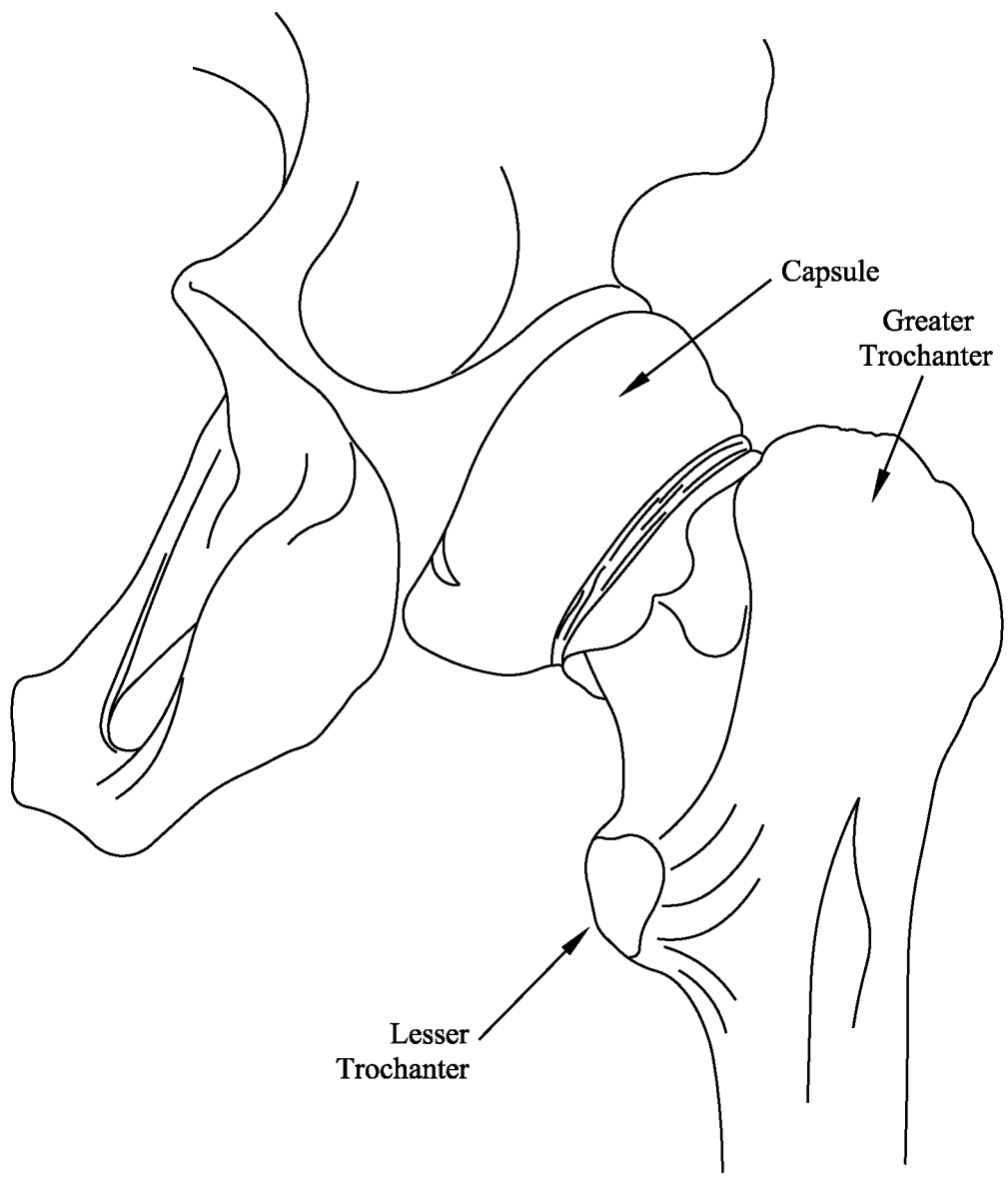
Figure 11:
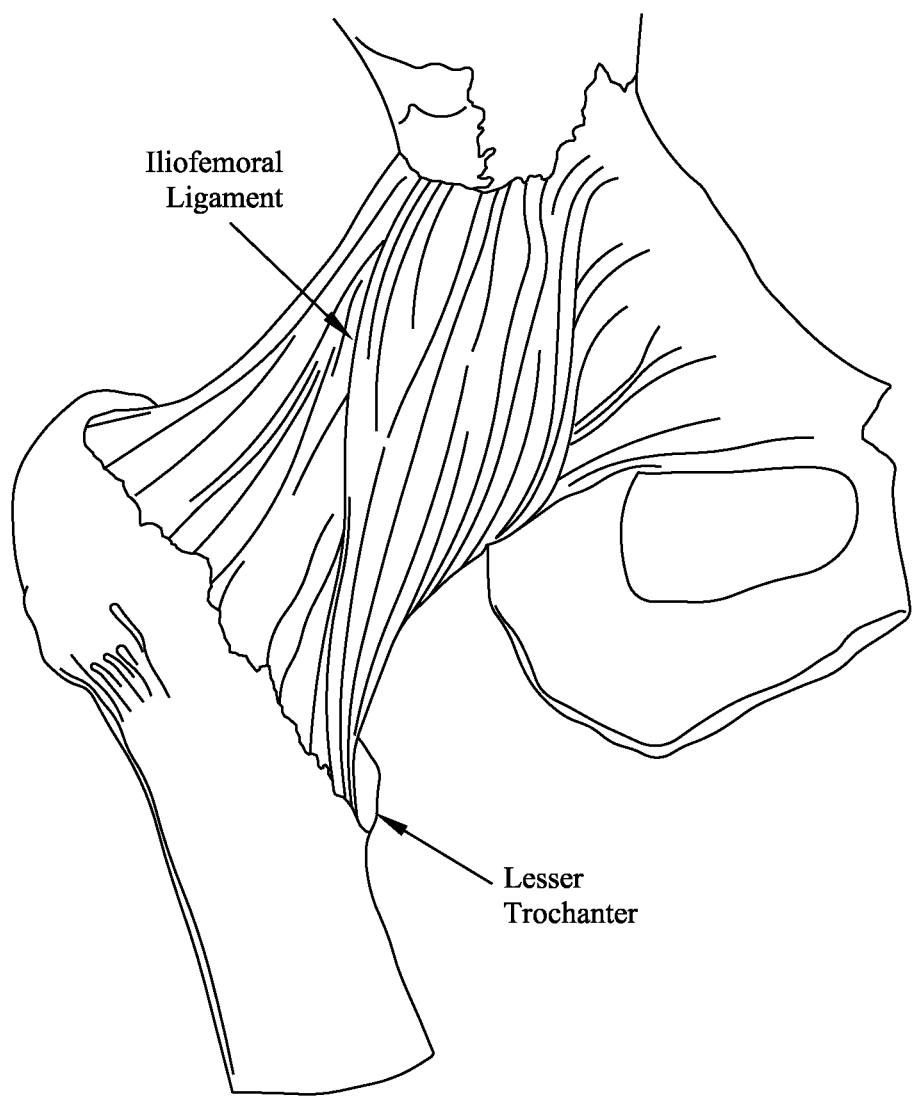
Figure 12:
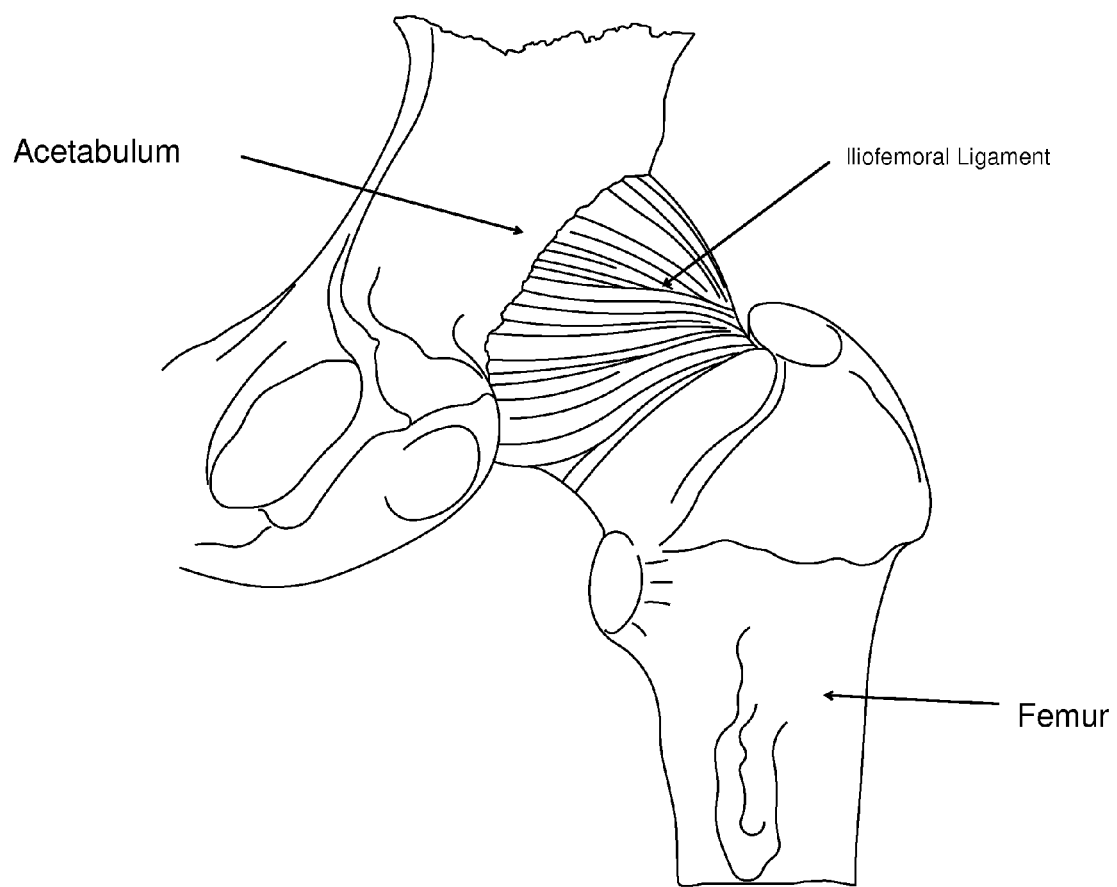
Figure 15:
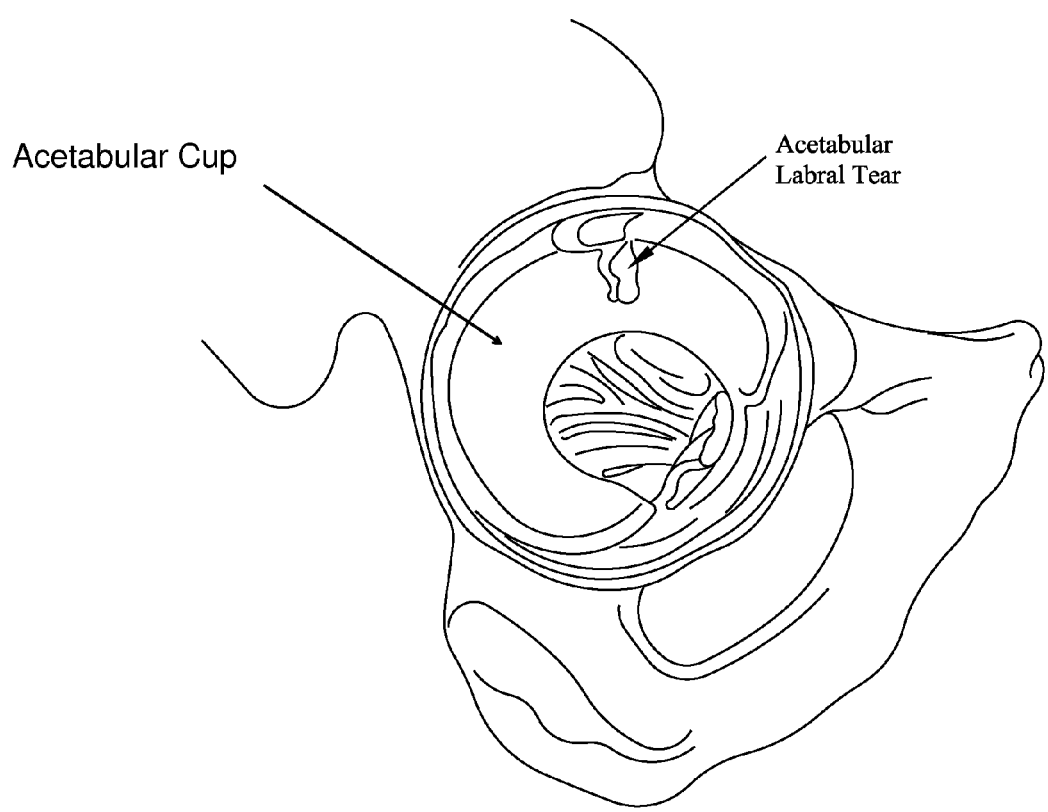
FIG. 15 is a schematic view showing a labral tear.
Figure 16:
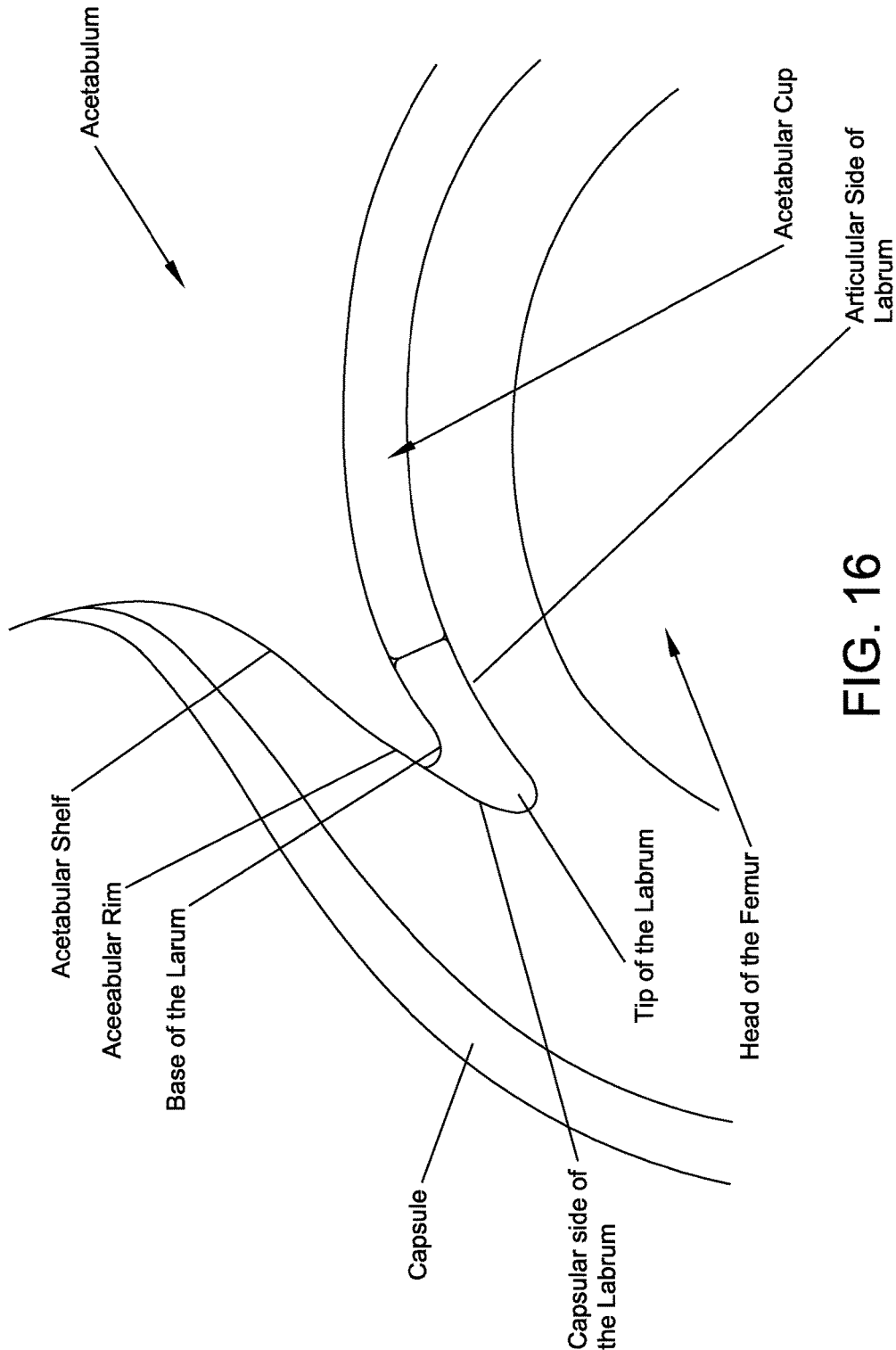
FIG. 16 is a schematic view showing a normal labrum which has its base securely attached to the acetabulum.
Figure 17:
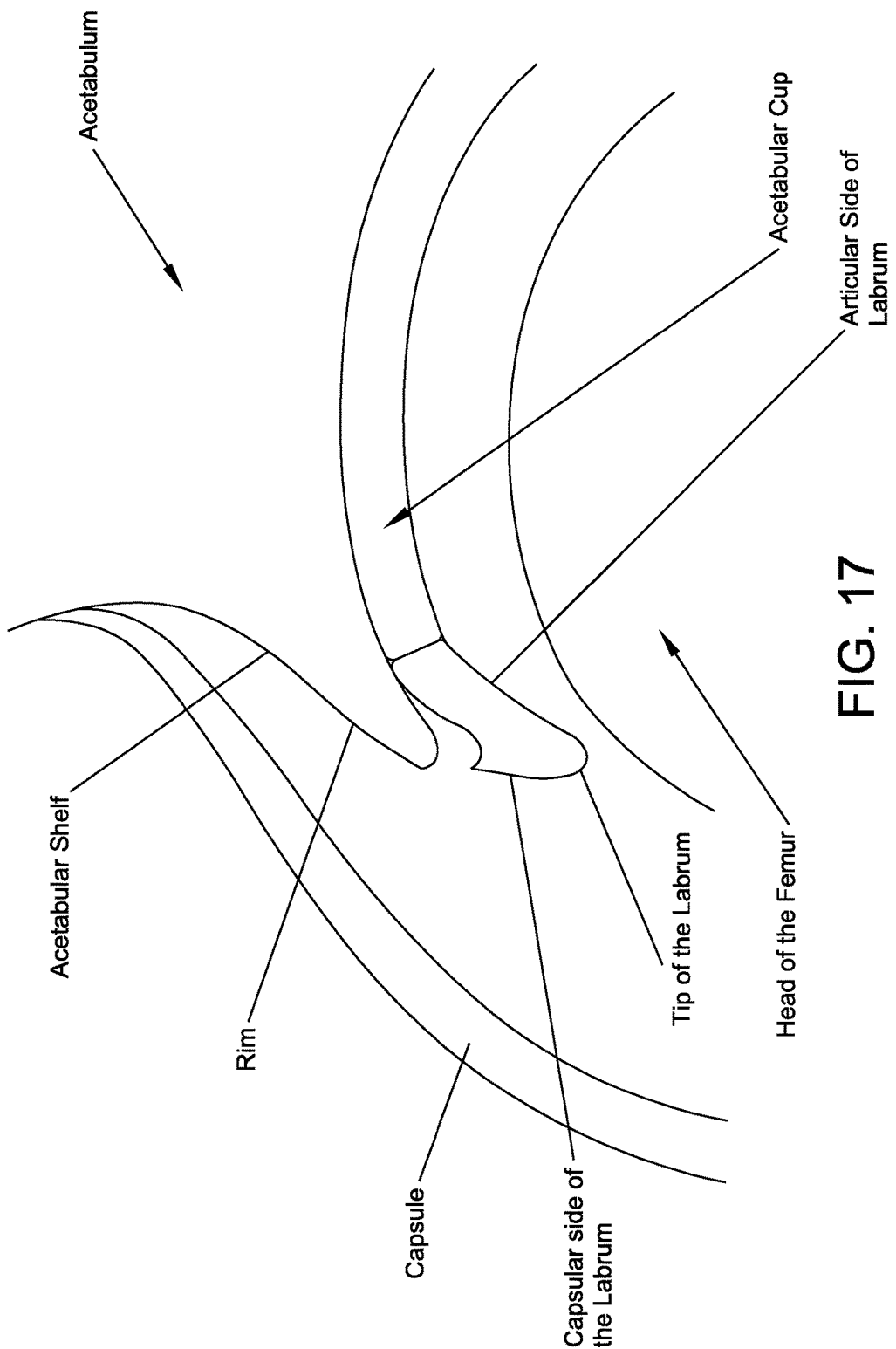
FIG. 17 is a schematic view showing a portion of the labrum detached from the acetabulum.
Figure 18:
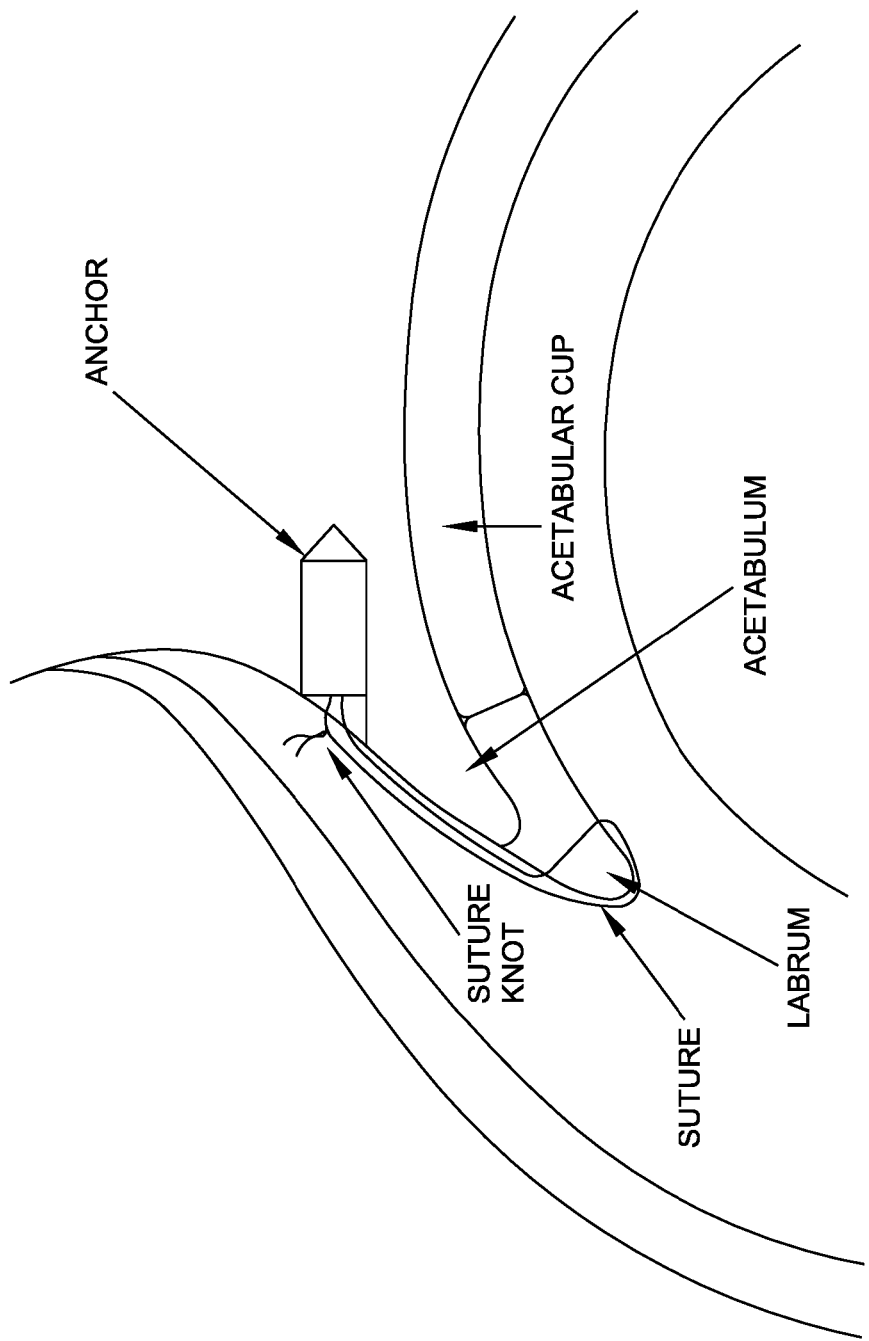
FIG. 18 is a schematic view showing a suture anchor being used to re-attach the labrum to the acetabulum.

Looking first at FIGS. 19 and 20, there is shown a novel knotless suture anchor system 5 formed in accordance with the present invention. Knotless suture anchor system 5 generally comprises a knotless suture anchor 10, an inserter 15 for inserting knotless suture anchor 10 in bone, and a suture threader 20 for threading a suture through knotless suture anchor 10 (and inserter 15) before the knotless suture anchor is deployed in bone.

Looking next at FIGS. 21-25, knotless suture anchor 10 generally comprises a body 25, a locking element 30 for radially expanding the body and securing a suture (not shown in FIGS. 21-25) to the body, and a pull rod 35 for moving locking element 30 proximally relative to body 25, whereby to simultaneously (i) radially expand the body so as to secure knotless suture anchor 10 to bone, and (ii) secure a suture to the body so as to secure that suture to knotless suture anchor 10 (and hence to the bone within which the knotless suture anchor is secured).

More particularly, and still looking now at FIGS. 21-25, body 25 comprises a distal end 40 terminating in a distal end surface 45, a proximal end 50 terminating in a proximal end surface 55, and a stepped bore 60 extending from distal end surface 45 to proximal end surface 55. Stepped bore 60 comprises a distal section 65 having a wider diameter, and a proximal section 70 having a narrower diameter. Distal section 65 preferably has a relatively smooth interior wall, and proximal section 70 preferably has a textured interior wall, e.g., threads 72. A shoulder 75 is formed at the intersection of distal section 65 and proximal section 70.

Body 25 of knotless suture anchor 10 has a generally cylindrical outer surface 80 which may include ribs (or other bone-engaging elements) 85. Ribs (or other bone-engaging elements) 85 may have various configurations, either identical to or varied from one another, and/or may be regularly or irregularly spaced, as will hereinafter be discussed. Body 25 also includes a side opening 90 which extends radially through the side wall of body 25 so as to connect stepped bore 60 with the region outside of the body 25 of knotless suture anchor 10. Side opening 90 is preferably located in the vicinity of shoulder 75. In one preferred form of the invention, side opening 90 extends from a region distal to shoulder 75 to a region approximately even with, or proximal to, shoulder 75. A portion of generally cylindrical outer surface 80 is recessed as shown at 95 (i.e., to accommodate a suture extending alongside the outer surface of the body), and the proximal end 50 of body 25 is reduced in diameter as shown at 100 so as to form an annular shoulder 105. Note that the axis of stepped bore 60 is off-center from the axis of outer surface 80 (FIG. 25) so as to strengthen the side wall of body 25 at 95 while still minimizing anchor diameter.

Still looking now at FIGS. 21-25, locking element 30 comprises an elongated body 110 having an enlarged distal end 115 which includes a thin flange 120 and terminates in a distal end surface 125, a proximal end 130 which terminates in a proximal end surface 135, and a stepped bore 140 which extends from distal end surface 125 to proximal end surface 135. Note that thing flange 120 has a larger diameter than enlarged distal end 115, and enlarged distal end 115 has a larger diameter than the portion of locking element 30 which is proximal to enlarged distal end 115. Proximal end 130 of locking element 30 is preferably tapered, e.g., in the manner shown in FIGS. 22 and 24, whereby to facilitate advancement of locking element 30 into proximal section 70 of stepped bore 60 of body 25, as will hereinafter be discussed. In one form of the present invention, proximal end 130 of locking element 30 includes a weakened section 132, preferably formed by a circumferential groove 133, whereby to allow the proximalmost portion of locking element 30 to separate from the remainder of locking element 30, as will hereinafter be discussed. Stepped bore 140 comprises a distal section 145 and a proximal section 150, with distal section 145 having a larger diameter than the diameter of proximal section 150, and with proximal section 150 having a smaller diameter than the diameter of distal section 145. A shoulder 155 is formed at the intersection of distal section 145 and proximal section 150. Locking element 30 has a generally cylindrical outer surface 160 which may include ribs (or other surface profile elements) 165. Ribs (or other surface profile elements) 165 may have various configurations, either identical to or varied from one another, and/or may be regularly or irregularly spaced, as will hereinafter be discussed.

Locking element 30 is sized so that (i) the diameter of its generally cylindrical outer surface 160 is less than the diameter of distal section 65 of stepped bore 60 of body 25, and (ii) the diameter of its flange 120 at the distal end of the locking element is larger than the diameter of distal section 65 of stepped bore 60 of body 25, such that cylindrical outer surface 160 of locking element 30 can be received in distal section 65 of stepped bore 60 of body 25, but flange 120 at the distal end of locking element 30 cannot normally be received in distal section 65 of stepped bore 60 of body 25. Furthermore, locking element 30 is sized so that when its flange 120 is seated against end surface 45 of body 25, proximal end surface 135 of locking element 30 is disposed distal to at least the proximalmost portion of side opening 90 in body 25 and, preferably, distal to the entire side opening 90 in body 25. In one preferred form of the invention, the diameter of generally cylindrical outer surface 160 of locking element 30 is approximately equal to, or somewhat larger than, the diameter of proximal section 70 of stepped bore 60 of body 25. As a result, when one or more sutures are disposed within distal section 65 of stepped bore 60 (i.e., when one or more sutures extend through proximal section 70 of stepped bore 60, through distal section 65 of stepped bore 60 and out of side opening 90, as will hereinafter be discussed), proximal movement of locking element 30 into proximal section 70 of stepped bore 60 of body 25 simultaneously causes (i) the creation of an interference fit between the generally cylindrical outer surface 160 of locking element 30, the one or more sutures extending through proximal section 70 of stepped bore 60 and the inner wall of proximal section 70 of stepped bore 60, and (ii) radial expansion of body 25. Thus it will be seen that proximal movement of locking element 30 into proximal section 70 of stepped bore 60 of body 25 causes radial expansion of the body so as to secure knotless suture anchor 10 to a surrounding bone, and captures the suture within the proximal section 70 of stepped bore 60, whereby to secure the suture to the knotless suture anchor 10 (and hence to the bone within which the knotless suture anchor 10 is secured). Furthermore, distal end 115 of locking element 30 has a diameter which is smaller than distal section 65 of stepped bore 60, but distal end 115 of locking element 30 has a diameter which is larger than proximal section 70 of stepped bore 60. As a result, distal end 115 of locking element 30 will stop proximal movement of locking element 30 when distal end 115 abuts shoulder 75 of body 25.

It will be appreciated that, when locking element 30 is moved proximally into proximal section 70 of stepped bore 60 of body 25, thin flange 120 (located at the distal end of locking element 30) will engage distal end surface 45 of body 25 and thereafter collapse (or bend) so that thin flange 120 is able to enter distal section 65 of stepped bore 60. By remaining engaged against distal end surface 45 of body 25 until a sufficient proximal force is applied to pull rod 35, thin flange 120 helps to prevent the unintentional actuation of knotless suture anchor 10 by requiring the application of a force to pull rod 35 above a pre-determined threshold force (i.e., the pre-determined force at which thin flange 120 collapses, or bends) in order to permit movement of locking element 30 proximally (whereby to actuate knotless suture anchor 10). Note that thin flange 120 also helps secure knotless suture anchor 10 on inserter 15 during delivery of the knotless suture anchor to the surgical site. This is of significance since, unlike knotted suture anchors which are typically delivered through a guide which provides mechanical support to the knotted suture anchor during delivery, knotless suture anchors are typically delivered without the benefit of such mechanical support and hence are subjected to more forces which can dislodge the knotless suture anchor from the inserter during delivery to the bone site and into the bone hole.

Looking now at FIGS. 21-27, pull rod 35 comprises an elongated body 170 having a distal end 175 terminating in an enlarged head 180, and a proximal end 185 terminating within the handle 190 of inserter 15, as will hereinafter be discussed in further detail. Elongated body 170 of pull rod 35 is sized to pass through proximal section 150 of bore 140 of locking element 30, and enlarged head 180 of pull rod 35 is sized to seat in distal portion 145 of bore 140 of locking element 30, such that pulling proximally on elongated body 170 of pull rod 35 will cause locking element 30 to move proximally.

It should also be appreciated that enlarged head 180 of pull rod 35 comprises a proximal surface 191 which extends circumferentially around the distal end of pull rod 35 at the junction of (or transition between) elongated body 170 and enlarged head 180. Proximal surface 191 of enlarged head 180 may comprise a fillet or chamfer, such that when a sufficient proximal force (i.e., a proximal force above a set threshold force) is applied to pull rod 35, enlarged head 180 can move proximally into bore 140 of locking element 30, as will hereinafter be discussed.

Looking now at FIGS. 19-27, inserter 15 generally comprises a shaft 195 having a distal end 200 terminating in distal end surface 205, a proximal end 210 terminating in a proximal end surface 215, and a bore 220 extending therebetween. Distal end 200 of shaft 195 comprises a counterbore 225 which is sized so as to receive the proximal end 50 of body 25 of knotless suture anchor 10, in a male/female connection, with distal end surface 205 of shaft 195 being seated against annular shoulder 105 of body 25. Note that the proximal end 50 of body 25 of knotless suture anchor 10 is not round (FIG. 25), and the cross-section of counterbore 225 is also not round, so as to resist twisting motions of suture anchor 10 vis-à-vis inserter 15. A side opening 227 extends radially through the side wall of shaft 195 so as to connect bore 220 with the region outside the shaft. Preferably side opening 227 in shaft 195 is aligned with side opening 90 in knotless suture anchor 10.

The proximal end 210 of shaft 195 is secured to handle 190. Handle 190 comprises a lever 230 which is rotatably mounted to handle 190 via a pivot pin 235. The proximal end 185 of pull rod 35 is secured to lever 230 such that when lever 230 is activated (i.e. squeezed towards handle 190), pull rod 35 is moved proximally, whereby to move locking element 30 proximally, as will hereinafter be discussed. A finger-to-finger engagement is provided at 232, 233 so as to prevent accidental activation of lever 230. Preferably pull rod 35 is set with a small amount of tension (that is below the threshold force that is required to retract locking element 30) so as to help hold suture anchor 10 on the distal end of inserter 15.

Figure 28:
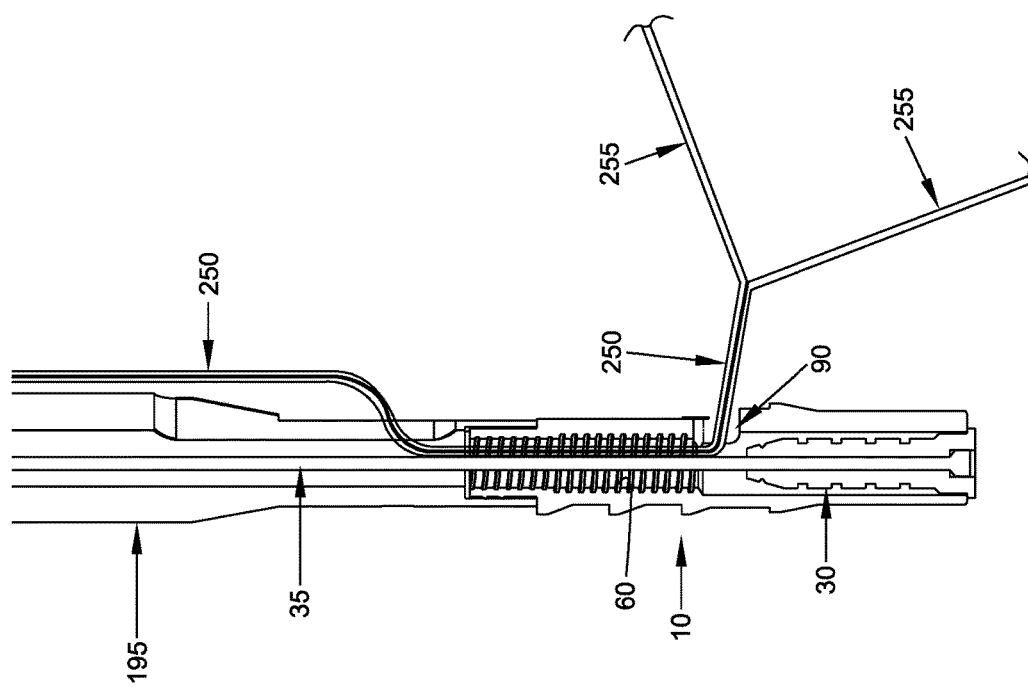
FIG. 28 shows portions of the knotless suture anchor system (i.e., the suture anchor, inserter and suture threader) shown in FIGS. 19 and 20.
Figure 28A:
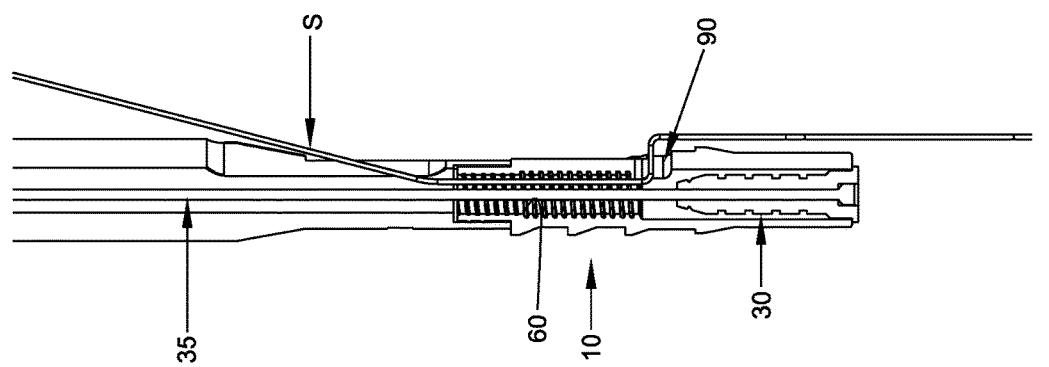

Looking next at FIGS. 19, 20 and 28, suture threader 20 is provided for threading a suture through knotless suture anchor 10 (and inserter 15) before the knotless suture anchor is deployed in bone. In one preferred form of the invention, suture threader 20 is pre-mounted to shaft 195 of inserter 15, with the suture threader having a portion threaded through inserter 15 and knotless suture anchor 10 so as to facilitate threading a suture (or multiple sutures) through the knotless suture anchor 10 and through inserter 15; see FIGS. 19 and 28. More particularly, suture threader 20 preferably comprises a body 240 having clamping arms 245 extending therefrom. Clamping arms 245 are configured to releasably secure body 240 of suture threader 20 to shaft 195 of inserter 15. A wire shaft 250 extends distally from body 240, and a collapsible, diamond-shaped capture element 255 is secured to the distal end of wire shaft 250. In a preferred embodiment, the wire shaft 250 and diamond-shaped capture element 255 are formed out of a single, thin Nitinol wire having its two terminal ends secured to body 240. Prior to use, suture threader 20 has its diamond-shaped capture element 255 collapsed radially inwardly, and it is passed through side opening 227 of shaft 195, along bore 220 of shaft 195 of inserter 15, along proximal portion 70 of stepped bore 60 of body 25 of knotless suture anchor 10, and out side opening 90 of body 25 of knotless suture anchor 10, whereupon diamond-shaped capture element 255 re-expands to its erected shape, e.g., in the manner shown in FIGS. 19 and 28.

Using the Knotless Suture Anchor System to Secure Suture to Bone

Figure 30:
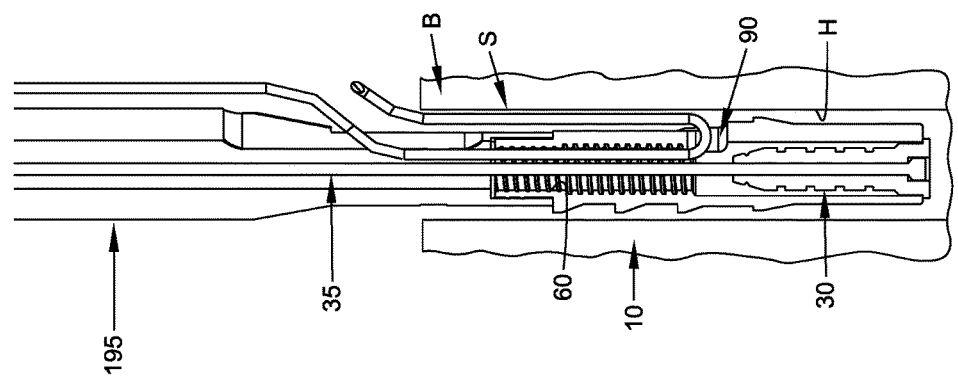
Figure 29:
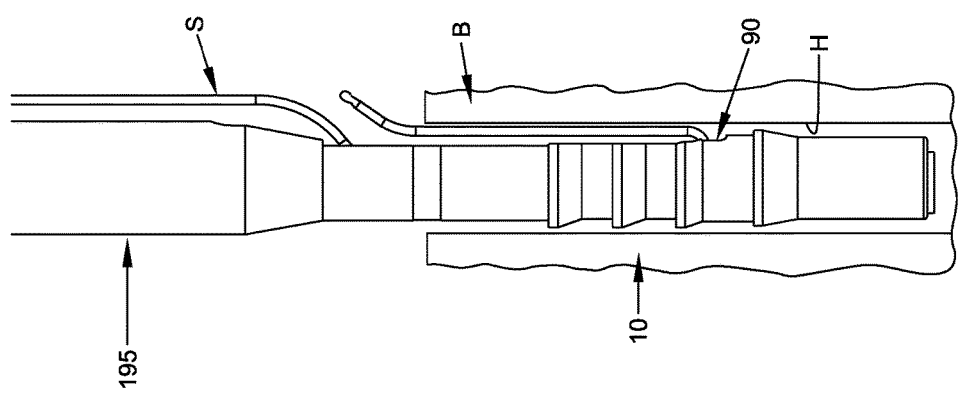
Figure 36:
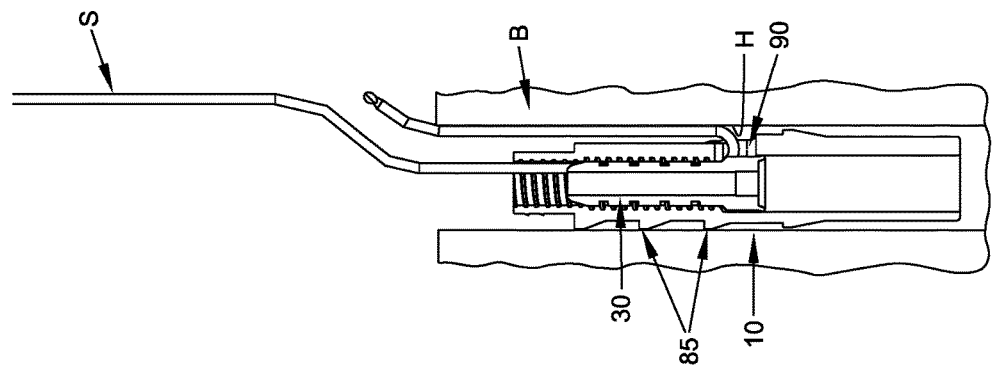
Figure 35:
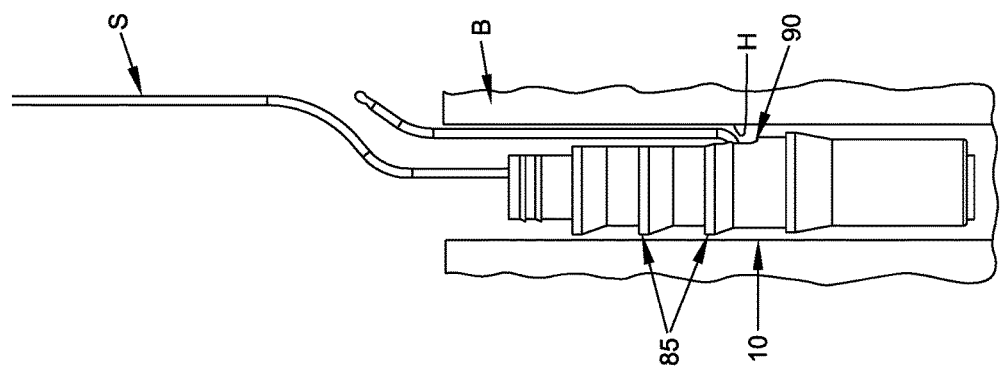

In use, the suture which is to be secured to a bone by means of knotless suture anchor 10 is first passed through the tissue which is to be secured to the bone, next the suture is passed through diamond-shaped capture element 255 of suture threader 20, and then suture threader 20 is pulled rearwardly on shaft 195 of inserter 15, towing the suture with it, until the suture has been pulled through side opening 90 of knotless suture anchor 10, along proximal portion 70 of stepped bore 60 of body 25 of knotless suture anchor 10, along bore 220 of shaft 195 of inserter 15, and out side opening 227 in shaft 195 of inserter 15. See FIGS. 29 and 30, which show an exemplary suture S threaded through body 25 of knotless suture anchor 10 and shaft 195 of inserter 15. It should be appreciated that, although a single suture strand is depicted in the figures, in a preferred embodiment, two strands of suture are threaded through body 25 of knotless suture anchor 5 and shaft 195 of inserter 15.

Thereafter, and looking now at FIGS. 29-36, in order to secure the suture S to a bone, inserter 15 is used to advance knotless suture anchor 10 and suture S into a hole H (FIGS. 29 and 30) formed in a bone B. Suture S may then be tensioned so as to adjust the position of the tissue relative to the bone. This can be accomplished by pulling on the free ends of the suture S, either independently or together. Sufficient tension will overcome any friction in the suture path and reduce the distance from the tissue to the knotless suture anchor 10 (and hence to the bone). Then the lever 230 is moved toward handle 190, whereby to force pull rod 35 proximally. This action causes locking element 30 to move proximally (FIGS. 31 and 32) so as to simultaneously (i) expand body 25 of knotless suture anchor 10 within the hole formed in the bone, whereby to secure knotless suture anchor 10 to the bone, and (ii) capture suture S between locking element 30 and the side wall of proximal portion 70 of stepped bore 60 of body 25 of knotless suture anchor 10, whereby to secure suture S to body 25 of knotless suture anchor 10. Further proximal movement of pull rod 35 (by way of moving lever 230 further towards handle 190) causes the enlarged head 180 of pull rod 35 to force its way through proximal portion 150 of stepped bore 140 of locking element 30 (FIG. 33). It should be appreciated that, in order to impart a sufficient proximal force to locking element 30 so as to move locking element 30 proximally, while still permitting enlarged head 180 to force its way through bore 140 of locking element 30 when a sufficient proximal force is applied to pull rod 35, enlarged head 180 needs to be larger in diameter than the diameter of proximal section 150 of bore 140 but not so large that it cannot be pulled through the bore 140 when sufficient proximal force is applied. It has been found that, with a bore 140 having a diameter of approximately 0.0135 inches, an enlarged head 180 having a diameter of approximately 0.0250 inches will provide adequate "interference" between enlarged head 180 and shoulder 155 so as to provide sufficient resistance to entering bore 140 when a proximal force less than the maximum proximal force (i.e., partial activation force) is applied (FIG. 32). At the same time, such a configuration permits the enlarged head 180 to enter bore 140 (FIG. 33) when a sufficient proximal force (i.e., full activation force) is applied to pull rod 35 (and hence to enlarged head 180).

In other words, with the present invention, the force required to pull locking element 30 proximally so as to lock suture S to the suture anchor, and so as to expand the body of the suture anchor, is less than the force required to draw pull rod 35 through locking element 30 so as to disengage pull rod 35 from locking element 30—this ensures that pull rod 35 is not disengaged from locking element 30 until locking element 30 has locked suture S to the suture anchor and expanded the body of the suture anchor. Furthermore, the force required to draw pull rod 35 through locking element so as to disengage pull rod 35 from locking element 30 is less than the force required to pull locking element 30 through the proximal end of body 25 of the knotless suture anchor 10 (due to the fact that distal end 115 of locking element 30 is sufficiently larger than proximal section 150 of bore 140)—this ensures that pull rod 35 disengages from locking element 30 and locking element 30 is never pulled through the proximal end of body 25 of the knotless suture anchor 10. In other words, the force required to pull locking element 30 through proximal end of body 25 is greater than the force required to draw pull rod 35 through locking element so as to disengage pull rod 35 from locking element 30 (i.e., the full activation force).

In addition, the shape of proximal surface 191 of enlarged head 180 of pull rod 35 also influences the proximal force at which enlarged head 180 will enter into, and begin moving through, bore 140 in locking element 30. In a preferred form of the invention, proximal surface 146 of enlarged head 180 comprises a fillet of approximately 0.005 inches (or a chamfer of approximately 45 degrees).

Further proximal movement of pull rod 35 (i.e., by way of moving lever 230 even further towards handle 190) causes pull rod 35 to completely pull enlarged head 180 through bore 140 and out of the proximal end of locking element 30 (FIG. 34).

As noted above, locking element 30 comprises a weakened section 132 located at the proximal end of locking element 30. As enlarged head 180 encounters weakened section 132, the weakened section will separate from locking element 30, allowing a proximal portion of locking element 30 to detach from the locking element and be removed from the anchor by pull rod 35 (FIG. 34). At this point, inserter 15 can be removed from the hole H in bone B (see FIGS. 35 and 36), leaving the knotless suture anchor 10 secured in the hole H in the bone B, and with the suture S secured to the knotless suture anchor and emanating from the bone hole H, whereby to secure the suture (and hence the tissue which the suture S has been passed through) to the bone B.

Additional Constructions

It should be appreciated that ribs 165 of locking element 30, and the internal threads 72 disposed on the interior wall of the proximal section 70 of stepped bore 60, provide greater securement to one another, and to suture S, than that which would be provided by smooth surfaces. Capturing suture S between the ribs 165 of locking element 30 (which engage suture S after locking element 30 is moved proximally into stepped bore 60 of body 25) and the internal threads 72 disposed on the interior wall of the proximal section 70 of stepped bore 60 of knotless suture anchor 10 creates a secure fit of locking element 30 and suture S within body 25, such that tissue can be sufficiently secured to the knotless suture anchor 10 (and hence to bone) without the risk of locking element 30 or suture S moving within the body 25 of knotless suture anchor 10.

As noted above, ribs 165 may have various configurations, either identical to or varied from one another, and/or may be regularly or irregularly spaced.

Figure 37:
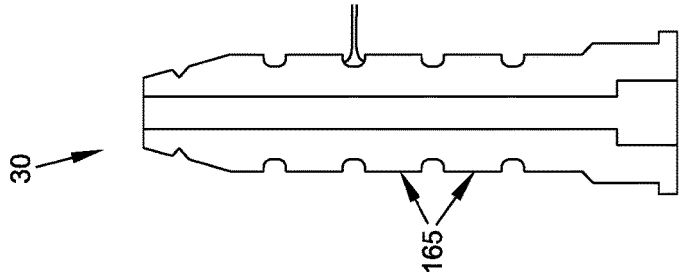

Thus, while "square-profile" ribs 165 are depicted in FIGS. 22, 24, 28, 30-34 and 36, ribs of other profiles and/or geometries (e.g., "triangle-profile", helical, threaded, knurling, etc.) also fall within the scope of the present invention. See, for example, FIG. 37, which shows ribs 165 formed with fillets 300.

Figure 41:
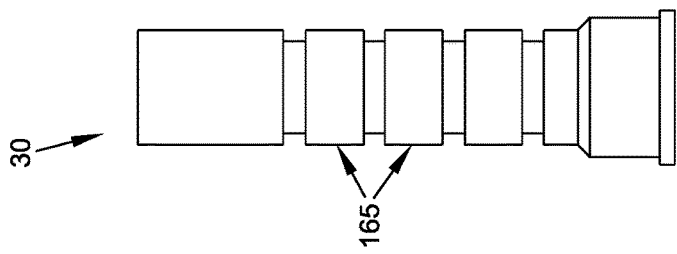
Figure 40:
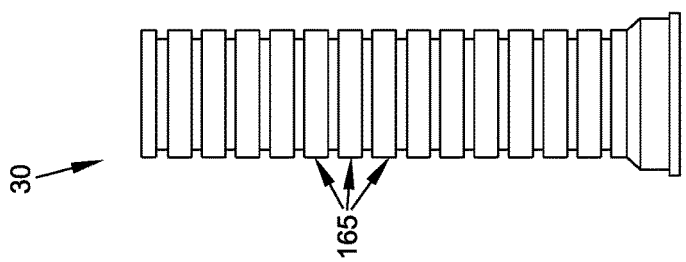
Figure 39:
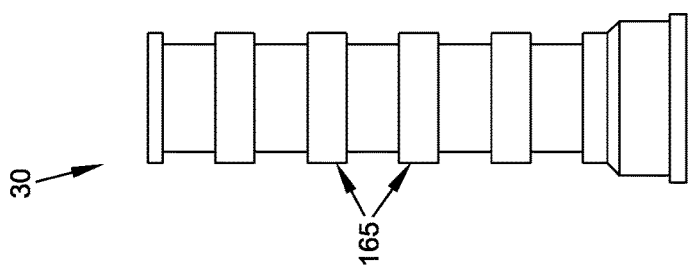
Figure 38:
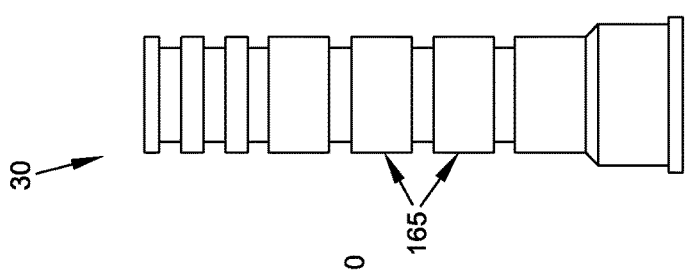

Furthermore, while ribs 165 are depicted in FIGS. 22, 24, 28, 30-34, 36 and 37 as being evenly spaced from one another, it may be desirable to vary the spacing between the ribs, and/or to vary the dimensions of the ribs themselves, so as to provide desired characteristics to locking element 30 and hence to knotless suture anchor 10. By way of example but not limitation, the ribs 165 of locking element 30 can have a variable profile along the length of locking element 30, whereby to provide the knotless suture anchor 10 with variable characteristics along its length. More particularly, locking element 30 may be formed so that the proximal end of the locking element has fewer ribs 165 than the distal end of the locking element, and/or the ribs 165 at the proximal end of the locking element may be spaced farther apart than the ribs 165 at the distal end of the locking element, and/or the ribs 165 at the proximal end of the locking element may be thinner (in a longitudinal sense) than the ribs 165 at the distal end of the locking element (see FIG. 38) such that the proximal section of locking element 30 will be "weaker" than the distal section of locking element 30. In other words, the ribs 165 at the proximal end of locking element 30 can have a profile and/or spacing so as to make those ribs more compliant than the ribs 165 at the distal end of locking element 30. This will result in the proximal section of locking element 30 being more easily compressed than the distal section of locking element 30 or, stated another way, it will result in the proximal section of locking element 30 providing less expansion to the body of knotless suture anchor 10 than the distal section of locking element 30. This can be desirable in certain circumstances, since the soft cancellous tissue located in the interior portion of a bone (i.e., adjacent to the distal end of suture anchor 10) requires greater anchor expansion than the hard cortical tissue located at the outer portion of a bone (i.e., adjacent to the proximal end of the suture anchor). Hence, by forming locking element 30 so that the ribs on the proximal end of the locking element 30 have a higher compliance than the ribs on the distal end of the locking element 30, proximal movement of locking element 30 within the body of the knotless suture anchor 10 will cause greater expansion of the anchor body adjacent the soft cancellous bone and lesser anchor expansion adjacent the hard cortical bone. More compliant ribs on the proximal end of the locking element 30 may also enable locking element 30 to be more effective in highly dense bone, where such bone density (and less compliant ribs) can combine to prevent proximal movement of the locking element. Thus it will be seen that it can be desirable to vary the spacing between ribs 165, and/or to vary the dimensions of the ribs themselves, so as to provide desired characteristics to locking element 30 and hence to knotless suture anchor 10. See, for example, FIGS. 39-41, which show additional various spacings between the ribs 165 and/or various dimensions for the ribs 165.

Figure 42:
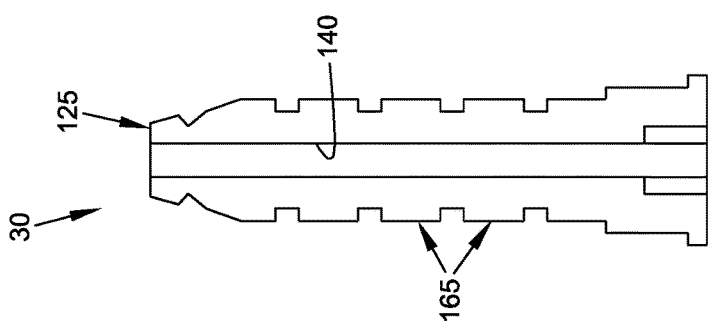

In addition, if desired, distal section 145 of bore 140 of locking element 30 may be omitted, and bore 140 may open on distal end surface 125 of locking element 30, as shown in FIG. 42.

Figure 44:
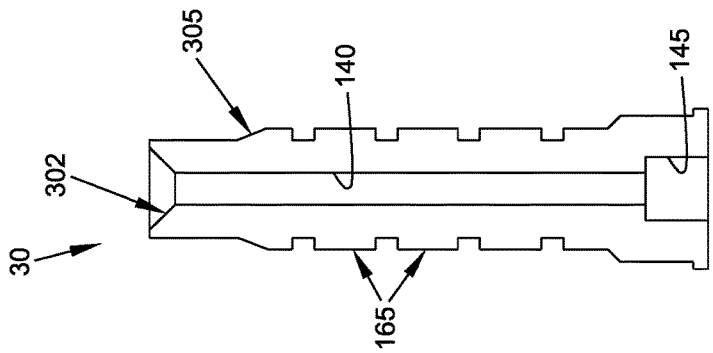
Figure 43:
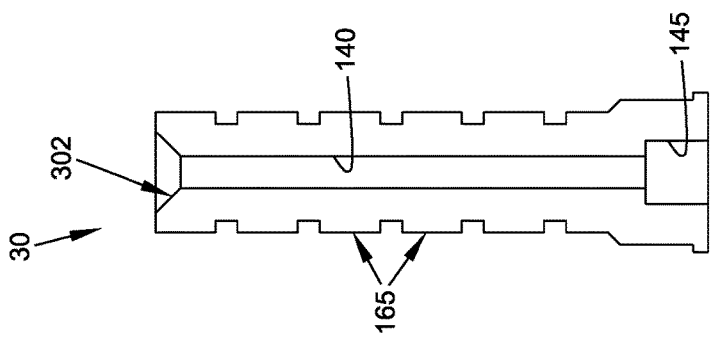

Furthermore, weakened section 132 of locking element 30 may be omitted from the proximal end of locking element 30, as shown in FIGS. 43 and 44. In place of weakened section 132, an internal chamfer 302 of bore 140 prevents a portion of locking element 30 from breaking off when pull rod 35 exits the proximal end of bore 140. This construction can be advantageous, since when pull rod 35 is drawn through bore 140 of locking element 30, it pulls through cleanly, with no debris being created.

Also, if desired, the distalmost rib 165 of locking element 30 may be tapered, e.g., as shown at 305 in FIG. 44, so as to facilitate passage of locking element 30 into proximal section 70 of stepped bore 60 of body 25 of knotless suture anchor 10.

Figure 45:
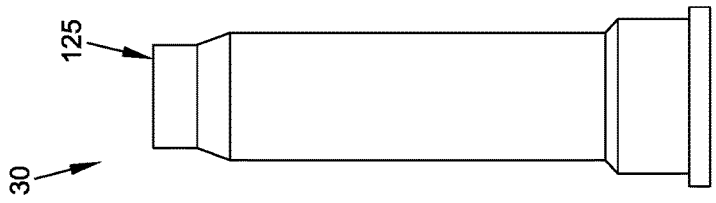

Or, if desired, ribs 165 may be omitted entirely, as shown in FIG. 45.

Figure 47:
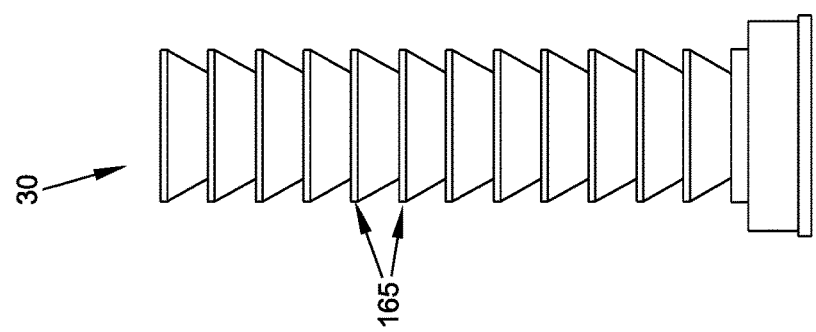
Figure 46:
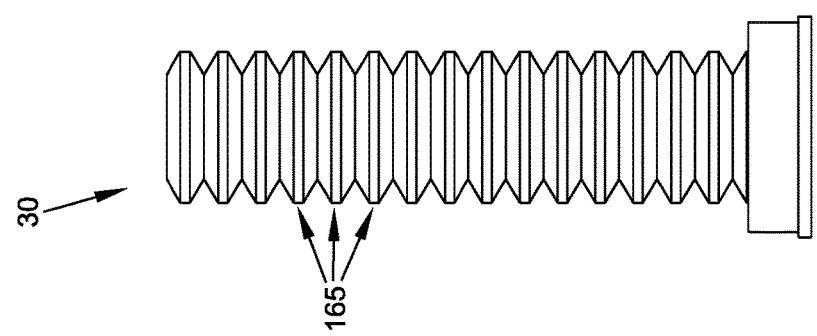
Figure 48:
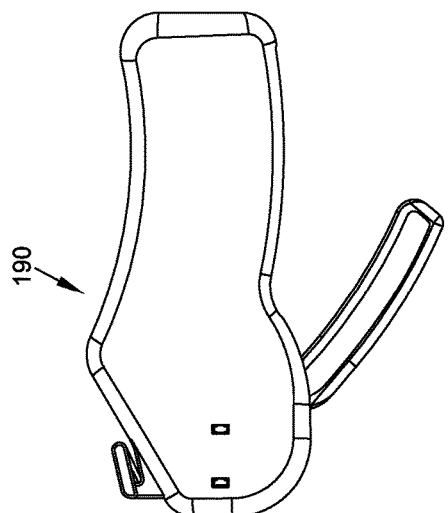
FIGS. 48-59 are schematic views showing an alternative form of knotless suture anchor system formed in accordance with the present invention, wherein FIGS. 48, 49, 52, 54, 55 and 58 comprise side views, and FIGS. 50, 51, 53, 56, 57 and 59 comprise top views.
Figure 49:
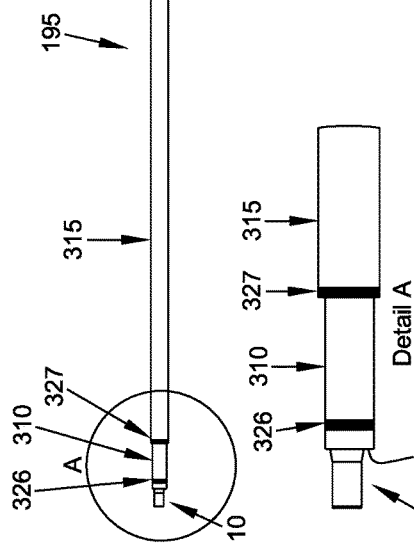
Figure 50:
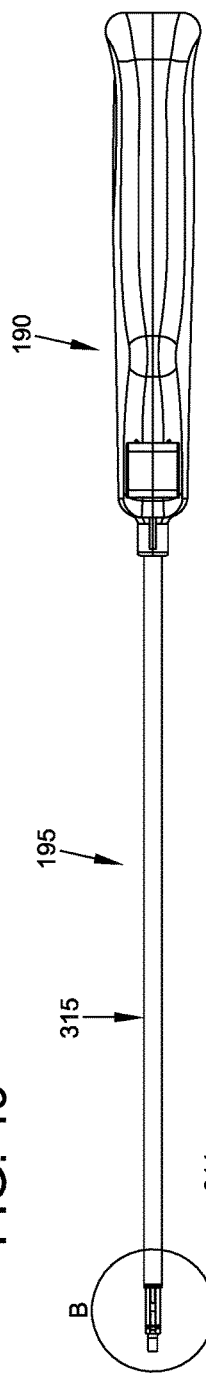
Figure 51:
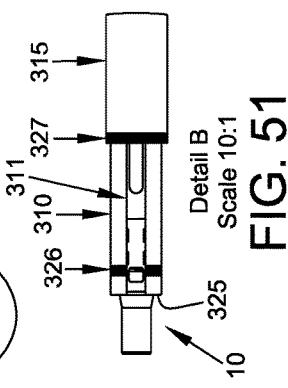
Figure 52:
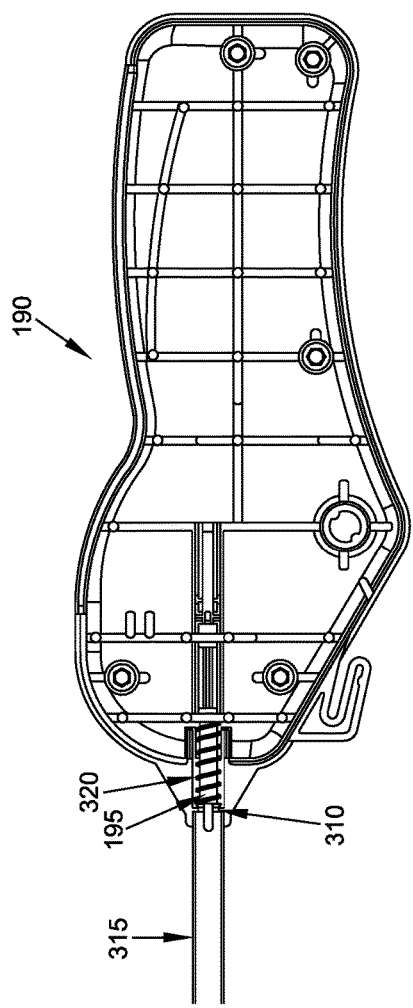
Figure 53:
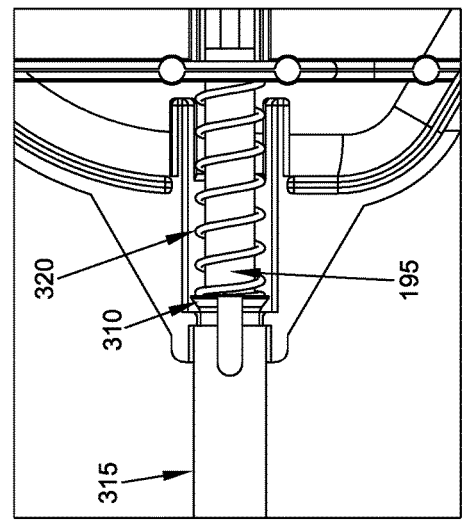
Figure 54:
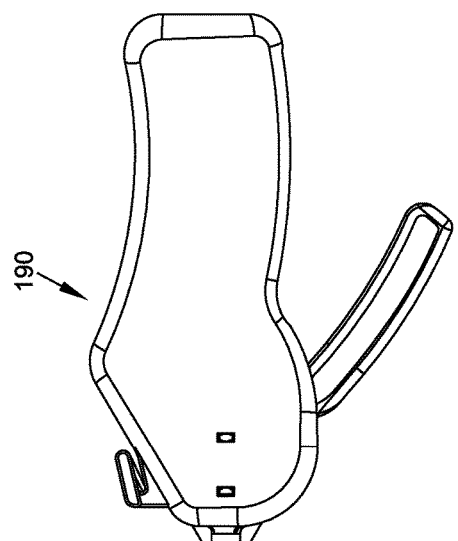
Figure 55:
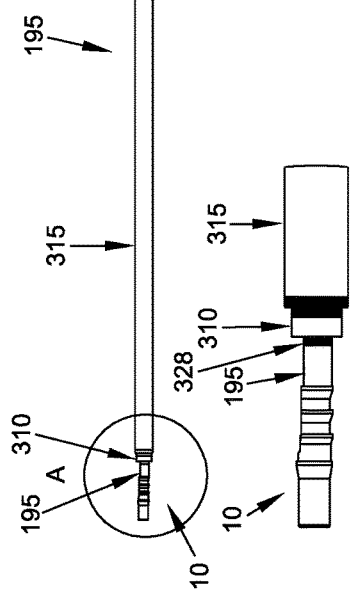
Figure 56:
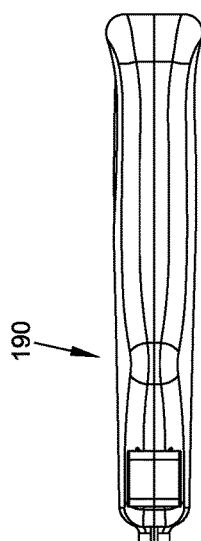
Figure 57:
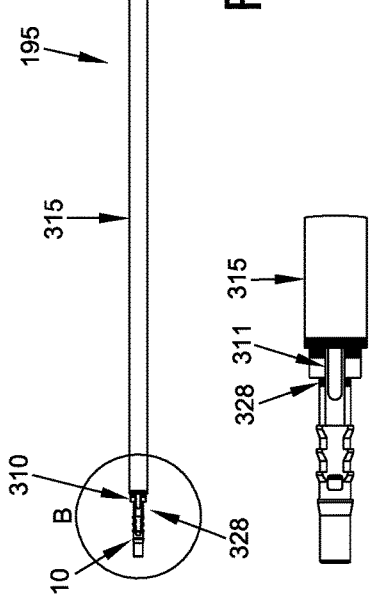
Figure 58:
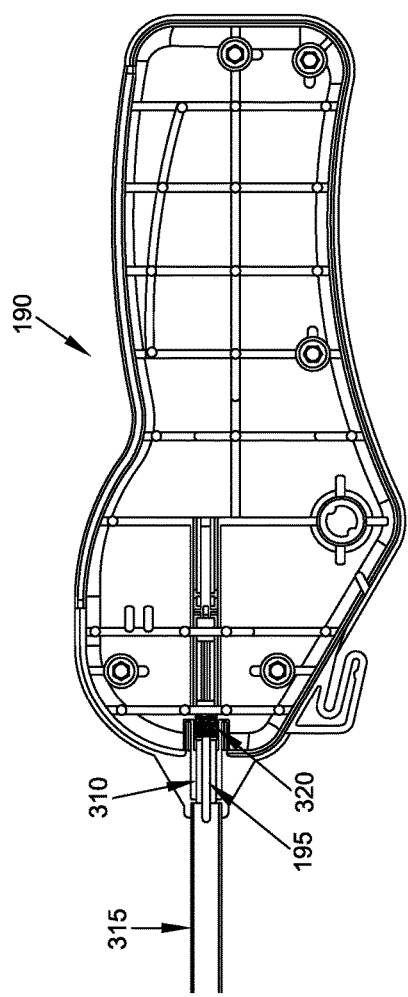
Figure 59:
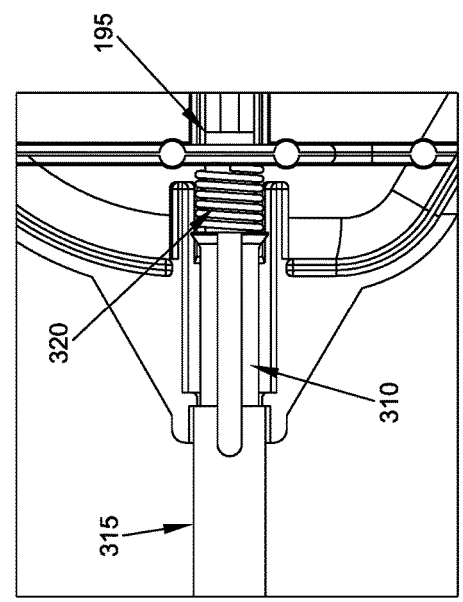

Still other configurations for locking element 30, including variations of ribs 165, are shown in FIGS. 46 and 47. FIG. 46 depicts sharper ribs 165 to further enhance engagement of suture. FIG. 47 depicts ribs 165 with ratchet teeth profiles so as to increase the grip of the ribs on the suture. More particularly, the suture passing through the suture anchor is typically secured to soft tissue, and the elasticity of that soft tissue tends to draw the suture passing through the suture anchor in a distal direction (i.e., out side opening 90). Therefore, by forming ribs 165 of locking element 30 with the structure shown in FIG. 47, the sharp proximal edges of ribs 165 will bear into the suture when the suture is drawn in the distal direction. As noted above, proximal section 70 of stepped bore 60 preferably has a textured interior wall so as to facilitate engagement with locking element 30 and a suture S disposed between locking element 30 and proximal section 70 of stepped bore 60. In one preferred form of the invention, threads 72 are formed on the inner wall of proximal section 70 of stepped bore 60 (see FIGS. 22, 24, 28, 30-34 and 36). However, other surface features may be provided on the inner wall of proximal section 70 to ensure sufficient securement with locking element 30 and suture S, e.g., ribs, knurling, etc.

FIGS. 47A and 47B show another possible construction for locking element 30. More particularly, in FIGS. 22, 24, 25, 28, 30-34, 36, 37 and 42, locking element 30 is shown having a weakened section 132 at its proximal end, wherein the weakened section 132 may be formed by a circumferential groove 133. Alternatively, weakened section 132 of locking element 30 can be formed by reconfiguring stepped bore 140 so that it has a long distal section 145 and a short proximal section 150, in the manner shown in FIGS. 47A and 47B. In this form of the invention, when a sufficient proximal force is applied to pull rod 35, weakened section 132 of locking element 130 will break away from the remainder of locking element 30, in the manner shown in FIG. 47B. In this embodiment, locking element 30 travels in a proximal direction within body 25 so as to expand body 25 and lock suture S to knotless suture anchor 10; however, the threshold force of disengaging pull rod 35 from body 25 is the force at which weakened section 132 of locking element 130 breaks away from the remainder of locking element 30 (rather than the force at which pull rod 35 pulls through bore 140 of locking element 30).

In some cases the suture anchor may be subjected to transverse forces as it is advanced towards, and/or inserted into, the bone hole. This is particularly true where the suture anchor must be advanced through a tight corridor (e.g., such as in arthroscopic surgery), or along a tortuous path (e.g., such as when being advanced to a labral repair site within the hip), since in these situations the suture anchor may accidentally bump into intervening structures and/or the suture anchor may need to turn along a curved sheath during insertion. When this occurs, the suture anchor may be damaged and/or moved out of alignment with its inserter, etc., which can result in ineffective anchor placement in the bone.

Accordingly, in another embodiment of the present invention, and looking now at FIGS. 48-59, means are provided to shield and mechanically support knotless suture anchor 10 as it is advanced towards, and/or inserted into, the bone hole. More particularly, in this form of the invention, inserter 15 comprises a retractable sheath 310 which is co-axial with, and external to, the aforementioned inserter shaft 195. Inserter 15 also comprises an overtube 315. In this form of the invention, shaft 195 is secured to handle 190 (FIG. 53), retractable sheath 310 is coaxially mounted about shaft 195 and spring-biased in a distal direction by a compression spring 320, and overtube 315 is coaxially mounted about retractable sheath 310 and secured to handle 190. Preferably, when retractable sheath 310 is under the influence of compression spring 320, the distal end surface 325 of retractable sheath 310 is disposed proximal to the distal end of knotless suture anchor 10, but distal to the proximal end of knotless suture anchor 10 (see FIGS. 49 and 51). More preferably, the distal end of retractable sheath 310 is located between the midpoint of knotless suture anchor 10 and the distal end of knotless suture anchor 10. In this way, retractable sheath 310 can cover, and hence protect, the major length of knotless suture anchor 10 as the knotless suture anchor is advanced to the surgical site, but still expose the distal end of knotless suture anchor 10 so as to facilitate insertion of the knotless suture anchor into a bone hole. See FIGS. 48-53. However, when retractable sheath 310 is forced proximally, against the power of compression spring 320, knotless suture anchor 10 is completely exposed. See FIGS. 54-59. Preferably retractable sheath 310 and overtube 315 have distal markings 326 and 327, respectively, which provide indication of anchor depth. For example, when markings 326 and 327 align, the anchor is at the preferred depth. Additionally, retractable sheath 310 preferably has a slot 311 extending from its distal end (see FIGS. 51 and 57) to allow suture to pass from within retractable sheath 310 (i.e., from knotless suture anchor 10 and/or shaft 195) to outside retractable sheath 310. Slot 311 is preferably rotationally aligned with side opening 90 in knotless suture anchor 10 and opening 227 in the side wall of shaft 195.

In use, and looking now at FIGS. 60-63, retractable sheath 310 is initially disposed in its distal position, i.e., compression spring 320 actively pushes the proximal end of retractable sheath 310 away from handle 190, so that retractable sheath 310 covers the majority of the length of knotless suture anchor 10, but leaves the distal tip of the knotless suture anchor 10 exposed for easy locating into a bone hole H. Thereafter, when knotless suture anchor 10 is to be deployed into the bone hole H, the knotless suture anchor 10 is advanced (e.g., through an arthroscopic cannula) to the surgical site, with retractable sheath 310 covering, and protecting, the knotless suture anchor 10 during such advancement. Overtube 315 prevents retractable sheath 310 from prematurely retracting while the knotless suture anchor 10 is being delivered to the bone site. For example, the knotless suture anchor 10 may be passed through a cannula with an elastomeric septum; the septum, being grip-like in nature, will tend to grip the retractable sheath 310 and, consequently, retract the retractable sheath, thus removing some or all of the protection it was providing to the knotless suture anchor 10. Overtube 315 provides protection against this occurrence as the septum will bear against the overtube 315 (it being the outermost surface) instead of retractable sheath 310. Then the exposed distal tip of knotless suture anchor 10 is placed into bone hole H (FIGS. 60 and 61), with the distal end of retractable sheath 310 contacting the outer surface of the bone B. In this position, retractable sheath 310 contacts the outer surface of the bone B about the perimeter of the bone hole H and provides additional mechanical support against any transverse forces that may be applied to the knotless suture anchor 10 from the inserter 15, for example, if there is a misalignment between the arthroscopic portal and the axis of the bone hole H. The knotless suture anchor 10 is then advanced into the bone hole H. This is done by moving inserter 15 distally. As inserter 15 moves distally, shaft 195 advances the knotless suture anchor 10 into the bone hole H while the engagement of retractable sheath 310 with the outer surface of the bone B causes the retractable sheath 310 to remain stationary relative to the bone B. See FIGS. 62 and 63. Under this action, the power of compression spring 320 is overcome and the advancing handle 190 moves shaft 195 distally within retractable sheath 310. In other words, pushing handle 190 distally moves shaft 195 distally, while compression spring 320 allows retractable sheath 310 to remain seated on the outer surface of the bone B and retract into the advancing handle 190. During advancement of knotless suture anchor 10 into the bone hole H, retractable sheath 310 continues to provide mechanical support to the knotless suture anchor 10 as the knotless suture anchor 10 is pressed further into the bone hole. In this manner, retractable sheath 310 protects and supports knotless suture anchor 10 during delivery into the bone hole H.

In a preferred embodiment, retractable sheath 310 and overtube 315 are formed out of biocompatible materials such as stainless steel. In an alternative embodiment, retractable sheath 310 is formed out of a transparent polymer. In this embodiment, a distal marking 328 (FIG. 55) on the shaft 195 can be visualized through the transparent retractable sheath 310 to provide visual indication of anchor depth.

In another embodiment, the spring 320 may be sufficiently strong so as to overcome inadvertent retraction of retractable sheath 310 during delivery; hence, in this form of the invention, overtube 315 may be omitted.

In another embodiment of the present invention, and looking now at FIGS. 63A-63G, there is shown an inserter 15A comprising a retractable sheath 310A. Retractable sheath 310A is generally similar to the retractable sheath 310 discussed above (i.e., retractable sheath 310A is aligned co-axial with, and external to, the aforementioned inserter shaft 195), however, in this form of the invention, retractable sheath 310A can, optionally, be manually retracted, as will hereinafter be discussed in greater detail.

More particularly, in this form of the invention, a shaft 195A (not shown in FIGS. 63A-63G, but analogous to the aforementioned shaft 195) is secured to a handle 190A, retractable sheath 310A is coaxially mounted about shaft 195A, and an overtube 315A is coaxially mounted about retractable sheath 310A and secured to handle 190A. Handle 190A comprises an T-shaped (or L-shaped) slot 322A formed near the distal end of handle 190A. T-shaped (or L-shaped) slot 322A preferably comprises a longitudinally-extending section 323A which runs parallel to the longitudinal axis of shaft 195A and the longitudinal axis of overtube 315A, and a laterally-extending section 324A which is generally perpendicular to the longitudinal axis of shaft 195A. A movable tab 329A extends through T-shaped (or L-shaped) slot 322A and is mounted to the proximal end of retractable sheath 310A, such that movable tab 329A can move within T-shaped (or L-shaped) slot 322A relative to handle 190A. Since movable tab 329A is mounted to the proximal end of retractable sheath 310A, proximal or distal movement of movable tab 329A within longitudinally-extending section 323A of T-shaped (or L-shaped) slot 322A causes retractable sheath 310A to also move proximally or distally, respectively, relative to shaft 195A and overtube 315A. When movable tab 329A is moved laterally (FIGS. 63E, 63F and 63G) within laterally-extending section 324A of T-shaped (or L-shaped) slot 322A, retractable sheath 310A is locked in position relative to shaft 195A and overtube 315A (i.e., retractable sheath 310A cannot move distally or proximally relative to shaft 195A and overtube 315A). If desired, the movable tab 329A can be releasably locked in T-shaped (or L-shaped) slot 322A by a releasable locking mechanism (e.g., a detent, a snap, a recess, etc.) of the sort well known in the art. Such a releasable locking mechanism (e.g., a detent, a snap, a recess, etc.) can be disposed along laterally-extending slot 324A (whereby to releasably lock against movement within laterally-extending slot 324A) and/or such a releasable locking mechanism (e.g., a detent, a snap, a recess, etc.) can be disposed along longitudinally-extending slot 323A (whereby to releasably lock against movement within longitudinally-extending slot 323A, e.g., in a position intermediate its distalmost and proximalmost positions).

Alternatively, if desired, the T-shaped (or L-shaped) slot 322A can be replaced by a linear slot and the aforementioned releasable locking mechanism (e.g., a detent, a snap, a recess, etc.) can be relied on to releasably lock retractable sheath 310A in its proximal position along such a linear slot (or, if desired, in a position intermediate its distalmost and proximalmost positions).

Figure 63A:
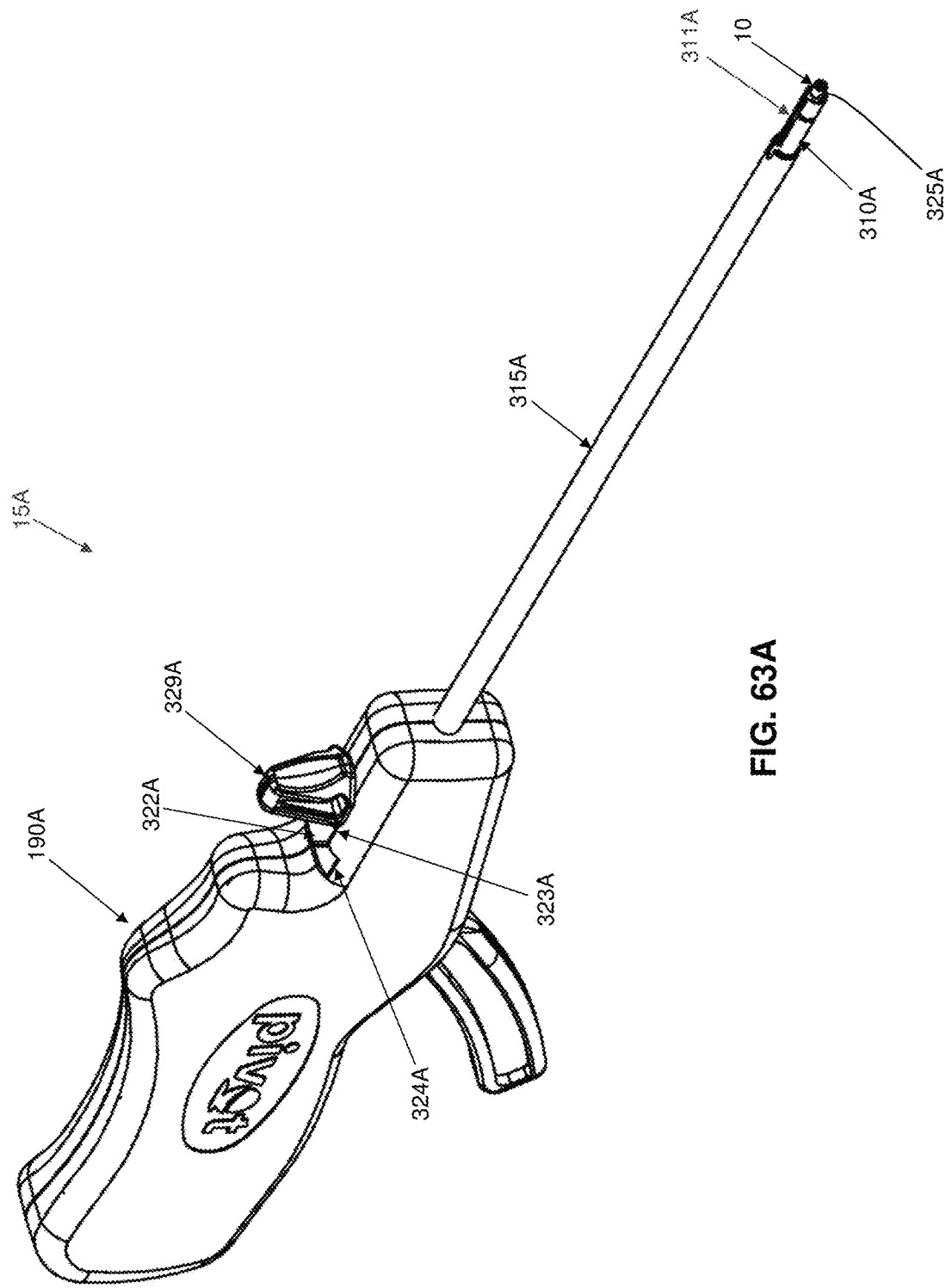
FIGS. 63A-63G are schematic views showing an alternative form of inserter utilizing a retractable sheath.
Figure 63B:
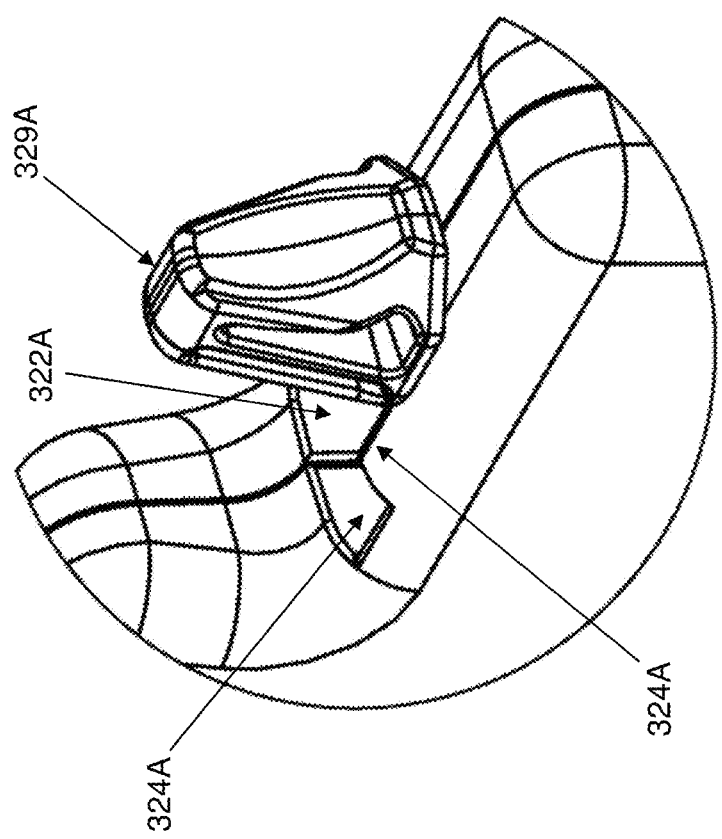
Figure 63C:
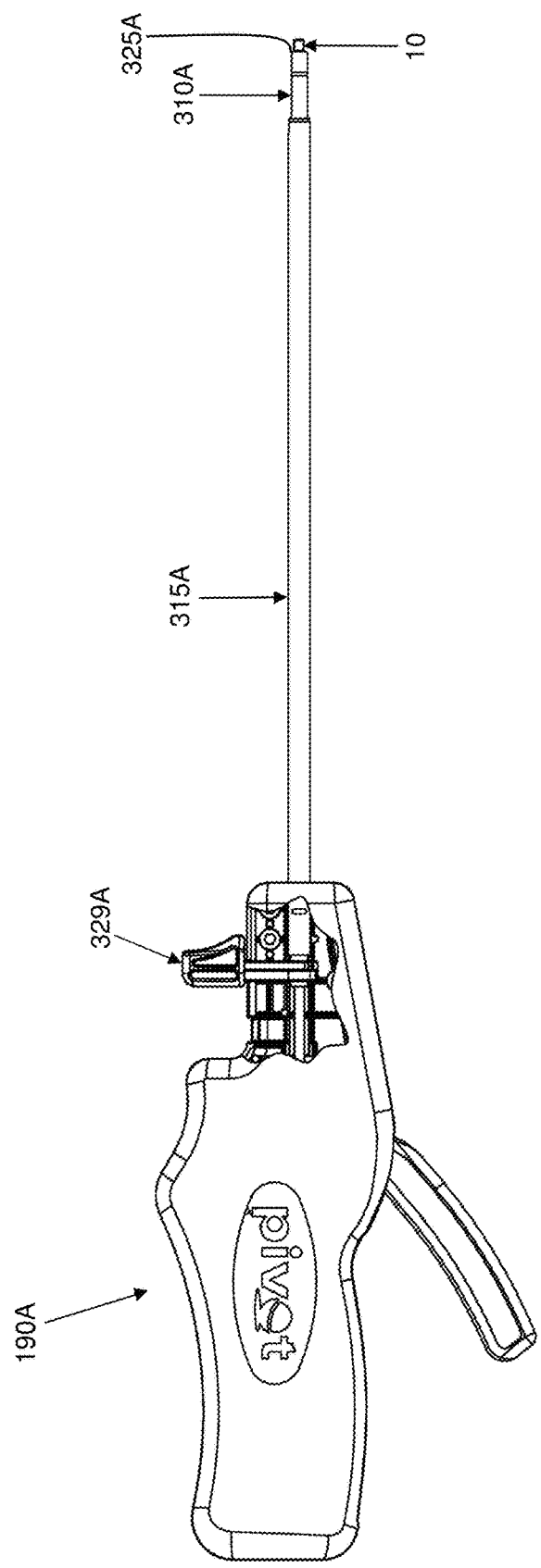
Figure 63D:
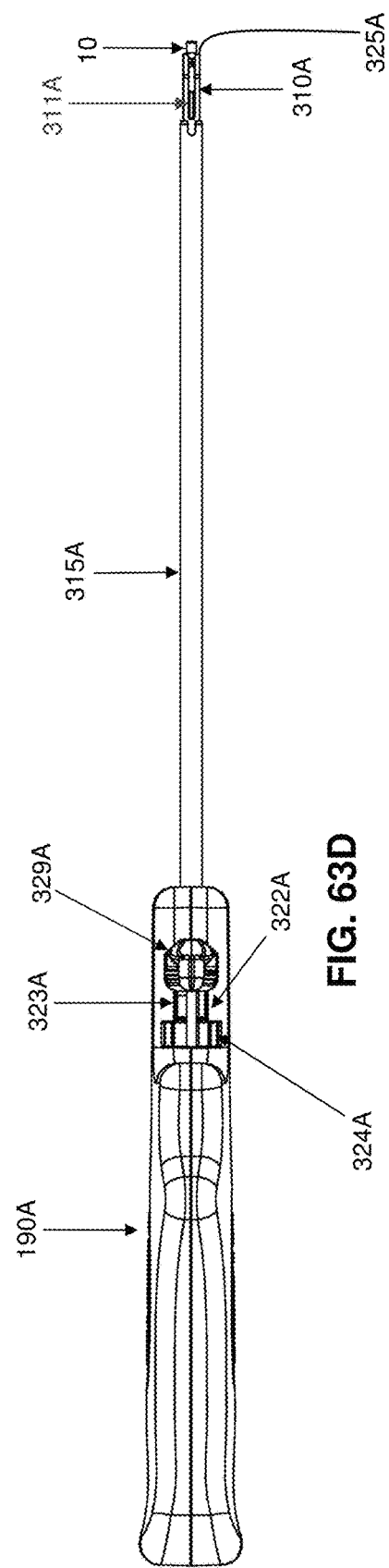
Figure 63E:
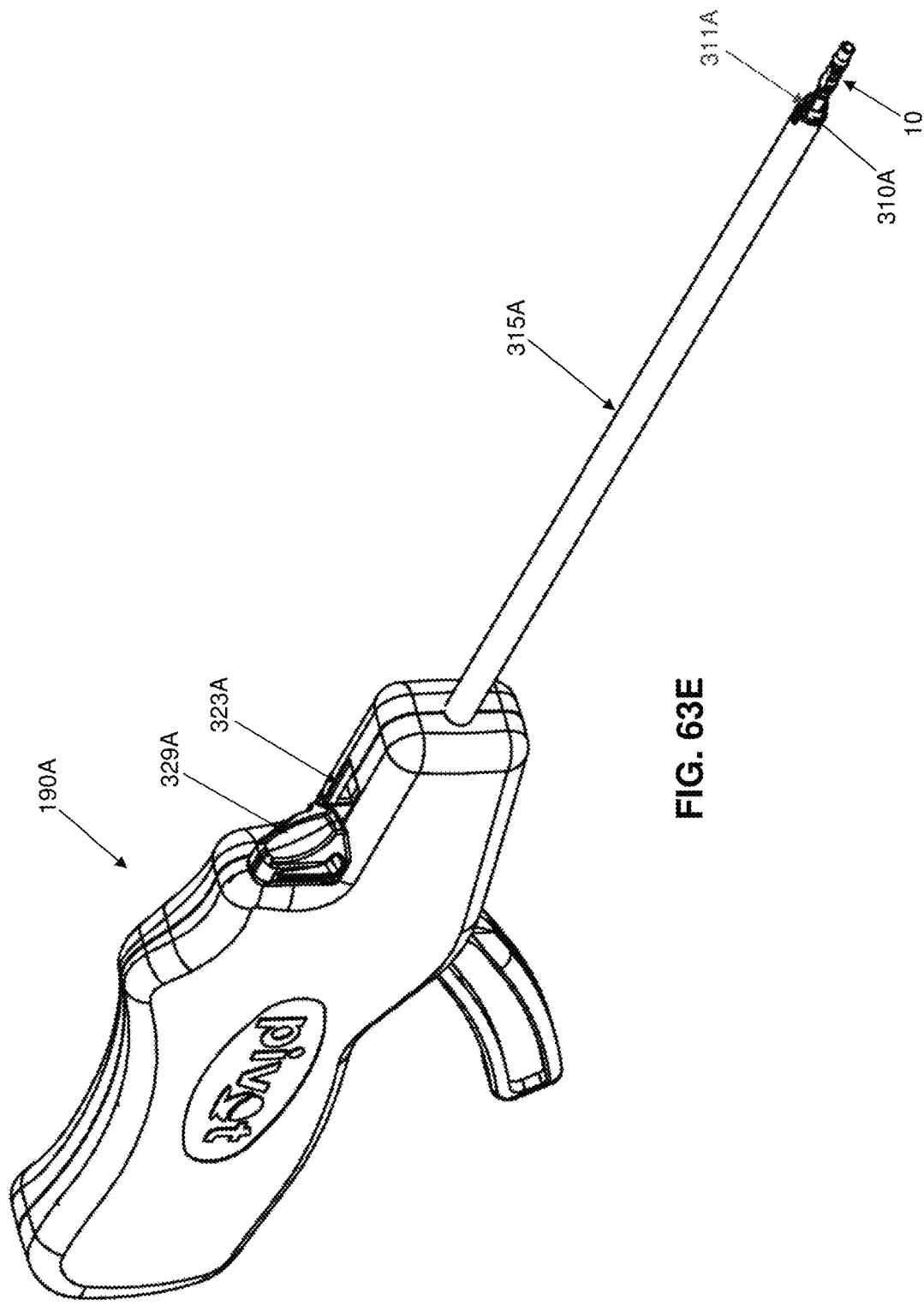
Figure 63F:
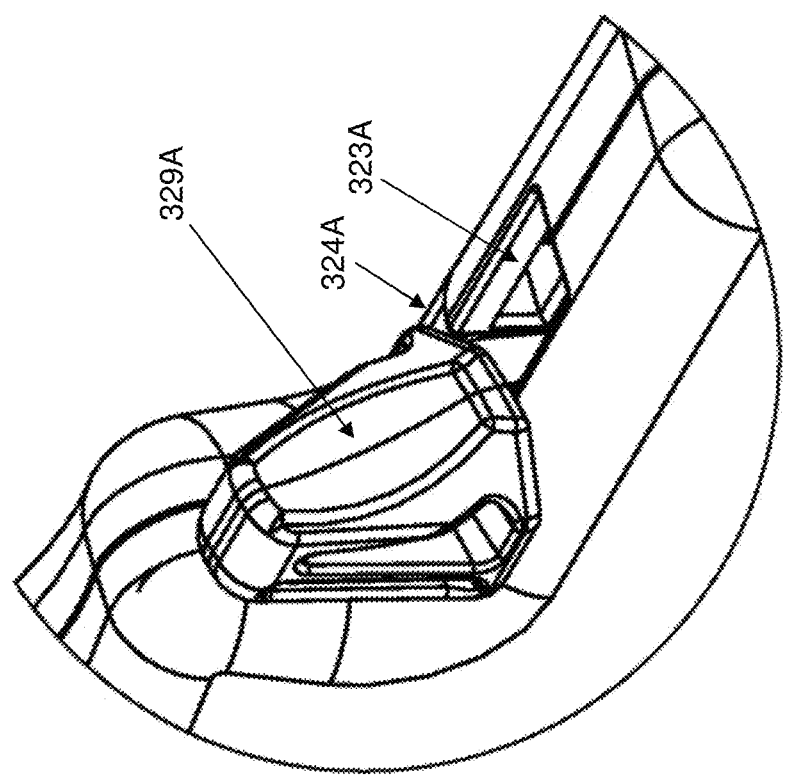
Figure 63G:
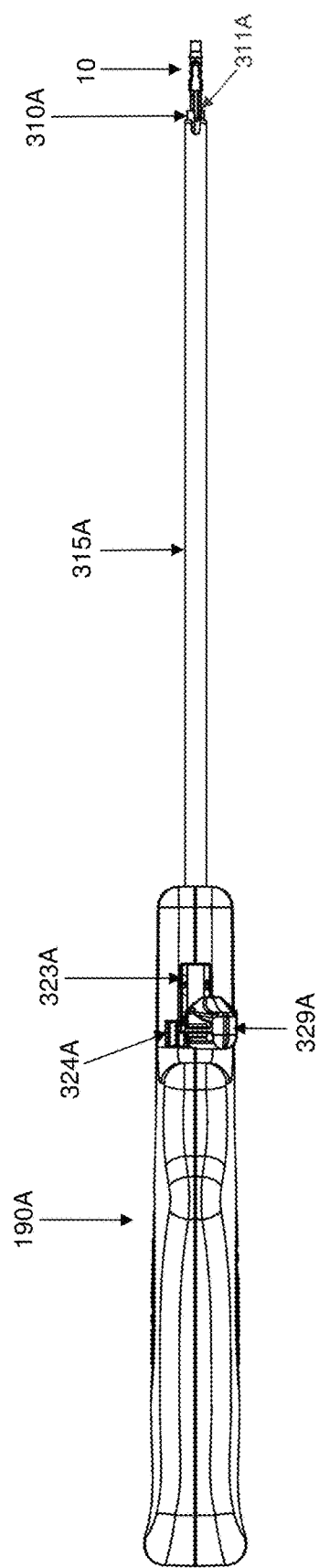

Preferably, when movable tab 329A is moved distally within longitudinally-extending section 323A of T-shaped (or L-shaped) slot 322A to its most distal position (FIG. 63D), the distal end surface 325A of retractable sheath 310A is disposed proximal to the distal end of knotless suture anchor 10, but distal to the proximal end of knotless suture anchor 10 (see FIGS. 63A, 63C and 63D). More preferably, the distal end surface 325A of retractable sheath 310A is located between the midpoint of knotless suture anchor 10 and the distal end of knotless suture anchor 10. In this way, retractable sheath 310A can cover, and hence protect, the major length of knotless suture anchor 10 as the knotless suture anchor is advanced to the surgical site but still expose the distal end of knotless suture anchor 10 so as to facilitate insertion of the knotless suture anchor 10 into a bone hole.

However, when retractable sheath 310A is moved proximally (e.g., by moving movable tab 329A proximally within longitudinally-extending section 323A of T-shaped (or L-shaped) slot 322A), knotless suture anchor 10 is completely exposed (see FIGS. 63E and 63G), such that knotless suture anchor 10 can be viewed before, during or even after insertion into a bone hole.

It should be appreciated that the manual retraction of retractable sheath 310A using movable tab 329A is an optional feature of inserter 15A. In other words, the user can selectively choose whether to (i) manually retract retractable sheath 310A by manually moving movable tab 329A, or (ii) retract retractable sheath 310A via engagement of retractable sheath 310A with the bone (i.e., allow retractable sheath 310A to retract against compression spring 320A as handle 190A is moved distally). The user may, for example, choose to deliver the anchor 10 without manual retraction of the retractable sheath 310A; in this mode, the device operates as shown in FIGS. 48-63 and as described above (i.e., via engagement of the distal end of retractable sheath 310A with the bone). Alternatively, the user may choose to manually retract the retractable sheath 310A (i.e., by manually moving the movable tab 329A proximally) to, for example, view the anchor 10. Once retracted, the user may choose to keep the retractable sheath 310A retracted until completion of delivery of anchor 10 into the bone hole. Alternatively, the user may choose to release movable tab 329A, which returns retractable sheath 310A back to covering a portion of anchor 10 (whereupon retractable sheath 310A may thereafter be retracted by engagement with the bone during delivery of the bone anchor into the bone hole).

Although a releasable locking mechanism has been described above to lock movable tab 329A in a proximal position (e.g., by moving movable tab 329A into laterally-extending section 324A of T-shaped (or L-shaped) slot 322A), the user may choose not to lock movable tab 329A in a proximal position; in this scenario, the user must continue to pull movable tab 329A proximally so as to keep movable tab 329A (and hence, retractable sheath 310A) in a proximal position (i.e., to keep retractable sheath 310A retracted proximally so as to expose anchor 10).

Although movable tab 329A has been described as being moved proximally to expose the full length of anchor 10, the user may choose to only partially retract retractable sheath 310A. For example, the user may choose to view only a portion of the length of anchor 10, or may need to retract retractable sheath 310A for another purpose such as viewing the bone hole or to release a suture which may be pinched between the distal end of the retractable sheath 310A and the bone surface. In this situation, the user pulls movable tab 329A proximally along only a portion of the length of longitudinally-extending section 323A of T-shaped (or L-shaped) slot 322A.

If desired, retractable sheath 310A and overtube 315A may have distal markings (analogous to the distal markings 326 and 327 discussed above) formed thereon, respectively, which provide indication of anchor depth. Alternatively, markings (not shown) may be formed on handle 190A and/or on movable tab 329A which provide an indication of anchor depth. Additionally, retractable sheath 310A preferably has a slot 311A extending proximally from its distal end (see FIGS. 63A, 63D, 63E and 63G) to allow suture to pass from within retractable sheath 310A (i.e., from knotless suture anchor 10 and/or shaft 195A) to outside retractable sheath 310A. Slot 311A is preferably rotationally aligned with side opening 90 in knotless suture anchor 10 and opening 227A (not shown in FIGS. 63A-63G, but analogous to the aforementioned opening 227 in shaft 195) in the side wall of shaft 195A.

Figure 66:
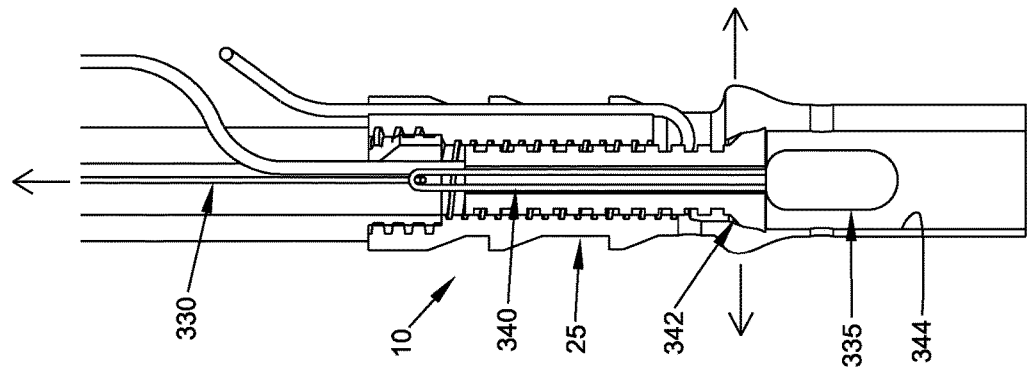
FIGS. 64-66 are schematic views showing an alternative form of knotless suture anchor and the distal end of its associated inserter.
Figure 65:
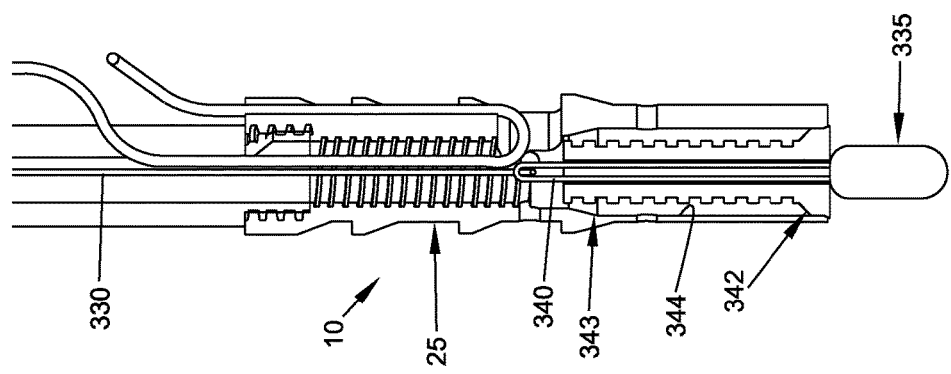
Figure 64:
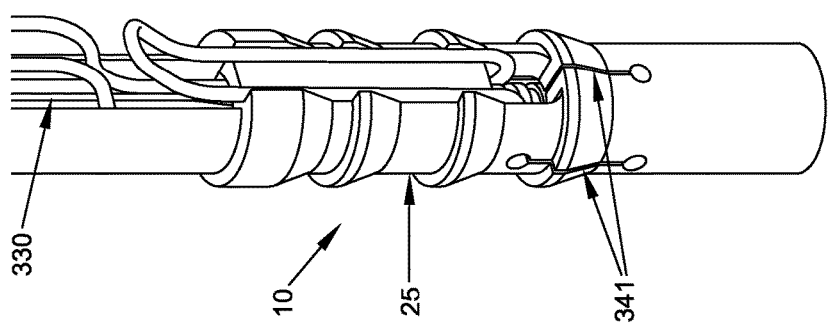

In another form of the invention, and looking now at FIGS. 64-66, pull rod 35 may be replaced by a pull suture 330, an enlargement 335 and a connecting suture 340 connecting pull suture 330 to enlargement 335. In this form of the invention, pulling proximally on pull suture 330 causes proximal movement of enlargement 335, whereby to cause proximal movement of locking element 30. As in the preceding constructions, such proximal movement of locking element 30 causes radial expansion of the body 25 of knotless suture anchor 10 so as to secure the knotless suture anchor 10 to surrounding bone, and captures the suture S within the proximal section 70 of stepped bore 60, whereby to secure the suture S to the knotless suture anchor (and hence to the bone within which the knotless suture anchor 10 is secured). After proximal movement of locking element 30, connecting pull suture 330 is detached from connecting suture 340. One or more slits 341 may be formed in the side wall of the anchor body 25 so as to weaken the side wall and provide enhanced expansion of the anchor body 25 against adjacent bone. In this form of the invention, locking element 30 preferably comprises an enlargement 342 at its distal end which has a larger diameter than the tapered proximal section 343 of bore 344. When enlargement 342 of locking element 30 is wedged into tapered proximal section 343 of bore 344, the anchor body 25 expands at slits 341.

In another form of the invention, and looking now at FIGS. 67-69, the construction is similar to the construction shown in FIGS. 64-66, except that instead of passing suture S out opening 227 in the side wall of shaft 195, suture S passes out a second side opening 345 in knotless suture anchor 10. Preferably side opening 345 in knotless suture anchor 10 is diametrically opposed to side opening 90 in knotless suture anchor 10. Suture S may also be passed through the loop of connecting suture 340 so that suture S is captured and held secured to the proximal end of the locking element during proximal movement of the locking element (i.e., suture S does not get displaced between the locking element 30 and anchor body). In addition, if desired, enlargement 335 may extend out the distal end of knotless suture anchor 10. Again, with this construction, pulling proximally on pull suture 330 causes proximal movement of enlargement 335, whereby to cause proximal movement of locking element 30. Such proximal movement of locking element 30 causes radial expansion of the body 25 of knotless suture anchor 10 so as to secure the knotless suture anchor to surrounding bone, and captures the suture within the proximal section 70 of stepped bore 60, whereby to secure the suture to the knotless suture anchor (and hence to the bone within which the knotless suture anchor is secured).

Figure 71:
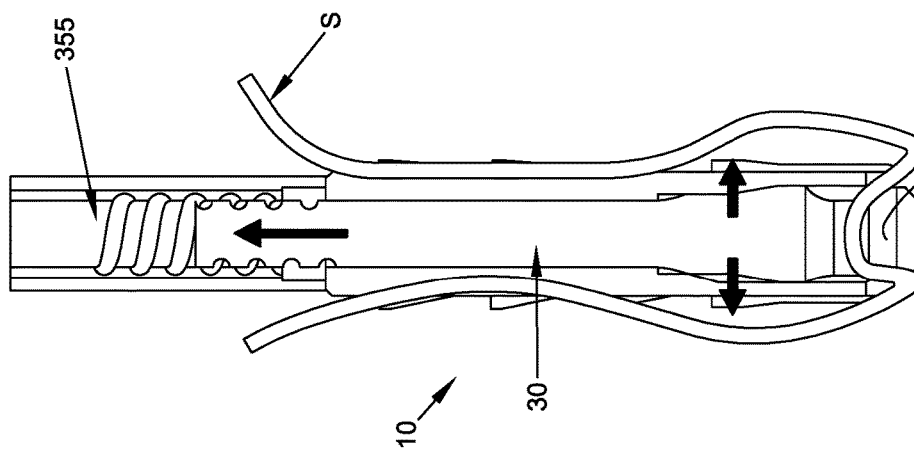
FIGS. 70 and 71 are schematic views showing another alternative form of knotless suture anchor and the distal end of its associated inserter.
Figure 70:
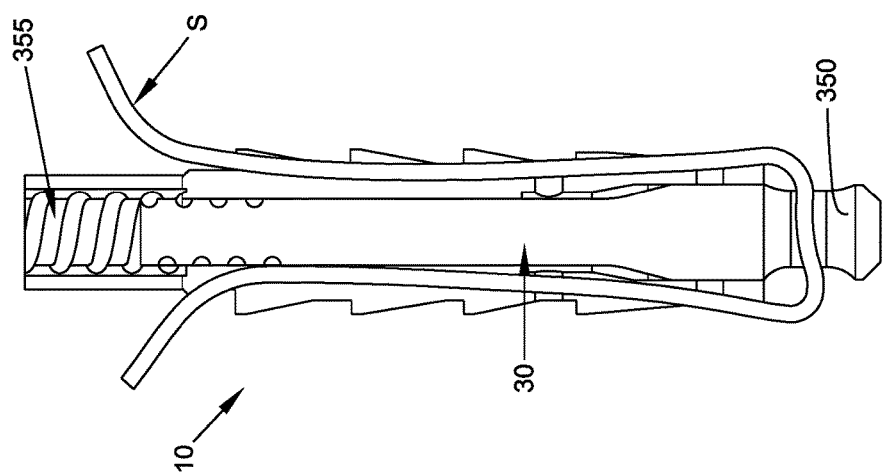
Figure 90:
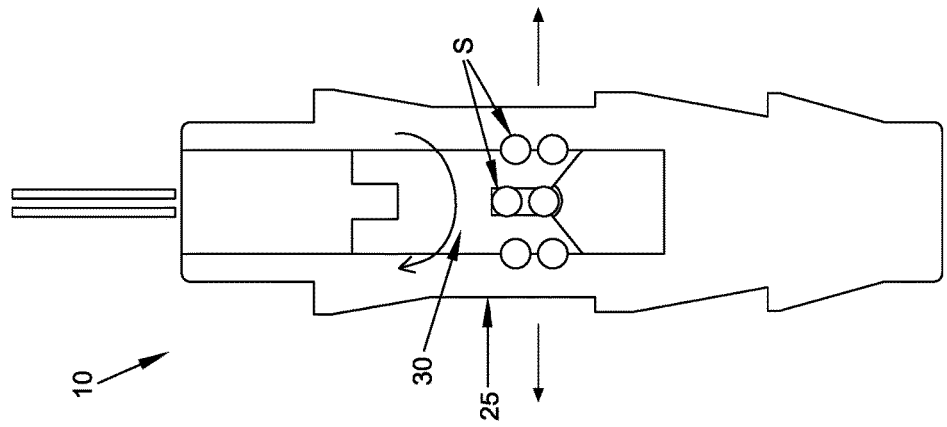
Figure 89:
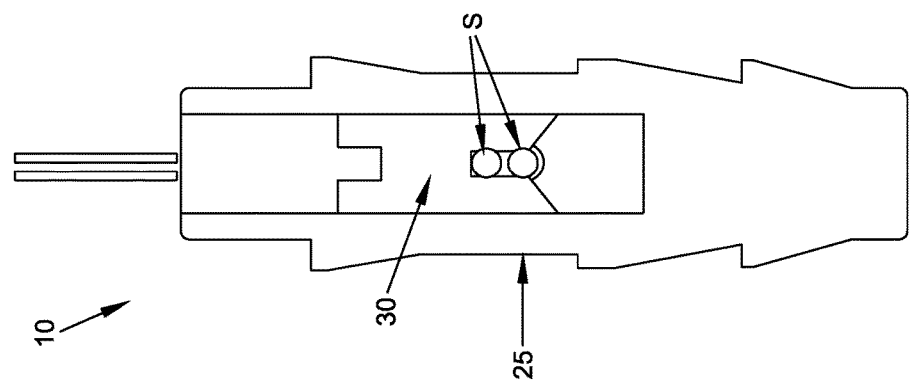
Figure 88:
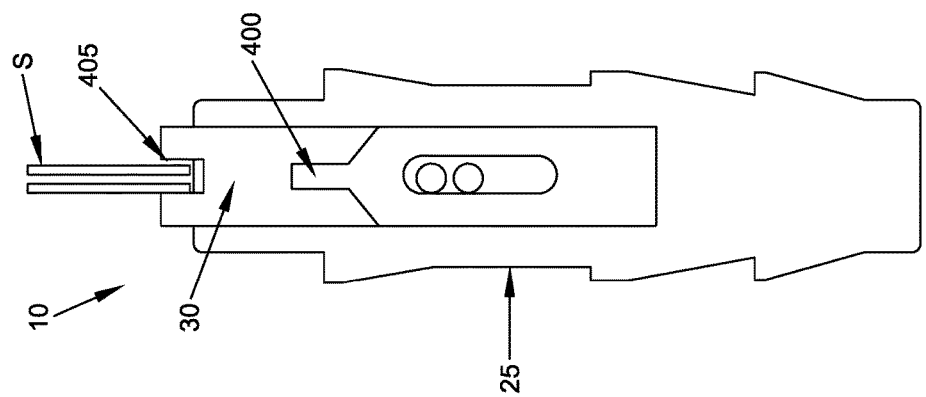

In still another form of the invention, and looking now at FIGS. 70 and 71, locking element 30 is sized to extend out the distal end of knotless suture anchor 10, and comprises a crossbore 350 extending therethrough. In this form of the invention, instead of passing suture S through side opening 90 in knotless suture anchor 10 and out opening 227 in the side wall of shaft 195 (in the manner of FIGS. 31-34), or through side opening 90 in knotless suture anchor 10 and out side opening 345 in knotless suture anchor 10 (in the manner of FIGS. 67-69), suture S is looped through crossbore 350 and, when locking element 30 is thereafter pulled proximally to expand suture anchor 10, suture S is pulled into the distal end of the knotless suture anchor, whereby to bind suture S to the knotless suture anchor. If desired, locking element 30 may be moved proximally by a pull rod 355 (which may be connected to locking element 30 by a screw connection such as is shown in FIGS. 70 and 71). Thus it will be seen that, with this construction, pulling proximally on pull rod 355 causes proximal movement of locking element 30. Such proximal movement of locking element 30 causes radial expansion of the body 25 of knotless suture anchor 10 so as to secure the knotless suture anchor to surrounding bone, and captures the suture within the distal end of knotless suture anchor 10, whereby to secure the suture to the knotless suture anchor (and hence to the bone within which the knotless suture anchor is secured).

In still another form of the invention, and looking now at FIGS. 72-74, locking element 30 comprises a screw adapted to move distally in order to expand the body of knotless suture anchor 10 and bind suture S to the knotless suture anchor 10. In this form of the invention, locking element 30 is stepped at its proximal end and comprises screw threads 360 on its exterior surface which cooperate with (i) screw threads 365 formed in inserter 15, and (ii) screw threads 370 formed in knotless suture anchor 10. The diameter of the screw threads 360 is larger at the proximal section of the locking element 30 than at the distal section of the locking element 30 (e.g., the locking element 30 may comprise a #1-72 thread proximally and a #0-72 distally) in order to create expansion when the proximal section of the locking element reaches the proximal screw threads 370 formed in the knotless suture anchor 10. Note that in this form of the invention, knotless suture anchor 10 is initially held to inserter 15 by locking element 30, which spans the interface of inserter 15 and knotless suture anchor 10 and simultaneously engages both screw threads 365 in inserter 15 and screw threads 370 in knotless suture anchor 10. It is important to note that, although locking element 30 comprises two different diameter screw threads 360, both diameters of screw threads 360 preferably have the same thread pitch so that distal movement of the locking element does not draw the inserter 15 closer to, or move it further away from, knotless suture anchor 10. In addition to the foregoing, knotless suture anchor 10 comprises a side opening 375 through which suture S passes. In this form of the invention, turning locking element 30 (e.g., with a driver 380) causes distal movement of locking element 30. Such distal movement of locking element 30 causes radial expansion of the body 25 of knotless suture anchor 10 so as to secure the knotless suture anchor 10 to surrounding bone, and captures the suture within the knotless suture anchor 10, whereby to secure the suture to the knotless suture anchor 10 (and hence to the bone within which the knotless suture anchor 10 is secured).

Figure 75:
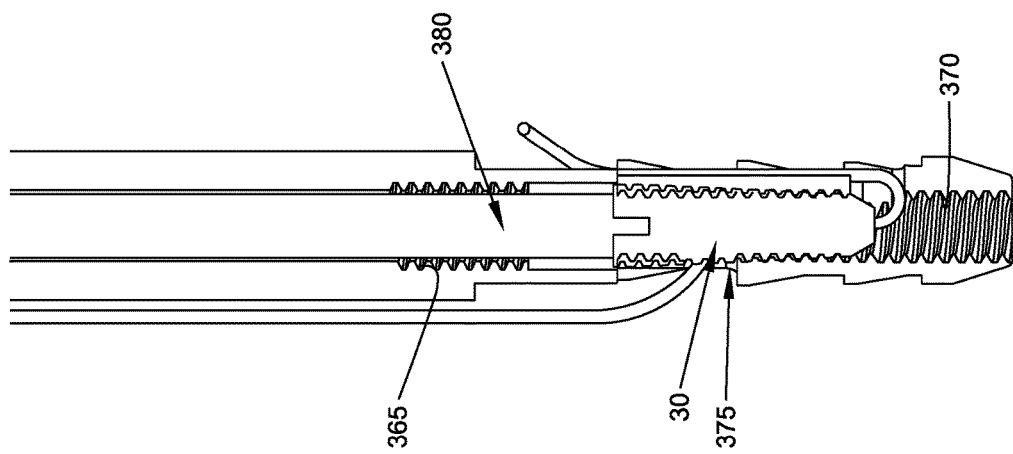
FIGS. 75 and 76 are schematic views showing another alternative form of knotless suture anchor and the distal end of its associated inserter.
Figure 76:
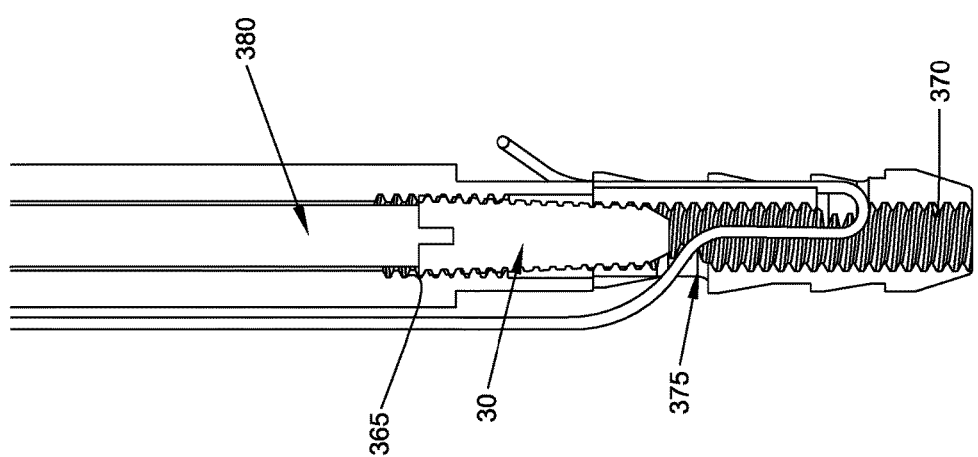

In yet another form of the invention, and looking now at FIGS. 75 and 76, the construction is similar to the construction shown in FIGS. 72-74, except that locking element 30 is tapered along its entire length. Again, in this form of the invention, distal movement of locking element 30 causes radial expansion of body 25 of knotless suture anchor 10 so as to secure the knotless suture anchor to surrounding bone, and captures the suture within the interior of the knotless suture anchor, whereby to secure the suture to the knotless suture anchor (and hence to the bone within which the knotless suture anchor is secured).

Figure 78:
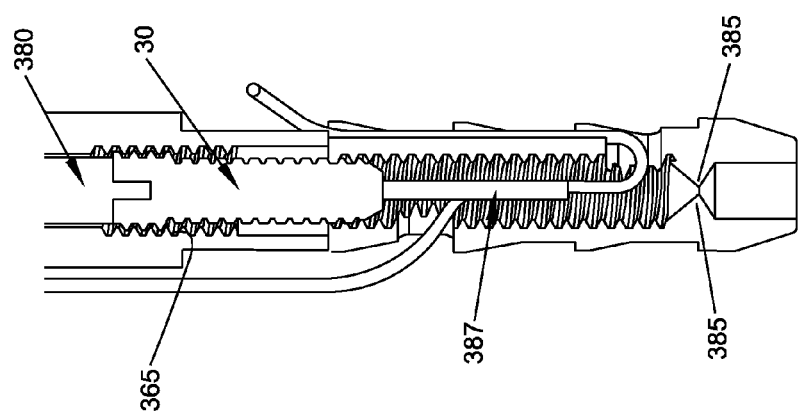
FIGS. 77 and 78 are schematic views showing another alternative form of knotless suture anchor and the distal end of its associated inserter.
Figure 77:
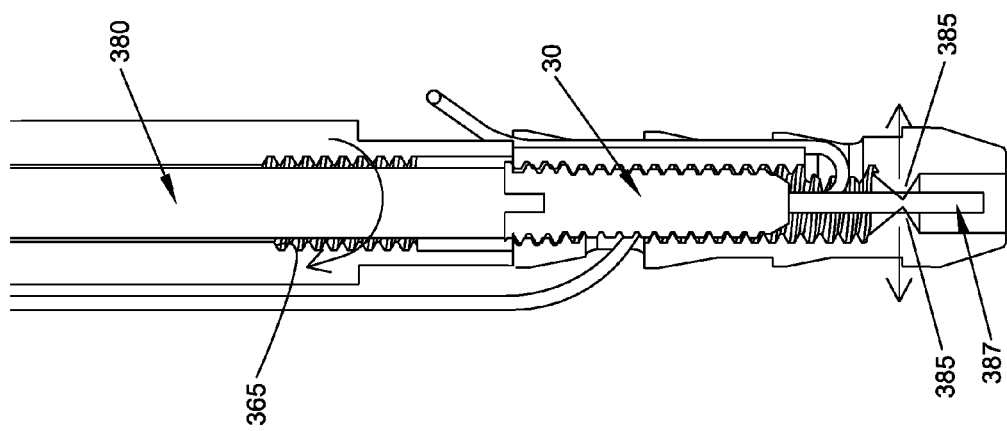

In another form of the invention, and looking now at FIGS. 77 and 78, the construction is again generally similar to the construction shown in FIGS. 72-74, except that locking element 30 is straight along its length (i.e., threads 360 are on a constant diameter) and knotless suture anchor 10 comprises one or more projections 385 which narrow the diameter of the internal bore in the distal section of the knotless suture anchor 10. In this form of the invention, distal movement of locking element 30, which may contain a distal protrusion 387, within knotless suture anchor 10 causes radial expansion of the body of the knotless suture anchor 10 by engaging projections 385 in the distal section of the anchor body so as to secure the knotless suture anchor 10 to surrounding bone, and captures the suture within the interior of the knotless suture anchor 10, whereby to secure the suture to the knotless suture anchor 10 (and hence to the bone within which the knotless suture anchor 10 is secured).

Figure 81:
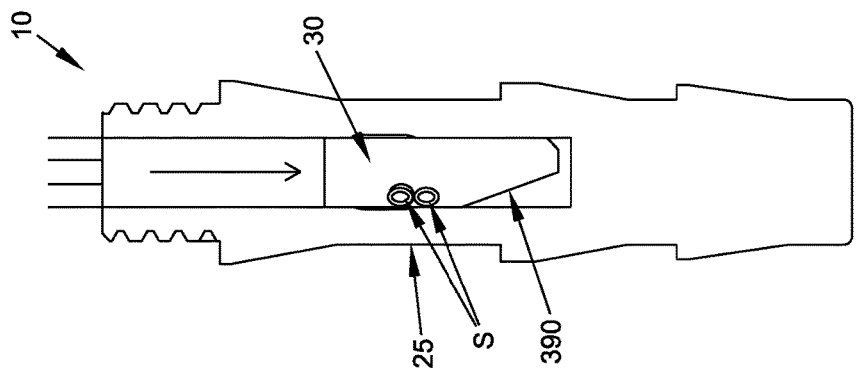
FIGS. 79-81 are schematic views showing another alternative form of knotless suture anchor.
Figure 80:
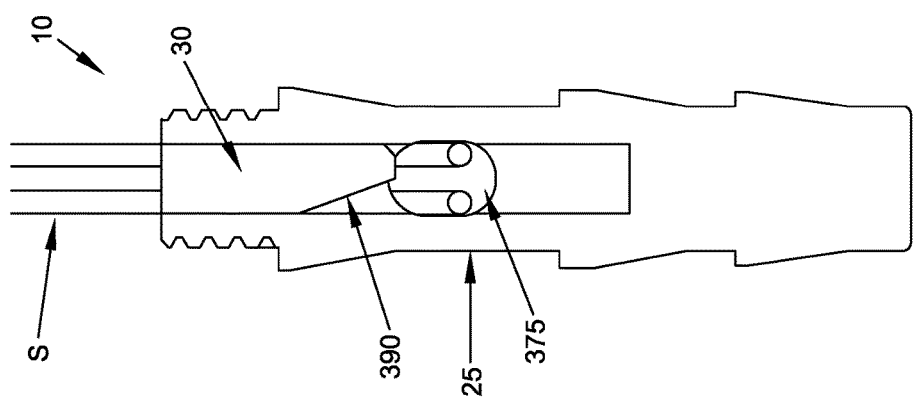
Figure 79:
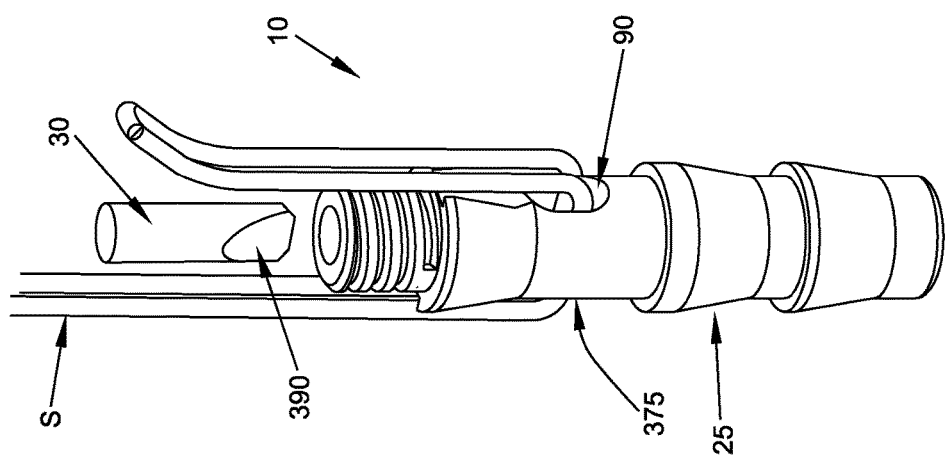

In still another form of the invention, and looking now at FIGS. 79-81, the construction of knotless suture anchor 10 is generally similar to the construction shown in FIGS. 72-74, except that locking element 30 forms an interference fit with surrounding body of the knotless suture anchor 10, whereby to expand the body of the knotless suture anchor 10 and capture suture S to the body of the knotless suture anchor 10. In this form of the invention, locking element 30 may include an inclined surface 390 for facilitating the interference fit with suture S, and side opening 375 in body 25 of knotless suture anchor 10 may be diametrically opposed to side opening 90 in body 25 of knotless suture anchor 10. In this form of the invention, distal movement of locking element 30 within knotless suture anchor 10 causes radial expansion of the body of the knotless suture anchor 10 so as to secure the knotless suture anchor 10 to surrounding bone, and captures the suture within the interior of the knotless suture anchor 10, whereby to secure the suture to the knotless suture anchor 10 (and hence to the bone within which the knotless suture anchor is secured).

Figure 83:
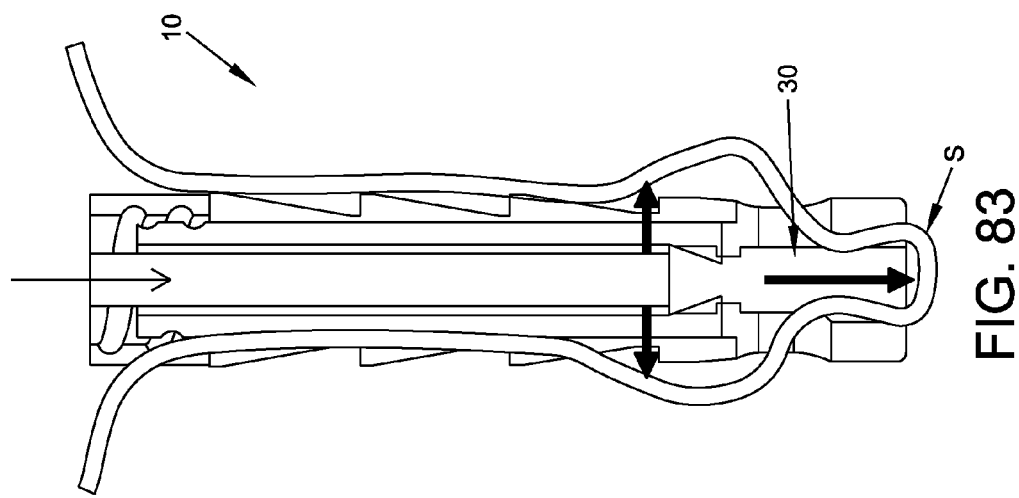
FIGS. 82 and 83 are schematic views showing another alternative form of knotless suture anchor and the distal end of its associated inserter.
Figure 82:
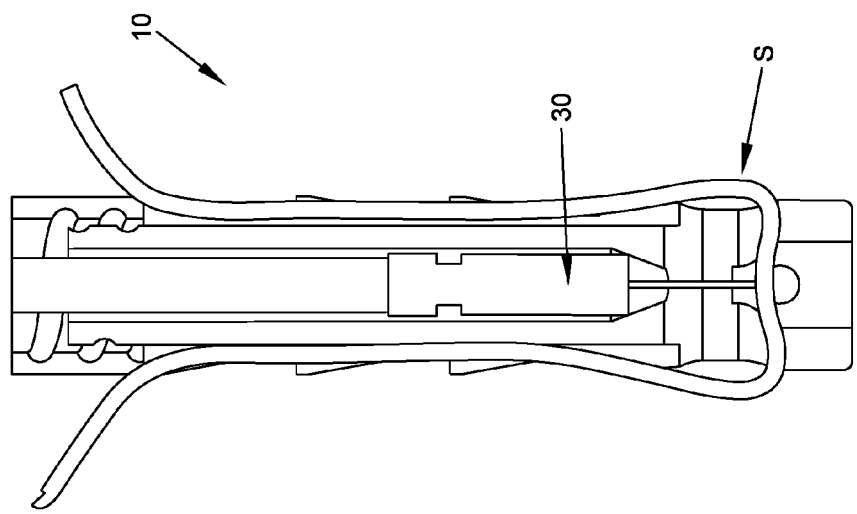
Figure 86:
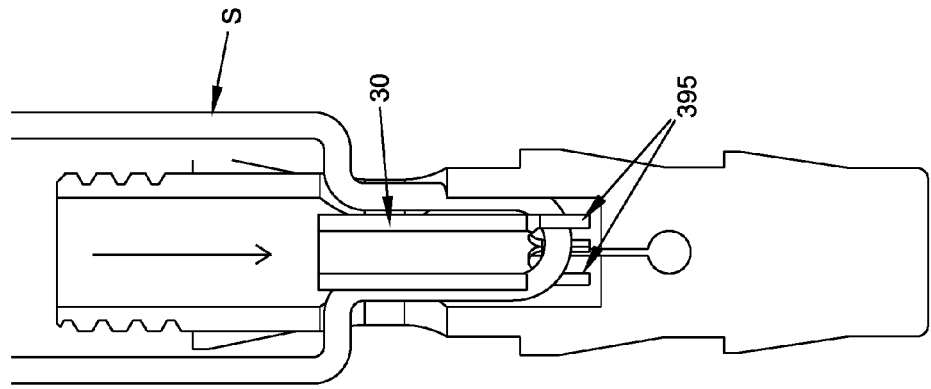
Figure 85:
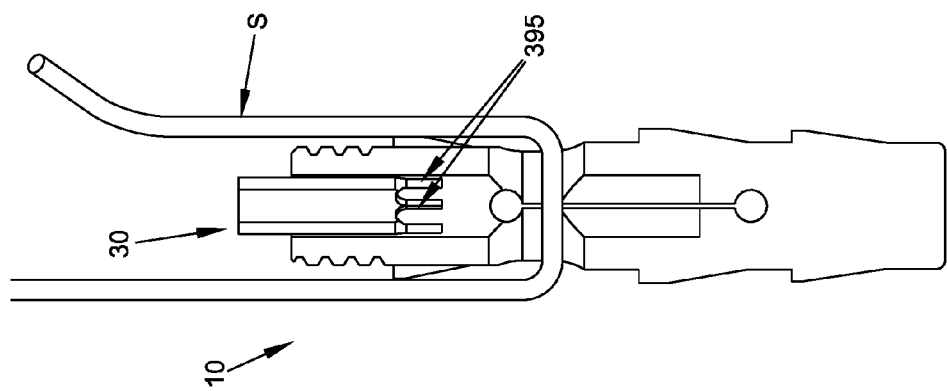
Figure 84:
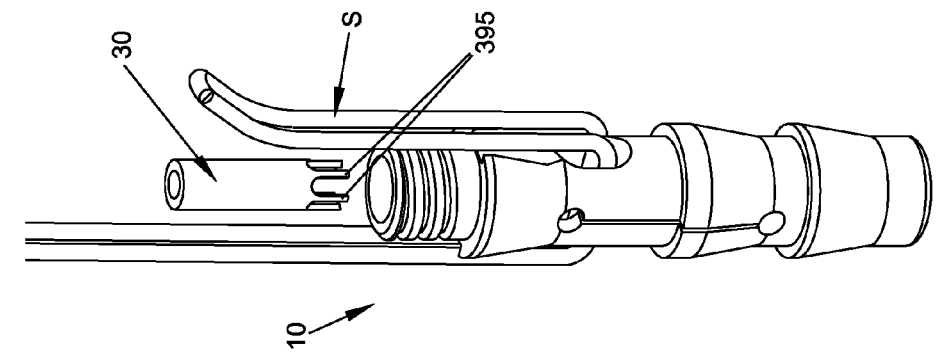
Figure 88:
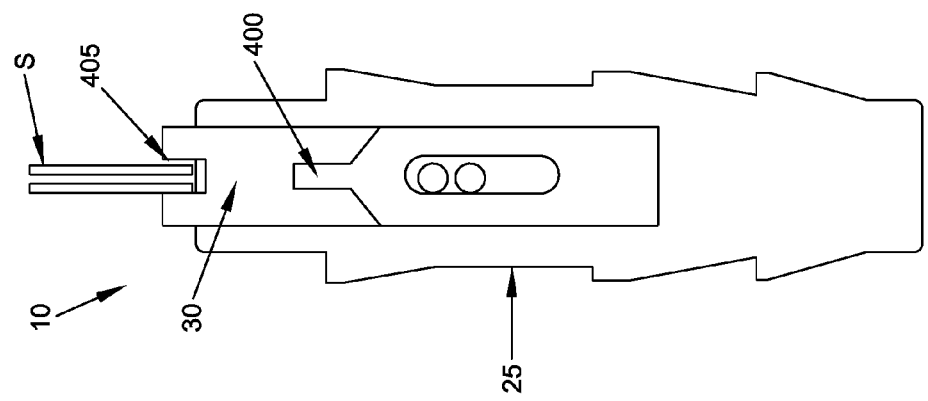
Figure 89:
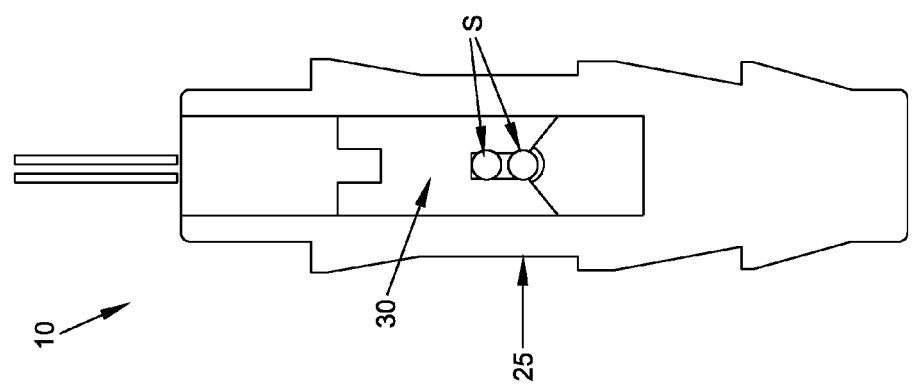
Figure 90:
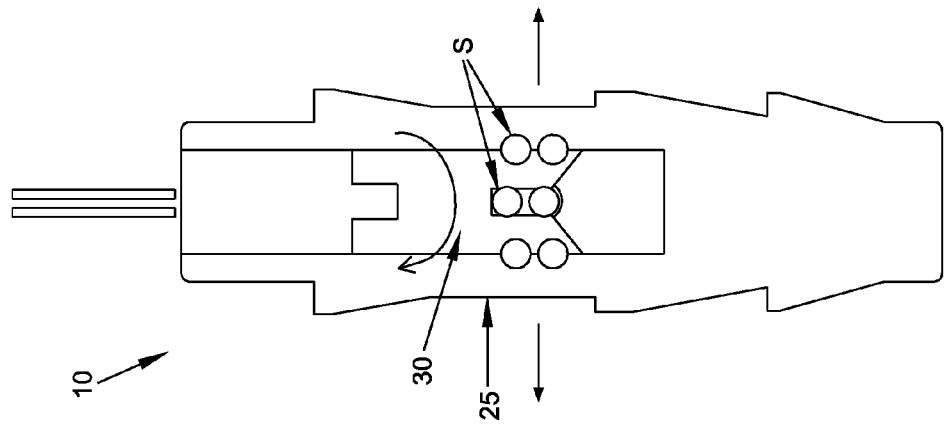

In yet another form of the invention, and looking now at FIGS. 82 and 83, the construction of knotless suture anchor 10 is generally similar to the construction shown in FIGS. 80 and 81, except that when locking element 30 is driven distally to expand the body of the knotless suture anchor and capture suture S to the body of the knotless suture anchor, locking element 30 drives suture S out the distal end of the suture anchor.

Figure 86:
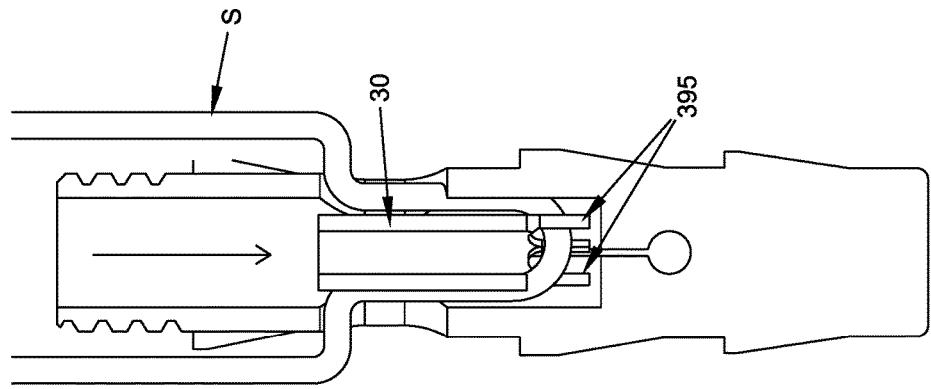
FIGS. 84-86 are schematic views showing another alternative form of knotless suture anchor.
Figure 85:
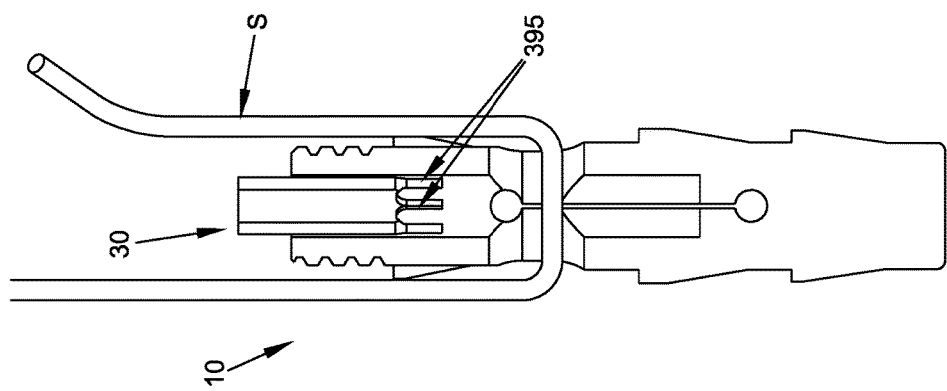
Figure 84:
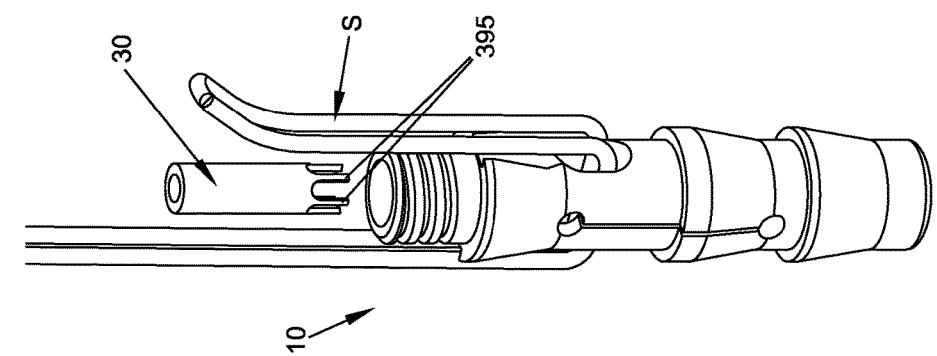

In another form of the invention, and looking now at FIGS. 84-86, the construction of knotless suture anchor 10 is similar to the construction shown in FIGS. 80 and 81, except that locking element 30 includes fingers 395 for piercing suture S as locking element 30 is driven distally, whereby to enhance fixation of suture S within knotless suture anchor 10. Preferably, suture S is braided which enables fingers 395 to interdigitate between the individual fibers of suture S.

In still another form of the invention, and looking now at FIGS. 87-90, the construction of knotless suture anchor 10 is similar to the construction shown in FIGS. 79-81, except that locking element 30 comprises a slot 400 in its distal end and a slot 405 in its proximal end, with distal slot 400 receiving suture S therein when locking element 30 is driven distally, and proximal slot 405 thereafter allowing locking element 30 to be rotated (e.g., by inserting a driver, not shown, into proximal slot 405), whereby to wind suture S about locking element 30 (FIGS. 88-90) and thereby enhance fixation of suture S within knotless suture anchor 10. Significantly, as suture S is wound about locking element 30, the combined volume of locking element 30 and suture S increases so as to cause radial expansion of the body of the knotless suture anchor, whereby to secure the knotless suture anchor to surrounding bone.

Use of the Novel Knotless Suture Anchor System for Other Tissue Re-Attachment It should be appreciated that knotless suture anchor system 5 may also be used for re-attaching other soft tissue of the hip joint, or for re-attaching tissue of other joints, or for re-attaching tissue elsewhere in the body. In this respect it should be appreciated that knotless suture anchor system 5 may be used to attach soft tissue to bone or soft tissue to other soft tissue, or for attaching objects (e.g., prostheses) to bone or other tissue.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for securing a first object to a second object, the apparatus comprising:
    an anchor, the anchor comprising:
        an elongated body having a distal end, a proximal end, and a lumen extending between the distal end and the proximal end, the lumen comprising a distal section and a proximal section, the distal section of the lumen having a wider diameter than the proximal section of the lumen;
        a window extending through the side wall of the elongated body and communicating with the lumen, the window being disposed in the vicinity of an intersection between the distal section of the lumen and the proximal section of the lumen and being sized to receive a first object therein;
        an elongated element extending through the lumen of the elongated body, the elongated element comprising a proximal end and a distal end; and
        a locking element mounted to the distal end of the elongated element and disposed in the distal section of the lumen;
        whereby, when the elongated body is disposed in a second object, and a first object extends through the window, and the locking element is thereafter moved proximally, proximal movement of the locking element causes the elongated body to capture the first object to the elongated body, whereby to secure the first object to the second object; and
    an inserter, the inserter comprising:
        a handle;
        a shaft having a distal end and a proximal end, with a lumen extending therebetween, the proximal end of the shaft being mounted to the handle and the distal end of the shaft being configured to releasably engage the elongated body;
        a retractable sheath disposed movably coaxially about the shaft; and
        a movable tab mounted to the proximal end of the retractable sheath for moving the retractable sheath relative to the shaft.

2. Apparatus according to claim 1 wherein the retractable sheath is movable between a first extended position and a second retracted position, and further wherein the retractable sheath is disposed coaxially over at least a portion of the elongated body when the retractable sheath is in its first extended position, and the retractable sheath is withdrawn from the elongated body when the retractable sheath is in its second retracted position.

3. Apparatus according to claim 2 wherein the retractable sheath is spring-biased into its first extended position.

4. Apparatus according to claim 2 wherein the distal end of the elongated body protrudes from the retractable sheath when the retractable sheath is in its first extended position.

5. Apparatus according to claim 4 further comprising an overtube mounted to the handle and extending distally therefrom, the overtube being mounted coaxially about the retractable sheath and terminating proximal to the distal end of the retractable sheath when the retractable sheath is in its first extended position.

6. Apparatus according to claim 5 wherein the handle comprises an opening, and the movable tab is slidably disposed in the opening, such that by moving the movable tab proximally within the opening, the retractable sheath is retracted proximally, and such that by moving the movable tab distally within the opening, the retractable sheath is advanced distally.

7. Apparatus according to claim 6 wherein the opening comprises a T-shaped slot.

8. Apparatus according to claim 7 wherein the T-shaped slot comprises a longitudinally-extending section which extends parallel to the longitudinal axis of the shaft, and a laterally-extending section which extends at an oblique angle to the longitudinal axis of the shaft.

9. Apparatus according to claim 8 wherein the retractable sheath is movable relative to the shaft when the movable tab is disposed in the longitudinally-extending section of T-shaped slot and wherein the retractable sheath is not movable relative to the shaft when the movable tab is disposed in the laterally-extending section of T-shaped slot.

10. Apparatus according to claim 6 wherein the opening comprises an L-shaped slot.

11. Apparatus according to claim 6 wherein the handle further comprises a releasable locking mechanism, the releasable locking mechanism being configured to selectively lock the movable tab in a desired position within the opening.

12. Apparatus according to claim 11 wherein the releasable locking mechanism comprises at least one from the group consisting of a detent, a snap and a recess.

13. Apparatus according to claim 6 wherein the handle further comprises markings along the opening for indicating the position of the retractable sheath relative to the position of the movable tab.

14. Apparatus for securing a suture to a bone, the apparatus comprising:
an anchor configured to have the suture connected thereto; and
an inserter for manipulating the anchor, the inserter comprising:
a handle;
a shaft mounted to the handle and configured to releasably hold the anchor thereto;
a retractable sheath movably mounted to the handle, the retractable sheath having a first extended position and a second retracted position, wherein the retractable sheath is disposed coaxially over at least a portion of the anchor when the retractable sheath is in its first extended position, and the retractable sheath is withdrawn from the anchor when the retractable sheath is in its second retracted position; and
an outer tube fixedly mounted to the handle, the outer tube being disposed coaxially over the retractable sheath.

15. Apparatus according to claim 14 wherein the retractable sheath is spring-biased into its first extended position.

16. A method for securing a first object to a second object, the method comprising:
providing apparatus comprising:
an anchor, the anchor comprising:
an elongated body having a distal end, a proximal end, and a lumen extending between the distal end and the proximal end, the lumen comprising a distal section and a proximal section, the distal section of the lumen having a wider diameter than the proximal section of the lumen;
a window extending through the side wall of the elongated body and communicating with the lumen, the window being disposed in the vicinity of an intersection between the distal section of the lumen and the proximal section of the lumen and being sized to receive a first object therein;
an elongated element extending through the lumen of the elongated body, the elongated element comprising a proximal end and a distal end; and
a locking element mounted to the distal end of the elongated element and disposed in the distal section of the lumen; and
an inserter, the inserter comprising:
a handle;
a shaft having a distal end and a proximal end, with a lumen extending therebetween, the proximal end of the shaft being mounted to the handle and the distal end of the shaft being configured to releasably engage the elongated body;
a retractable sheath disposed movably coaxially about the shaft; and
a movable tab mounted to the proximal end of the retractable sheath for moving the retractable sheath relative to the shaft;
extending the first object through the window of the elongated body;
using the inserter to position the elongated body in the second object; and
moving the locking element proximally, such that proximal movement of the locking element causes the elongated body to capture the first object to the elongated body, whereby to secure the first object to the second object.

17. A method according to claim 16 wherein the retractable sheath covers a majority of the anchor as the anchor is advanced to the second object, and further wherein the retractable sheath is withdrawn proximally before the elongated body is seated in the second object.

18. A method according to claim 17 wherein the movable tab is used to withdraw the retractable sheath proximally before the elongated body is seated in the second object.

19. A method according to claim 17 wherein engagement of the retractable sheath with the second object causes the retractable sheath to be withdrawn proximally before the elongated body is seated in the second object.

20. A method according to claim 16 wherein the handle comprises an opening, and the movable tab is slidably disposed in the opening, such that by moving the movable tab proximally within the opening, the retractable sheath is retracted proximally, and such that by moving the movable tab distally within the opening, the retractable sheath is advanced distally.

21. A method according to claim 20 wherein the opening comprises a T-shaped slot.

22. A method according to claim 21 wherein the T-shaped slot comprises a longitudinally-extending section which extends parallel to the longitudinal axis of the shaft, and a laterally-extending section which extends at an oblique angle to the longitudinal axis of the shaft.

23. A method according to claim 22 wherein the retractable sheath is movable relative to the shaft when the movable tab is disposed in the longitudinally-extending section of T-shaped slot and wherein the retractable sheath is not movable relative to the shaft when the movable tab is disposed in the laterally-extending section of T-shaped slot.

24. A method for securing a suture to a bone, the method comprising:
   providing apparatus comprising:
      an anchor configured to have the suture connected thereto; and
      an inserter for manipulating the anchor, the inserter comprising:
         a handle;
         a shaft mounted to the handle and configured to releasably hold the anchor thereto;
         a retractable sheath movably mounted to the handle, the retractable sheath having a first extended position and a second retracted position, wherein the retractable sheath is disposed coaxially over at least a portion of the anchor when the retractable sheath is in its first extended position, and the retractable sheath is withdrawn from the anchor when the retractable sheath is in its second retracted position; and
         an outer tube fixedly mounted to the handle, the outer tube being disposed coaxially over the retractable sheath;
   connecting the suture to the anchor; and
   using the inserter to position the anchor in the bone, whereby to secure the suture to the bone.

25. A method according to claim 24 wherein the inserter comprises a movable tab, and further wherein the movable tab is used to withdraw the retractable sheath proximally before the anchor is positioned in the bone.

26. A method according to claim 24 wherein engagement of the retractable sheath with the bone causes the retractable sheath to be withdrawn proximally before the anchor is positioned in the bone.

27. A method according to claim 24 wherein the retractable sheath is spring-biased into its first extended position.

\* \* \* \* \*